(12) United States Patent
Gholami

(10) Patent No.: US 11,707,571 B2
(45) Date of Patent: *Jul. 25, 2023

(54) HIERARCHICAL ADAPTIVE CLOSED-LOOP FLUID RESUSCITATION AND CARDIOVASCULAR DRUG ADMINISTRATION SYSTEM

(71) Applicant: Autonomous Healthcare, Inc., Hoboken, NJ (US)

(72) Inventor: Behnood Gholami, Hoboken, NJ (US)

(73) Assignee: Autonomous Healthcare, Inc., Hoboken, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/731,347

(22) Filed: Apr. 28, 2022

(65) Prior Publication Data
US 2022/0265929 A1    Aug. 25, 2022

Related U.S. Application Data

(63) Continuation of application No. 17/090,729, filed on Nov. 5, 2020, now Pat. No. 11,338,087, which is a
(Continued)

(51) Int. Cl.
*A61M 5/172*    (2006.01)
*G16H 20/17*    (2018.01)
(Continued)

(52) U.S. Cl.
CPC ............. *A61M 5/1723* (2013.01); *G06N 3/08* (2013.01); *G16H 10/60* (2018.01); *G16H 20/17* (2018.01);
(Continued)

(58) Field of Classification Search
CPC ...... A61M 5/00; A61M 5/1723; G16H 10/00; G16H 10/60; G16H 20/00; G16H 20/17; G16H 40/63
(Continued)

(56) References Cited

U.S. PATENT DOCUMENTS 4,080,966 A    3/1978    McNally et al.
5,116,312 A    5/1992    Blankenship et al.
(Continued)

FOREIGN PATENT DOCUMENTS

AU    2019280053 B2    5/2020
AU    2020264409 B2    11/2021
(Continued)

OTHER PUBLICATIONS

Bighamian, Ramin; Systems-Level Modeling and Validation of Cardiovascular System Responses to Fluid and Vasopressor Infusion for Automated Critical Care; University of Maryland, College Park. ProQuest Dissertations Publishing, 2017. 10267363. (Year: 2017).*

(Continued)

*Primary Examiner* — Hiep V Nguyen
(74) *Attorney, Agent, or Firm* — New River Valley IP Law, P.C.; Michele L. Mayberry

(57) ABSTRACT

The present disclosure describes a closed-loop fluid resuscitation and/or cardiovascular drug administration system that uses continuous measurements and adaptive control (Continued)

architecture. The adaptive control architecture uses a function approximator to identify unknown dynamics and physiological parameters of a patient to compute appropriate infusion rates and to regulate the endpoint of resuscitation.

12 Claims, 36 Drawing Sheets

Related U.S. Application Data continuation of application No. 16/680,145, filed on Nov. 11, 2019, now Pat. No. 10,926,031, which is a continuation-in-part of application No. PCT/US2018/032369, filed on May 11, 2018.

(60) Provisional application No. 62/505,232, filed on May 12, 2017.

(51) Int. Cl.
  *G16H 10/60*  (2018.01)
  *G16H 40/63*  (2018.01)
  *G06N 3/08*  (2023.01)

(52) U.S. Cl.
  CPC ..... *G16H 40/63* (2018.01); *A61M 2205/3569* (2013.01); *A61M 2205/50* (2013.01); *A61M 2205/502* (2013.01); *A61M 2205/52* (2013.01); *A61M 2230/00* (2013.01); *A61M 2230/06* (2013.01); *A61M 2230/30* (2013.01)

(58) Field of Classification Search
  USPC .......................................................... 705/2
  See application file for complete search history.

(56) References Cited

U.S. PATENT DOCUMENTS

| | | | |
|---|---|---|---|
| 7,857,803 B1 | 12/2010 | Salinas et al. | |
| 7,879,020 B1 | 2/2011 | Salinas et al. | |
| 8,579,859 B2 | 11/2013 | Kramer et al. | |
| 8,617,135 B2 | 12/2013 | Rinehart et al. | |
| 9,022,974 B2 | 5/2015 | Rinehart et al. | |
| 9,526,833 B2 | 12/2016 | Gelfand et al. | |
| 9,950,112 B2 | 4/2018 | Melker et al. | |
| 10,042,986 B2 | 8/2018 | Ruchti et al. | |
| 10,130,766 B1 | 11/2018 | Bibian et al. | |
| 10,434,255 B2 | 10/2019 | Rinehart et al. | |
| 10,926,031 B2 | 2/2021 | Gholami et al. | |
| 2003/0200189 A1 | 10/2003 | Meng et al. | |
| 2011/0230824 A1* | 9/2011 | Salinas .................. | A61B 5/412 604/66 |
| 2012/0179007 A1 | 7/2012 | Rinehart et al. | |
| 2012/0179135 A1* | 7/2012 | Rinehart ............. | A61M 5/1723 604/503 |
| 2012/0179136 A1 | 7/2012 | Rinehart et al. | |
| 2012/0283631 A1 | 11/2012 | Salinas et al. | |
| 2013/0218126 A1 | 8/2013 | Hayter et al. | |
| 2013/0296823 A1 | 11/2013 | Melker et al. | |
| 2014/0276379 A1 | 9/2014 | Uram et al. | |
| 2015/0209514 A1 | 7/2015 | Rinehart et al. | |
| 2015/0258277 A1 | 9/2015 | Halpert et al. | |
| 2019/0046723 A1 | 2/2019 | Halpert et al. | |
| 2020/0114077 A1 | 4/2020 | Gholami et al. | |

FOREIGN PATENT DOCUMENTS

| | | | |
|---|---|---|---|
| CA | 3092786 C | 9/2022 | |
| CN | 110869074 B | 8/2022 | |
| EP | 3621676 A1 | 3/2020 | |
| EP | 3851141 A1 | 7/2021 | |
| JP | 2010535045 A | 11/2010 | |
| JP | 6039016 B2 * | 12/2016 | ......... A61B 5/14532 |
| JP | 6039016 B2 | 12/2016 | |
| JP | 6886560 B2 | 6/2021 | |
| JP | 7124168 B2 | 8/2022 | |
| WO | WO-2014035672 A2 * | 3/2014 | ......... A61B 5/14532 |
| WO | 2014210465 A1 | 12/2014 | |
| WO | WO-2017220683 A1 * | 12/2017 | ......... A61B 17/3415 |
| WO | 2018209268 A1 | 11/2018 | |

OTHER PUBLICATIONS

Co-Pending Australian Application No. 2020213388, Patent Examination Report No. 1 dated Sep. 14, 2020, 4 pages.
Co-Pending Australian Application No. 2020213388, Patent Examination Report No. 2 dated Nov. 12, 2020, 3 pages.
Co-Pending Australian Application No. 2020213388, Request for Expedited Examination and Voluntary Amendment, Filed Aug. 28, 2020, 155 pages.
Co-Pending Australian Application No. 2020213388, Response to Patent Examination Report No. 1, filed Nov. 12, 2020, 139 pages.
Co-Pending Australian Application No. 2020213388, Response to Patent Examination Report No. 2 dated Nov. 23, 2020, 2 pages.
Co-Pending Australian Application No. 2020264408, Certificate of Grant, dated Jul. 15, 2021, 1 page.
Co-Pending Australian Application No. 2020264408, Claims as accepted, dated Dec. 24, 2020, 2 pages.
Co-Pending Australian Application No. 2020264408, Examination Report No. 1 dated Feb. 24, 2021, 3 pages.
Co-Pending Australian Application No. 2020264408, Notice of Acceptance dated Mar. 19, 2021, 3 pages.
Co-Pending Australian Application No. 2020264408, Notice of Patent Grant, Mar. 25, 2021, 1 page.
Co-Pending Australian Application No. 2020264409, Amendment filed Dec. 24, 2020, 134 pages.
Co-Pending Australian Application No. 2020264409, Certificate of Patent Grant dated Feb. 24, 2022, 1 page.
Co-Pending Australian Application No. 2020264409, Examination Report No. 1 dated Feb. 24, 2021, 4 pages.
Co-Pending Australian Application No. 2020264409, Notice of Acceptance dated Oct. 28, 2021, 3 pages.
Co-Pending Australian Application No. 2020264409, Response to Examination Report No. 1, dated Oct. 20, 2021, 121 pages.
Co-Pending Canadian Application No. 3,092,786, Examiner's Report dated Apr. 16, 2021, 4 pages.
Co-Pending Canadian Application No. 3,092,786, Examiner's Report dated Nov. 6, 2020, 7 pages.
Co-Pending Canadian Application No. 3,092,786, Examiner's Report dated Sep. 27, 2021, 4 pages.
Co-Pending Canadian Application No. 3,092,786, Response to Apr. 16, 2021 Examiner's Report, filed Aug. 12, 2021, 11 pages.
Co-Pending Canadian Application No. 3,092,786, Response to Nov. 6, 2020 Examiner's Report and amended claims filed Mar. 5, 2021, 11 pages.
Co-Pending Canadian Application No. 3,092,786, Response to Sep. 27, 2021 Examiner's Report, filed Jan. 11, 2022, 24 pages.
Co-Pending Canadian National Stage Application filed Sep. 1, 2020, based on International Application No. PCT/US2018/032369, Voluntary Amendment filed Sep. 1, 2020, 4 pages.
Co-Pending Chinese Application No. 201880046101.9, Office Action dated Jul. 28, 2021 (7 pages) with English Translation (7 pages).
Co-Pending Chinese Application No. 201880046101.9, Office Action dated Mar. 16, 2022 (9 pages) and English Translation (11 pages).
Co-Pending Chinese Application No. 201880046101.9, Request for initiative amendments (with English version of the claims) filed Aug. 31, 2020 72 pages and 17 pages (2 pdfs).
Co-Pending Chinese Application No. 201880046101.9, Response to Jul. 28, 2021 Office Action dated Nov. 26, 2021 (39 pages) with English Translation of the Amended Claims (18 pages).
Co-Pending European Application No. 18798966, Amendment dated Jul. 14, 2020, 98 pages.
Co-Pending European Application No. 18798966, Communication Pursuant to Article 94(3) EPC and Examination Report, dated Nov. 4, 2020, 8 pages.
Co-Pending European Application No. 18798966, Communication Pursuant to Article 94(3) EPC, dated Dec. 13, 2021, 3 pages.

(56) References Cited

OTHER PUBLICATIONS

Co-Pending European Application No. 18798966, Communication Pursuant to Article 94(3) EPC, dated Jun. 14, 2021, 4 pages.
Co-Pending European Application No. 18798966, Extended European Search Report dated Oct. 9, 2020, 3 pages.
Co-Pending European Application No. 18798966, Response to Dec. 13, 2021 Communication Pursuant to Article 94(3) EPC, filed Apr. 11, 2022, 15 pages.
Co-Pending European Application No. 18798966, Response to Jan. 8, 2020 Communication pursuant to Rules 161(2) and 162 EPC and amended claims filed Jul. 15, 2020, 98 pages.
Co-Pending European Application No. 18798966, Response to Nov. 4, 2020 Communication Pursuant to Article 94(3) EPC and Examination Report, filed Mar. 11, 2021, 18 pages.
Co-Pending European Application No. 18798966, Response to the Jun. 14, 2021 Communication Pursuant to Article 94(3) EPC, filed Oct. 14, 2021, 14 pages.
Co-Pending European Application No. 20194644.9, Brief Communication dated May 14, 2021, 2 pages.
Co-Pending European Application No. 20194644.9, Communication from the EPO, Invitation Pursuant to Rule 63(1) EPC, dated Apr. 15, 2021, 4 pages.
Co-Pending European Application No. 20194644.9, Extended European Search Report dated Mar. 25, 2021, 5 pages.
Co-Pending European Application No. 20194644.9, Extended European Search Report, dated Jun. 21, 2021, 6 pages.
Co-Pending European Application No. 20194644.9, file history through Jan. 2022, 230 pages.
Co-Pending European Application No. 20194644.9, Petition dated Mar. 31, 2021, 3 pages.
Co-Pending European Application No. 20194644.9, Response to Communication Pursuant to Rule 69 EPC and Invitation Pursuant to Rule 70a(1) EPC, filed Jan. 12, 2022, 16 pages.
Co-Pending Japanese Application No. 2020-513484 (ID No. 519401505), Decision to Grant, 3 pages.
Co-Pending Japanese Application No. 2020-513484 (ID No. 519401505), English translation of Voluntary Amendment filed Apr. 3, 2020, 5 pages.
Co-Pending Japanese Application No. 2020-513484 (ID No. 519401505), Filed Nov. 11, 2019, English Version of Specification and Claims, 48 pages.
Co-Pending Japanese Application No. 2020-513484 (ID No. 519401505), Office Action dated Jul. 10, 2020 and English translation with pending claims in English, 16 pages and 5 pages (2 pdfs).
Co-Pending Japanese Application No. 2020-513484 (ID No. 519401505), Office Action dated Nov. 16, 2020 and English translation, 4 pages and 4 pages (2 pdfs).
Co-Pending Japanese Application No. 2020-513484 (ID No. 519401505), Response to Office Action filed Feb. 15, 2021 and English translation of the claims, 7 pages and 5 pages (2 pdfs).
Co-Pending Japanese Application No. 2020-513484 (ID No. 519401505), Response to Office Action filed Oct. 8, 2020 and English translation, 9 pages and 9 pages (2 pdfs).
Co-Pending Japanese Application No. 2020-513484 (ID No. 519401505), Voluntary Amendment and Request for Examination filed Apr. 3, 2020, with English translation of claims, 13 pages.
Bighamian, R., Reisner, A.T. and Hahn, J.O., 2016. A lumped-parameter subject-specific model of blood volume response to fluid infusion. Frontiers in Physiology, 7, p. 390.
Jin, X., Bighamian, R. and Hahn, J.O., 2018. Development and in silico evaluation of a model-based closed-loop fluid resuscitation control algorithm. IEEE Transactions on Biomedical Engineering, 66(7), pp. 1905-1914.
(Gholami, Behnood et al.) Co-pending U.S. Appl. No. 16/680,145, filed Nov. 11, 2019, Specification, Claims, and Figures.
(Gholami, Behnood et al.) Co-pending Application No. PCT/US18/32369, filed May 11, 2018 and published as WO2018/209268 on Nov. 15, 2018, Specification, Claims, Figures.

(Gholami, Behnood et al.) Co-pending Australian Application No. 2019280053, filed Dec. 12, 2019, Specification, Claims, Figures.
(Gholami, Behnood et al.) Co-pending Australian Application No. 2020264409, Filed Nov. 6, 2020, Specification, Claims, Figures, 111 pages.
(Gholami, Behnood) Co-pending U.S. Appl. No. 17/090,729, filed Nov. 5, 2020, Specification, Claims, Figures.
(Gholami, Behnood) Co-pending Australian Application No. 2020202414, filed Apr. 8, 2020, Specification, claims, figures (see AU 2019280053).
(Gholami, Behnood) Co-pending Australian Application No. 2020203914, Filed Jun. 12, 2020, Specification, Claims, Figures (see PCT/US18/32369).
(Gholami, Behnood) Co-pending Australian Application No. 2020203918, Filed Jun. 12, 2020, Specification, Claims, Figures (see PCT/US18/32369).
(Gholami, Behnood) Co-pending Australian Application No. 2020213388, Filed Aug. 7, 2020, Specification, Claims, Figures (see PCT/US18/32369).
(Gholami, Behnood) Co-pending Australian Application No. 2020264408, Filed Nov. 6, 2020, Specification, Claims, Figures, 111 pages.
(Gholami, Behnood) Co-pending Canadian National Stage Application filed Sep. 1, 2020, based on International Application No. PCT/US2018/032369, Specification and Claims.
(Gholami, Behnood) Co-pending Chinese Application No. 201880046101.9, filed Jan. 9, 2020, Specification, Claims, Figures (See PCT/US18/32369).
(Gholami, Behnood) Co-pending European Application No. 18798966, filed Dec. 12, 2019, Specification, Claims, Figures (See PCT/US18/32369).
(Gholami, Behnood) Co-pending European Application No. 20194644.9, filed Sep. 4, 2020, Specification, Claims, Figures, 84 pages.
(Gholami, Behnood) Co-pending Japanese Application No. 2020-513484 (ID No. 519401505), Filed Nov. 11, 2019, Specification, Claims, Figures (See PCT/US18/32369).
(Gholami, Behnood) Co-pending Japanese Application No. 2021-082023, Filed May 14, 2021, Specification, Claims, Figures (See PCT/US18/32369).
Alexander, B., Rinehart, J., Cannesson, M., Duranteau, J. and Joosten, A., 2019. Closed-loop hemodynamic management. Best Practice & Research Clinical Anaesthesiology, 33(2), pp. 199-209.
Bailey, James M., and Steven L. Shafer. "A simple analytical solution to the three-compartment pharmacokinetic model suitable for computer-controlled infusion pumps." IEEE Transactions on biomedical engineering 38.6 (1991): 522-525.
Bailey, James M., and Wassim M. Haddad. "Drug dosing control in clinical pharmacology." IEEE Control Systems Magazine 25.2 (2005): 35-51.
Bert, J. L., et al. "A model of fluid and solute exchange in the human: validation and implications." Acta physiologica scandinavica 170.3 (2000): 201-209.
Bighamian, R., Reisner, A.T. and Hahn, J.O., 2013. An analytic tool for prediction of hemodynamic responses to vasopressors. IEEE Transactions on Biomedical Engineering, 61(1), pp. 109-118.
Bighamian, R., Soleymani, S., Reisner, A.T., Seri, I. and Hahn, J.O., 2014. Prediction of hemodynamic response to epinephrine via model-based system identification. IEEE journal of biomedical and health informatics, 20(1), pp. 416-423.
Brown, Sue A., et al. "Six-month randomized, multicenter trial of closed-loop control in type 1 diabetes." New England Journal of Medicine 381.18 (2019): 1707-1717.
Cattermole, G. N. et al., "The normal ranges of cardiovascular parameters measured using the ultrasonic cardiac output monitor", Physiological Reports 5.6 John Wiley & Sons, Inc. (Mar. 2017), Abstract.
Chapple, C., et al. "A model of human microvascular exchange: parameter estimation based on normals and nephrotics." Computer methods and programs in biomedicine 41.1 (1993): 33-54.
Co-Pending U.S. Appl. No. 16/680,145, File History through Jan. 2021, 202 pages.
Co-Pending U.S. Appl. No. 17/090,729, File History through Apr. 2022, 60 pages.

(56) References Cited

OTHER PUBLICATIONS

Co-Pending Application No. PCT/US18/32369 International Search Report and Written Opinion dated Aug. 8, 2018.
Co-Pending Australian Application No. 2019280053, Certificate of Grant dated Aug. 20, 2020.
Co-Pending Australian Application No. 2019280053, Examination Report dated Feb. 17, 2020, 4 pages.
Co-Pending Australian Application No. 2019280053, Notice of Acceptance dated Apr. 22, 2020, 3 pages.
Co-Pending Australian Application No. 2019280053, Notice of Grant of Patent, dated Aug. 20, 2020, 1 page.
Co-Pending Australian Application No. 2019280053, Response to Feb. 17, 2020 Examination Report filed Apr. 1, 2020, 149 pages.
Co-Pending Australian Application No. 2020202414, Examination Report dated Apr. 15, 2020, 4 pages.
Co-Pending Australian Application No. 2020202414, Notice of Acceptance, dated Jun. 25, 2020, 3 pages.
Co-Pending Australian Application No. 2020202414, Response to Apr. 15, 2020 Patent Examination Report No. 1, dated Jun. 11, 2020, 147 pages.
Co-Pending Australian Application No. 2020203914, Certificate of Grant, dated Aug. 20, 2020, 2 pages.
Co-Pending Australian Application No. 2020203914, Claims as Accepted, dated Aug. 7, 2020, 3 pages.
Co-Pending Australian Application No. 2020203914, Notice of Acceptance, dated Aug. 20, 2020, 3 pages.
Co-Pending Australian Application No. 2020203914, Patent Examination Report No. 1, dated Jul. 10, 2020, 4 pages.
Co-Pending Australian Application No. 2020203914, Response to Jul. 10, 2020 Patent Examination Report No. 1, dated Aug. 7, 2020, 140 pages.
Co-Pending Australian Application No. 2020203918, Certificate of Grant dated Dec. 17, 2020, 2 pages.
Co-Pending Australian Application No. 2020203918, Notice of Acceptance dated Aug. 20, 2020, 3 pages.
Co-Pending Australian Application No. 2020203918, Patent Examination Report No. 1, dated Jul. 10, 2020, 4 pages.
Co-Pending Australian Application No. 2020203918, Response to Jul. 10, 2020 Patent Examination Report No. 1, dated Aug. 7, 2020, 140 pages.
Co-Pending Australian Application No. 2020213388, Certificate of Grant, dated Mar. 25, 2021, 1 page.
Co-Pending Australian Application No. 2020213388, Claims as accepted, dated Nov. 12, 2020, 3 pages.
Co-Pending Australian Application No. 2020213388, Notice of Acceptance, Nov. 27, 2020, 149 pages.
Co-Pending Japanese Application No. 2021-082023, English translation of the claims (15 pages) relating to Voluntary Amendment filed Jun. 10, 2021.
Co-Pending Japanese Application No. 2021-082023, Office Action dated Apr. 4, 2022 (3 pages) with English Translation (4 pages).
Co-Pending Japanese Application No. 2021-082023, Voluntary Amendment and Request for Examination filed Jun. 10, 2021 (74 pages), with English translation of the claims (15 pages).
Gholami, Behnood et al. A pilot study evaluating adaptive closed-loop fluid resuscitation during states of absolute and relative hypovolemia in dogs. Journal of Veterinary Emergency and Critical Care, 28(5) 2018, pp. 436-446.
Gholami, Behnood et al., "Closed-Loop Control for Fluid Resuscitation: Recent Advances and Future Challenges", Front. Vet. Sci, 8:642440, Feb. 23, 2021.
Gholami, Behnood, et al. "Clinical decision support and closed-loop control for cardiopulmonary management and intensive care unit sedation using expert systems." IEEE transactions on control systems technology 20.5 (2011): 1343-1350.
Gholami, Behnood, et al. "Closed-Loop Control for Cardiopulmonary Management and Intensive Care Unit Sedation using Digital Imaging" Ph.D. Thesis, Georgia Institute of Technology, 2010.
Gyenge, Christina C., et al. "Transport of fluid and solutes in the body I. Formulation of a mathematical model." American Journal of Physiology-Heart and Circulatory Physiology 277.3 (1999): H1215-H1227.
Haddad, Wassim M., J. M. Bailey, T. Hayakawa, and N. Hovakimyan, "Neural Network Adaptive Output Feedback Control for Intensive Care Unit Sedation and Intraoperative Anesthesia," IEEE Trans. Neural Networks, vol. 18, pp. 1049-1066, 2007.
Haddad, Wassim M., and James M. Bailey. "Closed-loop control for intensive care unit sedation." Best Practice & Research Clinical Anaesthesiology 23.1 (2009): 95-114.
Haddad, Wassim M., et al. "Clinical decision support and closed-loop control for intensive care unit sedation." Asian Journal of Control 15.2 (2013): 317-339.
Haddad, Wassim M., K. Y. Volyanskyy, J. M. Bailey, and J. J. Im, "Neuroadaptive Output Feedback Control for Automated Anesthesia with Noisy EEG Measurements," IEEE Trans. Contr. Syst. Tech., vol. 19, pp. 311-326, 2011.
Ho, Dao H.; Hemorrhagic Shock and Fluid Resuscitation Alter Gene Expression of Chromatin Modification Enzymes in Thoracic Aorta of Swine (Sus scrofa); FASEB Journal 31, Suppl. 1: 859.9 (Apr. 2017), Abstract.
Hoskins, Stephen L., et al. "Closed-loop resuscitation of burn shock." Journal of burn care & research 27.3 (2006): 377-385.
Kovatchev, Boris P., et al. "In silico preclinical trials: a proof of concept in closed-loop control of type 1 diabetes" (2009): 44-55.
Kramer, George C., et al. "Closed-loop control of fluid therapy for treatment of hypovolemia." Journal of Trauma and Acute Care Surgery 64.4 (2008): S333-S341.
Libert, Nicolas, et al. "Performance of closed-loop resuscitation in a pig model of haemorrhagic shock with fluid alone or in combination with norepinephrine, a pilot study." Journal of Clinical Monitoring and Computing (2020): 1-13.
Libert, Nicolas, et al. "Performance of closed-loop resuscitation of haemorrhagic shock with fluid alone or in combination with norepinephrine: an experimental study." Annals of intensive care 8.1 (2018): 89.
Marques, Nicole Ribeiro, et al. "Automated closed-loop resuscitation of multiple hemorrhages: a comparison between fuzzy logic and decision table controllers in a sheep model." Disaster and military medicine 3.1 (2017): 1.
Mirinejad, H., Parvinian, B., Ricks, M., Zhang, Y., Weininger, S., Hahn, J.O. and Scully, C.G., 2019. Evaluation of Fluid Resuscitation Control Algorithms via a Hardware-in-the-Loop Test Bed. IEEE Transactions on Biomedical Engineering, 67(2), pp. 471-481.
Padmanabhan, Regina, Nader Meskin, and Wassim M. Haddad. "Closed-loop control of anesthesia and mean arterial pressure using reinforcement learning." Biomedical Signal Processing and Control 22 (2015): 54-64.
Parvinian, B., Pathmanathan, P., Daluwatte, C., Yaghouby, F., Gray, R.A., Weininger, S., Morrison, T.M. and Scully, C. G., 2019. Credibility evidence for computational patient models used in the development of physiological closed-loop controlled devices for critical care medicine. Frontiers in Physiology, 10, p. 220.
Parvinian, B., Scully, C., Wiyor, H., Kumar, A., & Weininger, S. (2018). Regulatory considerations for physiological closed-loop controlled medical devices used for automated critical care: food and drug administration workshop discussion topics. Anesthesia and analgesia, 126(6), 1916.
Rafie, Abraham D., et al. "Hypotensive resuscitation of multiple hemorrhages using crystalloid and colloids." Shock 22.3 (2004): 262-269.
Rinehart, J., et al. "First closed-loop goal directed fluid therapy during surgery: a pilot study." Annales francaises d'anesthesie et de reanimation. vol. 33. No. 3 Elsevier Masson, 2014.
Rinehart, Joseph et al. Closed-Loop Fluid Resuscitation: Robustness Against Weight and Cardiac Contractility Variations. Anesthesia Analgesia, 2013, 117, 5, pp. 1110-1118.
Rinehart, Joseph, et al. "Closed-loop fluid administration compared to anesthesiologist management for hemodynamic optimization and resuscitation during surgery: an in vivo study." Anesthesia & Analgesia 117.5 (2013): 1119-1129.

(56) References Cited

OTHER PUBLICATIONS

Rinehart, Joseph, et al. "Evaluation of a novel closed-loop fluid-administration system based on dynamic predictors of fluid responsiveness: an in silico simulation study." Critical Care 15.6 (2011): R278.
Rinehart, Joseph, et al. "Feasibility of automated titration of vasopressor infusions using a novel closed-loop controller." Journal of clinical monitoring and computing 32.1 (2018): 5-11.
Salinas, Jose, et al. "Closed-loop and decision-assist resuscitation of burn patients." Journal of Trauma and Acute Care Surgery 64.4 (2008): S321-S332.
Salinas, José, et al. "Computerized decision support system improves fluid resuscitation following severe burns: an original study." Critical care medicine 39.9 (2011): 2031-2038.
Tyagi, A. et al., "Effect of thoracic epidural block on infection-induced inflammatory response: a randomized controlled trial", Journal of Critical Care 38: 6-12, Elsevier Limited (Apr. 1, 2017), Abstract.
Jemura, Kazunori, et al. "Computer-controlled closed-loop drug infusion system for automated hemodynamic resuscitation in endotoxin-induced shock." BMC anesthesiology 17.1 (2017): 145.
Vaid, Sumreen U., et al. "Normotensive and hypotensive closed-loop resuscitation using 3.0% NaCl to treat multiple hemorrhages in sheep." Critical care medicine 34.4 (2006): 1185-1192.
Xu, Jingyuan et al. "Fluid responsiveness predicted by transcutaneous partial pressure of oxygen in patients with circulatory failure: a prospective study", Annals of Intensive Care 7.1: 1-7, Springer Nature B.V. (May 2017), Abstract.

(Gholami, Behnood) Co-pending Canadian Application No. 3,168,739 filed Jul. 25, 2022, Specification, Claims, and Figures.
Co-Pending Canadian Application No. 3,168,739, Voluntary Amendment dated Aug. 29, 2022, 42 pages.
Co-Pending Canadian Application No. 3,168,739, Voluntary Amendment dated Jul. 25, 2022, 15 pages.
Co-Pending Canadian Application No. 3,168,739, Voluntary Amendment dated Nov. 14, 2022, 12 pages.
Co-Pending European Applicaton No. 18798966, Communication Pursuant to Article 71(3) EPC with text intended for grant, dated Jul. 12, 2022, 145 pages.
Co-Pending European Application No. 18798966, Decision to Grant dated Dec. 1, 2022, 1 page.
Co-Pending Japanese Application No. 2021-082023, Argument and Amendment filed Jun. 30, 2022 (8 pages), with English translation of the claims (10 pages).
Co-Pending Chinese Application No. 201880046101.9, English Translation of Allowed Claims, 18 pages.
Co-Pending Chinese Application No. 201880046101.9, Grant Notice dated Jul. 5, 2022 (2 pages) and English Translation (2 pages).
Co-Pending Chinese Application No. 201880046101.9, Patent Certificate No. 5371830, dated Aug. 9, 2022 (2 pages) and English Translation (2 pages).
Co-Pending Chinese Application No. 201880046101.9, Response to Mar. 16, 2022 Office Action, dated May 31, 2022 (43 pages) and English Translation of the Amended Claims (20 pages).
Co-Pending Chinese Application No. 201880046101.9, Search Report dated Jun. 22, 2022, 2 pages.
Co-Pending Chinese Application No. 201880046101.9, English Translation of Remarks in the Response to Mar. 16, 2022 Office Action, dated May 31, 2022 (6 pages).

\* cited by examiner

HIERARCHICAL ADAPTIVE CLOSED-LOOP FLUID RESUSCITATION AND CARDIOVASCULAR DRUG ADMINISTRATION SYSTEM

CROSS REFERENCE

This application is a Continuation application of U.S. patent application Ser. No. 17/090,729, filed Nov. 5, 2020, which published as U.S. Application Publication No. 2021/0128832 on May 6, 2021. The '729 application is a Continuation application of U.S. patent application Ser. No. 16/680,145, filed Nov. 11, 2019, which issued as U.S. Pat. No. 10,926,031 on Feb. 23, 2021. The '145 application is a Continuation-in-Part (CIP) application of International Application No. PCT/US2018/032369, filed May 11, 2018, which published on Nov. 15, 2018 as International Patent Application Publication No. WO2018/209268, and which PCT application claims priority to and the benefit of the filing date of U.S. Provisional Application No. 62/505,232, filed May 12, 2017. All of the foregoing applications are hereby incorporated herein by reference in their entireties.

GOVERNMENT RIGHTS

The invention was made with government support under W81XWH-14-C-1385 by the US Army Medical Research and Material Command, under IIP-1648292 by the National Science Foundation, and under IIP-1831225 by the National Science Foundation. The government has certain rights in the invention.

BACKGROUND

Reliable and consistent fluid resuscitation (i.e., intravenous administration of fluids) is critical for perioperative and intensive care unit (ICU) fluid management in human and animal populations. The goal of fluid resuscitation is to restore blood volume in the circulatory system to an acceptable level to ensure adequate tissue perfusion. However, large intra-patient and inter-patient variability in physiological parameters, and the effects of different illnesses and medications can result in under-resuscitation and over-resuscitation of patients.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the disclosure provides a method for fluid resuscitation and/or cardiovascular drug administration comprising: a) initiating an infusion rate of a fluid and/or a cardiovascular drug into a subject at an infusion rate; b) receiving hemodynamic sensor data of the subject from at least one medical monitoring device attached to the subject by a hierarchical control architecture system, wherein the hierarchical control architecture system comprises: at least one adaptive controller; and a logic-based controller; wherein the subject's hemodynamic data is received by the logic-based controller and the at least one adaptive controller, wherein the at least one adaptive controller and the logic-based controller are in communication with one another; c) generating by the at least one adaptive controller an altered infusion rate based on the subject's hemodynamic data, previous infusion rates, and internal parameters and states of the at least one adaptive controller; d) verifying by the logic-based controller that the subject's hemodynamic data and the at least one adaptive controller states do not violate rules governing the operation of the at least one adaptive controller; e) sending the altered infusion rate from the logic-based controller to at least one infusion pump; f) automatically administering by the at least one infusion pump the fluid and/or cardiovascular drug to the subject at the altered infusion rate or infusion rates upon receipt of the infusion rate or infusion rates; and g) repeating steps b)-f) at set time intervals.

In some embodiments, the disclosure provides a method for fluid resuscitation and/or cardiovascular drug administration clinical decision support comprising: a) asking a user to provide an initial infusion rate of a fluid and/or a cardiovascular drug; b) receiving hemodynamic sensor data of the subject from at least one medical monitoring device attached to the subject by a hierarchical control architecture system, wherein the hierarchical control architecture system comprises: at least one adaptive controller; and a logic-based controller; wherein the subject's hemodynamic data is received by the logic-based controller and the at least one adaptive controller, wherein the at least one adaptive controller and the logic-based controller are in communication with one another; c) generating by the at least one adaptive controller an altered infusion rate based on the subject's hemodynamic data, previous infusion rates, and internal parameters and states of the at least one adaptive controller; d) verifying by the logic-based controller that the hemodynamic data and the at least one adaptive controller states do not violate rules governing the operation of the at least one adaptive controller; e) verifying by the logic-based controller whether the altered infusion rate meets the requirements to notify the user and if not the infusion rate is kept at the previous value; f) displaying the altered infusion rate from the at least one adaptive controller if the altered infusion rate meets the requirement in step e); g) asking the user to either accept the altered infusion rate or change the new infusion rate to a different value or different values; and h) repeating steps b)-g) at set time intervals.

In embodiments, this disclosure provides for a clinical decision support (semi-automated) system for notifying a user through audio-visual alarms if certain infusion therapy performance criteria are violated. A notification can be issued by a higher-level logic-based controller. In some embodiments, the notification asks the user to change the therapy type from one type to another. For example, in some embodiments, if the subject was being administered with fluid, the user can be asked to consider administering a vasopressor.

In another embodiment, this disclosure provides for a clinical decision support system for issuing a prompt when a change in infusion therapy is implicated based at least on a background infusion rate. An appropriate notification message and/or an appropriate change in infusion therapy recommendation message may be determined. Further, the appropriate notification message and/or the appropriate recommendation message may be displayed.

In another embodiment, this disclosure provides for an apparatus for displaying infusion therapy information which can be used to optimize infusion therapy. The apparatus comprises a memory, a display, and a processor in operable communication with the memory and the display. The display displays at least one appropriate notification message and appropriate change in infusion therapy recommendation when the processor issues the notification message and/or the recommendation message upon implication for a change in infusion therapy based at least on an active infusion rate stored in memory and a background infusion rate. In some embodiments, the background infusion rate is calculated by a lower-level controller based at least on received sensor measurement from a hemodynamic monitoring device.

DETAILED DESCRIPTION

Figure 1A:
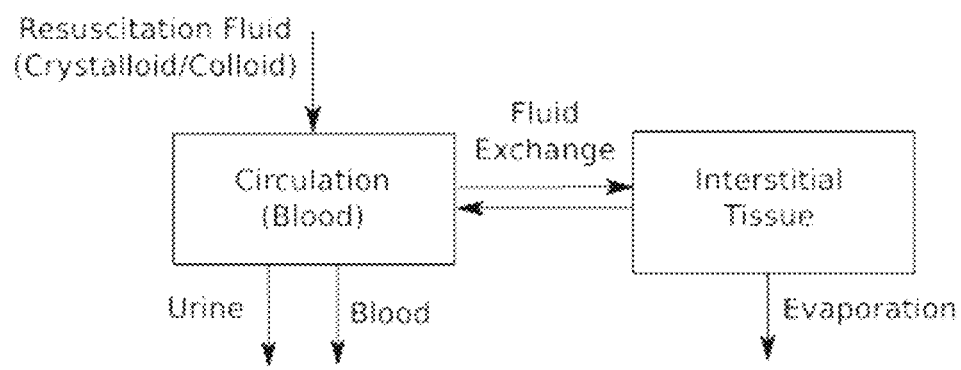
FIG. 1A is a diagram that illustrates a two-compartment model of fluid exchange in the body for non-burn patients.

Reliable and consistent fluid resuscitation (i.e., intravenous administration of fluids) is critical for perioperative and intensive care unit (ICU) fluid management in human and animal populations. Fluid management is required for surgical patients as well as patients suffering from hypovolemia, sepsis, severe sepsis, septic shock, burn, and other conditions. The goal of fluid resuscitation is to restore blood volume in the circulatory system to an acceptable level in order to ensure adequate tissue perfusion (i.e., blood delivery to tissue). However, large intra-patient and inter-patient variability in physiological parameters, and the effects of different illnesses and medications can result in under-resuscitation and over-resuscitation of patients.

Under-resuscitation results in hypovolemia, which can lead to hypoperfusion and organ failure. Over-resuscitation results in fluid overload, which can lead to complications such as pulmonary edema. Fluid overload is associated with higher rates of morbidity and mortality. Restrictive fluid resuscitation protocols reduce the number of mechanical ventilation days and the length of hospital stays.

Cardiovascular drug administration can be used independently to address a clinical condition (e.g., vasopressors are used to increase blood pressure to a clinically acceptable value or inotropic agents are used to change the contractility of the heart). Cardiovascular drugs, such as vasopressors, are administered independent of fluids in critical care for hypotensive patients. Cardiovascular drugs can also be used in combination with fluid resuscitation. For example, to address hypotension and hypovolemia in sepsis and during surgery, a vasopressor and fluid can be administered simultaneously.

The present disclosure describes a reliable and consistent closed-loop fluid resuscitation system, a clinical decision support fluid resuscitation system, a closed-loop cardiovascular drug administration system, a clinical decision support cardiovascular drug administration system, a closed-loop fluid and cardiovascular drug administration system, and a clinical decision support fluid and cardiovascular drug administration system. The system uses continuous measurements from standard operating room (OR) or ICU hemodynamic monitoring devices or sensors or a built-in or add-on modules to measure such continuous measures to compute the required fluid and/or cardiovascular drug infusion rates for patients receiving continuous infusion. Adaptive control architecture is used to compute the required infusion rates to regulate an endpoint of fluid or drug administration including, but not limited to, static indicators of fluid responsiveness and dynamic indicators of fluid responsiveness for the fluid resuscitation module, and hemodynamic measures for the cardiovascular drug administration module. In some embodiments, the static indicators of fluid responsiveness include mean arterial pressure, central venous pressure, heart rates, cardiac output, stroke volume, cardiac index, and urine output rates of patients. In some embodiments, dynamic indicators of fluid responsiveness include stroke volume variation, pulse pressure variations, systolic pressure variation, dynamic arterial elastance, and pleth variability indices of patients. In some embodiments, hemodynamic measures include mean arterial pressure, central venous pressure, systolic pressure, diastolic pressure, heart rate, cardiac output, cardiac index, systemic vascular resistance, stroke volume, and urine output. The closed-loop fluid resuscitation and/or cardiovascular drug administration system described herein comprises an adaptive controller or two adaptive controllers that use a function approximator, such as a neural network, Fourier functions, or wavelets, to identify the unknown dynamics and physiological parameters of a patient to compute appropriate infusion rates and to regulate the endpoint of fluid resuscitation or cardiovascular drug administration.

The developed fluid resuscitation system can use either crystalloids or colloids during resuscitation and use vasoactive cardiovascular drugs (e.g., vasopressor) or inotropic agents. The fluid infusion rate (e.g., in mL/hour) is highly dependent on a patient needs. In some embodiments, the fluid infusion rate can range from 0 to 3,000 mL/hr or more in humans, and 0 to 40,000 mL/h or more in animals. The cardiovascular drug infusion rate (e.g., in mcg/kg/min) is highly dependent on a patient's needs. In some embodiments, the cardiovascular drug infusion rate (e.g., vasopressor or inotropic agents) can range from 0 mcg/kg/min to 40 mcg/kg/min, or can exceed 40 mcg/kg/min.

Any method or algorithm described herein can be embodied in software or set of computer-executable instructions capable of being run on a computing device or devices. The computing device or devices can include one or more processor (CPU) and a computer memory. The computer memory can be or include a non-transitory computer storage media such as RAM which stores the set of computer-executable (also known herein as computer readable) instructions (software) for instructing the processor(s) to carry out any of the algorithms, methods, or routines described in this disclosure. As used in the context of this disclosure, a non-transitory computer-readable medium (or media) can include any kind of computer memory, including magnetic storage media, optical storage media, nonvolatile memory storage media, and volatile memory. Non-limiting examples of non-transitory computer-readable storage media include floppy disks, magnetic tape, conventional hard disks, CD-ROM, DVD-ROM, BLU-RAY, Flash ROM, memory cards, optical drives, solid state drives, flash drives, erasable programmable read only memory (EPROM), electrically erasable programmable read-only memory (EEPROM), non-volatile ROM, and RAM. The computer-readable instructions can be programmed in any suitable programming language, including JavaScript, C, C#, C++, Java, Python, Perl, Ruby, Swift, Visual Basic, and Objective C. Embodiments of the invention also include a non-transitory computer readable storage medium having any of the computer-executable instructions described herein.

A skilled artisan will further appreciate, in light of this disclosure, how the invention can be implemented, in addition to software and hardware, using one or more firmware. As such, embodiments of the invention can be implemented in a system which includes any combination of software, hardware, or firmware. In the context of this specification, the term "firmware" can include any software programmed onto the computing device, such as a device's nonvolatile memory. Thus, systems of the invention can also include, alternatively or in addition to the computer-executable instructions, various firmware modules configured to perform the algorithms of the invention.

According to embodiments, the computing device or devices can include a mainframe computer, web server, database server, desktop computer, laptop, tablet, netbook, notebook, personal digital assistant (PDA), gaming console, e-reader, smartphone, or smartwatch, which may include features such as a processor, memory, hard drive, graphics processing unit (GPU), and input/output devices such as display, keyboard, and mouse or trackpad (depending on the device). Embodiments can also provide a graphical user interface made available on one or more client computers. The graphical user interface can allow a user on a client computer remote access to the method or algorithm.

Additional embodiments of the invention can include a networked computer system for carrying out one or more methods of the invention. The computer system can include one or more computing devices which can include a processor for executing computer-executable instructions, one or more databases, a user interface, and a set of instructions (e.g. software) for carrying out one or more methods of the invention. According to other embodiments, the computing device or devices can be connected to a network through any suitable network protocol such as IP, TCP/IP, UDP, or ICMP, such as in a client-server configuration and one or more database servers. The network can use any suitable network protocol and can be any suitable wired or wireless network including any local area network, wide area network, Internet network, telecommunications network, Wi-Fi enabled network, or Bluetooth enabled network.

Compartmental Modeling for Characterizing Fluid Distribution

The present disclosure models the microvascular exchange system to characterize the distribution of fluids in the body.

A two-compartment dynamic system model is used for all patient populations except for patients with burn injuries. The compartments for two-compartment dynamic system models include circulation (blood) and interstitial tissue. A 4th-order nonlinear state space model representation of the dynamic system can provide a simplified model of the microvascular exchange system for non-burn patients. The states of the two-compartment dynamic system include the volume of fluids and albumin mass in each compartment (a total of four states).

A three-compartment model is used for patients with burn injuries. The states of the three-compartment dynamic system model include circulation (blood), injured tissue, and uninjured tissue. A 6th-order nonlinear state space model representation of the dynamic system can provide a simplified model of the microvascular exchange system for burn patients. The states of the three-compartment dynamic system include volume of fluids and albumin mass in each compartment (a total of six states).

The parameters of the two- and three-compartment models of the microvascular exchange system characterize fluid and mass exchange between different compartments. These parameters are generally unknown and are different from patient to patient.

Figure 1B:
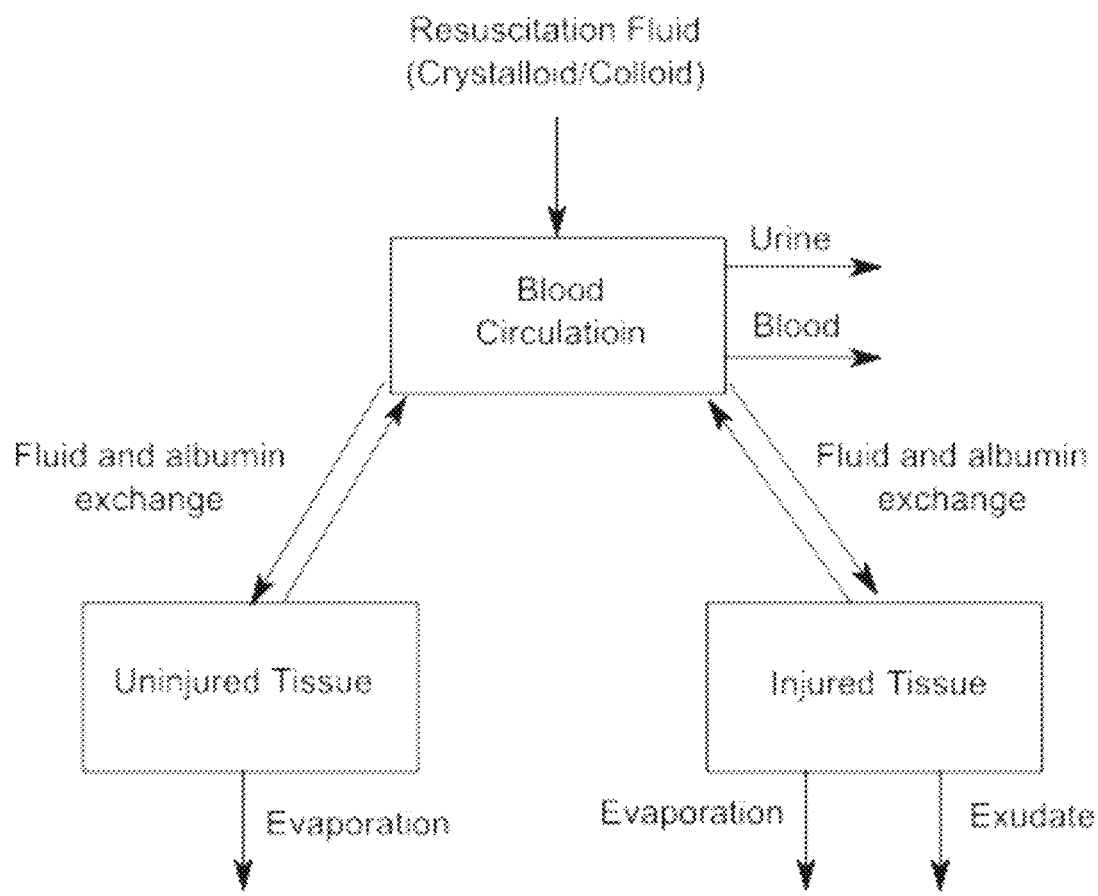
FIG. 1B is a diagram that illustrates a three-compartment model of the microvascular exchange system for burn patients.

FIG. 1A illustrates a two-compartment model of the fluid exchange in the body for non-burn patients. FIG. 1B illustrates a three-compartment model of the microvascular exchange system for burn patients.

In some embodiments, a higher number of compartments are used to model the microvascular exchange system of a patient population. In some embodiments, a model dynamic system consists of 2, 3, 4, or 5 compartments. In some embodiments, a 1, 2, 3, or 4-compartment dynamic system model is used for a patient population. In some embodiments, a two-compartment dynamic system model is used for a patient population. In some embodiments, a three-compartment dynamic system model is used for a patient population. In some embodiments, a four-compartment dynamic system model is used for a patient population.

Compartmental Modeling for Characterizing Cardiovascular Drug Distribution

The present disclosure models the cardiovascular drug distribution in the body using a compartmental model.

Cardiovascular drug distribution can be modeled using a two-compartment model. The compartments for two-compartment dynamic system models include circulation (blood) and tissue. A 2nd-order nonlinear state space model representation of the dynamic system can provide a simplified model of the cardiovascular drug distribution for patients. The states of the two-compartment dynamic system include the concentration of cardiovascular drug in each compartment.

Figure 1C:
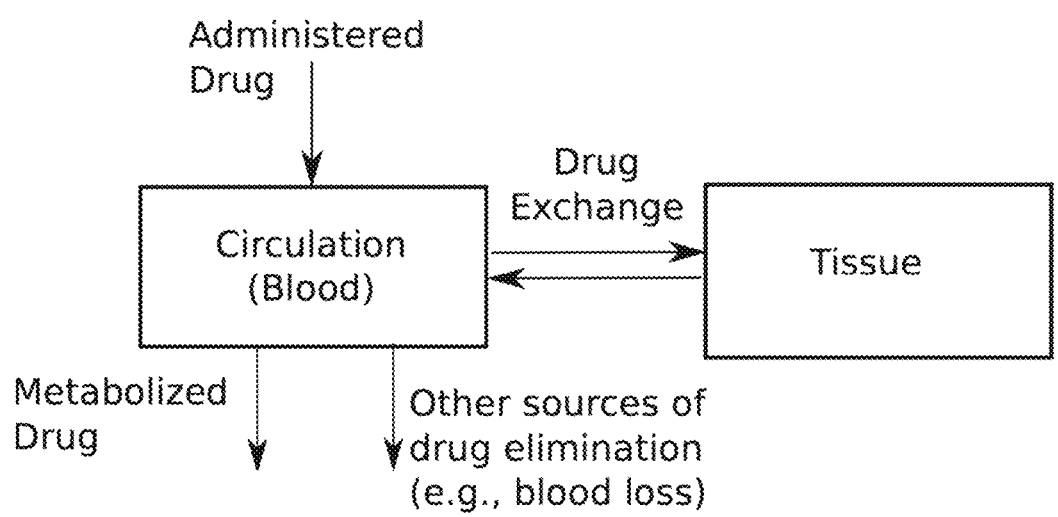
FIG. 1C is a diagram that illustrates a two-compartment model of cardiovascular drug exchange in the body.

The parameters of the two-compartment model of the cardiovascular drug distribution characterizes cardiovascular drug mass exchange between different compartments. These parameters are generally unknown and are different from patient to patient. FIG. 1C illustrates a two-compartment model of the cardiovascular drug distribution in the body.

In some embodiments, a higher number of compartments are used to model the cardiovascular drug distribution for a patient. In some embodiments, a model dynamic system consists of 2, 3, 4, or 5 compartments. In some embodiments, a 1, 2, 3, or 4-compartment dynamic system model is used for a patient population. In some embodiments, a two-compartment dynamic system model is used for a patient population. In some embodiments, a three-compartment dynamic system model is used for a patient population. In some embodiments, a four-compartment dynamic system model is used for a patient population.

Process for Computing Fluid Infusion Rate and/or Cardiovascular Drug Infusion Rate for a Closed-Loop System or a Clinical Decision Support System The disclosure provides an adaptive control architecture framework for a closed-loop fluid resuscitation and/or cardiovascular drug administration system. The fluid resuscitation and/or cardiovascular drug administration system of the disclosure receives data from a monitoring system or a set of monitoring systems. In some embodiments, the fluid resuscitation and/or cardiovascular drug administration system receives data from an existing monitoring system or systems. In some embodiments, the fluid resuscitation and/or cardiovascular drug administration system receives data from a built-in monitoring system or systems. In some embodiments, the fluid resuscitation and/or cardiovascular drug administration system receives data from an add-on monitoring system or systems.

The received data comprises one of: blood pressure, heart rate, stroke volume variation, pulse pressure variation, dynamic arterial elastance, pleth variability index, urine output rate, systolic pressure variation, central venous pressure, mean arterial pressure, cardiac output, cardiac index, systolic pressure, diastolic pressure, systemic vascular resistance, or stroke volume. In some embodiments, the received data comprises a combination of blood pressure, heart rate, stroke volume variation, pulse pressure variation, dynamic arterial elastance, pleth variability index, urine output rate or urine output, systolic pressure variation, central venous pressure, mean arterial pressure, cardiac output, cardiac index, systolic pressure, diastolic pressure, systemic vascular resistance, or stroke volume. In some embodiments, a built-in or add-on monitoring system or systems are used and the input data includes one or a combination of an invasive blood pressure signal or a non-invasive pressure signal collected from a patient's arm or leg using a blood pressure cuff.

The disclosed fluid resuscitation and/or cardiovascular drug administration system can transmit data to a receiver or a set of receivers. In some embodiments, the disclosed fluid resuscitation and/or cardiovascular drug administration system can transmit data to an external or built-in infusion pump or infusion pumps, a user, an electronic medical record, or a remote location. In some embodiments, the disclosed fluid resuscitation and/or cardiovascular drug administration system can transmit data to a combination of receivers. In some embodiments, the disclosed fluid resuscitation and/or cardiovascular drug administration system can transmit data to an infusion pump or infusion pumps and a user or users. In some embodiments, the disclosed fluid resuscitation system can transmit data to an infusion pump or infusion pumps, a user or users, and an electric medical record. In some embodiments, the disclosed fluid resuscitation system can transmit data to an infusion pump or infusion pumps, a user or users, an electronic medical record, and a remote location.

The adaptive architecture of the disclosure can be implemented in a fully automated architecture or a partially automated architecture.

Full automation: In some embodiments, the adaptive architecture of the disclosure is implemented in a fully automated architecture, wherein the infusion rate of the infusion pump or infusion rates of the infusion pumps are updated automatically by the system using the most recent value of the infusion rate or infusion rates.

Partial automation (also referred to as clinical decision support): In some embodiments, the adaptive architecture of the disclosure is implemented in a partially automated architecture. In some embodiments, the framework of the disclosure is used within a clinical decision support context, where recommended infusion rates are displayed to the end-user (clinician) for approval. In some embodiments, the system can request for approval before changing the infusion rate of the pump or pumps. In some embodiments, the end-user can use recommended infusion rate changes and manually change the infusion rate on the pump or pumps based on his/her clinical judgment and the recommendation provided by the clinical decision support system. In some embodiments, the end-user can enter whether the recommended infusion rate was accepted or rejected. In some embodiments, the end-user can enter a new manually changed infusion rate or infusion rates. In some embodiments, the system can automatically change the infusion rate of the pump or infusion rates of the pump after the user approves or modifies the recommended infusion rate or infusion rates.

Architecture of the Disclosure

The present disclosure is able to determine suitable infusion rates based on an input from patient-monitoring devices, built-in monitoring devices, add-on monitoring modules, or sensors. Infusion rates can be adjusted based on the input from patient-monitoring devices, built-in monitoring devices, add-on monitoring modules, or sensors. The adaptive control framework of the disclosure does not require any patient-specific information (e.g., age, gender, weight, diagnosis). Furthermore, the framework does not require an accurate model of the patient dynamics and the patient-specific physiological parameters.

The present disclosure describes a closed-loop or clinical decision support fluid resuscitation and/or cardiovascular drug administration system predicated on hierarchical adaptive control architecture. In some embodiments, the hierarchical control architecture is composed of one or two lower-level adaptive controllers and a higher-level, logic-based controller. In some embodiments, the higher-level, logic-based controller is a rule-based expert system.

If the system is used for fluid resuscitation, the hierarchical control architecture is composed of an adaptive controller fluid module and a higher-level, logic-based controller. If the system is used for only cardiovascular drug administration, the hierarchical control architecture is composed of an adaptive controller cardiovascular drug module and a higher-level, logic-based controller. If the system is used for fluid resuscitation and cardiovascular drug administration, the hierarchical control architecture is composed of an adaptive controller fluid module, an adaptive controller cardiovascular drug module, and a higher-level, logic-based controller.

The lower-level controller focused on fluid resuscitation uses an adaptive control framework to regulate a measure of fluid responsiveness to a desired value by adjusting the fluid infusion rate. In some embodiments, the lower-level controller can regulate mean arterial pressure, systolic pressure, diastolic pressure or a measure of fluid responsiveness including stroke volume variation, pleth variability index, pulse pressure variation, dynamic arterial elastance, central venous pressure, urine output rate or urine output, or systolic pressure variation. While the goal of this lower-level controller is to regulate a measure of fluid responsiveness to a desired value, the controller may achieve a measurement that is close to the desired value (with some error). Lower-level controller design parameters can be changed to adjust the value of this error.

The lower-level controller focused on cardiovascular drug administration uses an adaptive control framework to regulate a hemodynamic measure to a desired value by adjusting the cardiovascular drug infusion rate. In some embodiments, the lower-level controller can regulate mean arterial pressure, systolic pressure, diastolic pressure, heart rate, cardiac output, stroke volume, systemic vascular resistance, or cardiac index. In some embodiments the administered cardiovascular drug is a vasopressor and the lower-level controller can regulate mean arterial pressure, systolic pressure, systemic vascular resistance, or diastolic pressure. In some embodiments, the administered cardiovascular drug is an inotropic agent and the lower-level controller can regulate cardiac output, cardiac index, mean arterial pressure, systemic vascular resistance, or heart rate. In some embodiments, the administered cardiovascular drug is a chronotropic agent, and the lower-level controller can regulate heart rate or cardiac output. While the goal of this lower-level controller is to regulate a hemodynamic measure to a desired value, the controller may achieve a measurement that is close to the desired value (with some error). Lower-level controller design parameters can be changed to adjust the value of this error.

The role of the higher-level, logic-based controller is different depending on whether the system is used to fully automate or partially automate fluid resuscitation and/or cardiovascular drug administration. The higher-level, logic-based controller monitors the performance of the lower-level adaptive controller(s) and the patient's response to therapy. In case of fluid management, a measure of fluid responsiveness or tissue perfusion is monitored (e.g., mean arterial pressure, stroke volume variation, pulse pressure variation, systolic pressure variation, dynamic arterial elastance, pleth variability index etc.) and in case of cardiovascular drug administration, a measure of hemodynamic function is monitored (e.g., mean arterial pressure, heart rate etc.). If certain performance criteria are violated, then the higher-level controller can "disengage" the lower-level controller(s) (if the system is used for full automation of fluid resuscitation) or the higher-level controller will stop providing suggested infusion rates and will alert the end-user (if the system is used for partial automation of fluid resuscitation). Time stamps, infusion rates and measurement data can be sent to an internal or external database by the higher-level controller for archiving purposes.

The higher-level controller can also determine the timing of engaging each lower-level controller. In some embodiments, the higher-level controller engages the fluid resuscitation module first, and if some performance criteria is not met after a period of time, the drug administration module is also engaged. The higher-level controller (in clinical decision support) can also determine the when to notify the user. In some embodiments, the higher-level controller notifies the user only if the difference between the newly computed infusion rate by the lower-level controller and the last user-approved infusion rate is higher than some threshold.

In some embodiments, in a partial automation application, the higher-level controller can use end-user response (to accept or reject the suggested infusion rate) to update the internal state of the lower-level controller. In addition, in both full automation and partial automation, the higher-level controller can change the internal states of the lower-level controller(s) if the computed infusion rate is out of a "safe" range defined by the end-user. In some embodiments, if the infusion rate computed by the lower-level controller exceeds the maximum allowable infusion rate then the higher-level controller resets the internal parameters and variables of the controller to preset default values.

The higher-level controller can also provide recommendation to the user to engage the cardiovascular drug administration module if a patient's hemodynamic variable of interest is not improved after a certain period of time after fluid resuscitation. In some embodiments, the higher-level controller asks the user to engage the fluid resuscitation module first, and if some performance criteria is not met after a period of time, asks the user to engage the drug administration module. In some embodiments, the higher-level controller asks the user to engage the cardiovascular drug administration module first, and if some performance criteria is not met after a period of time, asks the user to engage the fluid resuscitation module.

Figure 2A:
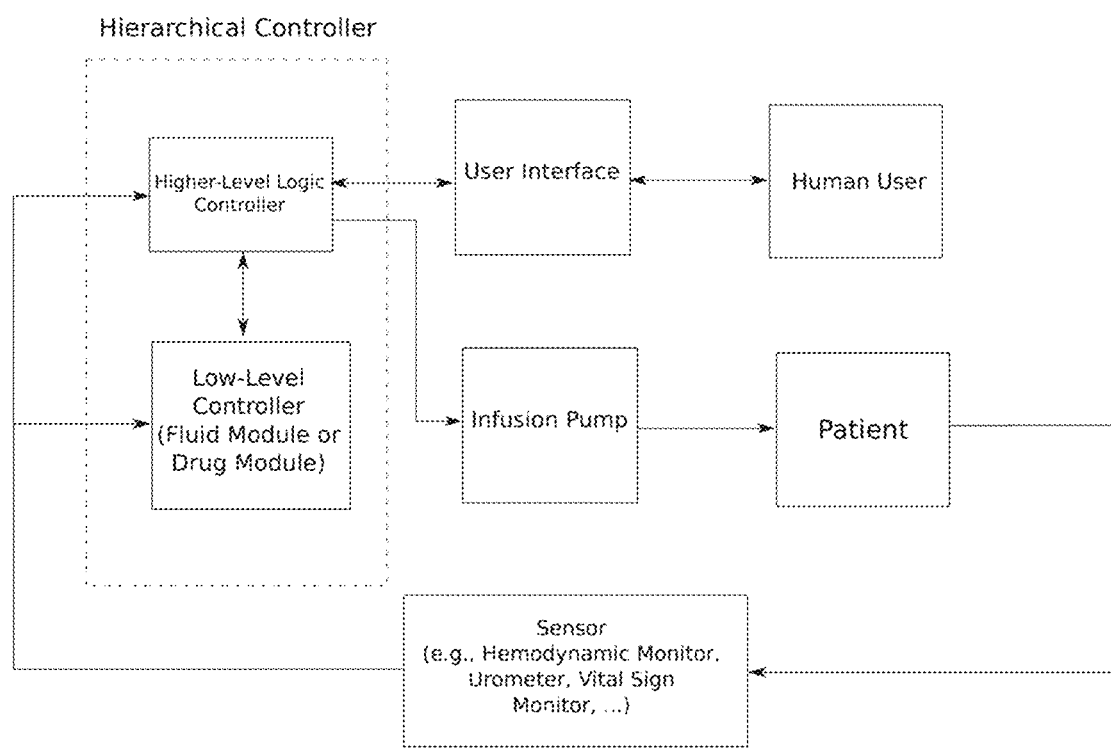
FIG. 2A is a diagram that illustrates the overall architecture of a fully automated closed-loop fluid resuscitation or cardiovascular drug administration system.

FIG. 2A illustrates the overall architecture of a fully automated closed-loop fluid resuscitation system or a fully automated closed-loop cardiovascular drug administration system of the disclosure. A sensor (e.g., hemodynamic monitor) sends data to the lower-level controller and the higher-level controller. The higher-level controller monitors the performance of the lower-level controller and the response of the patient to fluids or cardiovascular drugs by monitoring measurements from the sensor, internal state of the lower-level controller, and infusion rate computed by the lower-level controller (which is sent to the infusion pump by the higher-level controller). The lower-level controller can send or receive data from the higher-level logic controller.

The higher-level controller can send or receive data from the lower-level controller. The human user (clinician) can interact with the closed-loop system through a user interface to set a target value for the measurement (e.g., set target stroke volume variation of 13% or set mean arterial pressure of 65 mmHg), set the range of "safe" infusion rates (e.g., between 0 and 3,000 mL/hr for fluids or 0 and 0.5 mcg/kg/min for a vasopressor), start and stop the system, or set a backup infusion rate in case of loss of sensor signal (e.g., 1,000 mL/hr for fluid or 0.2 mcg/kg/min for vasopressor). The lower-level controller processes a patient's data received from a sensor or a hemodynamic monitoring device (external or built-in), and sends computed infusion rates to the higher-level controller. The higher-level controller ensures that the infusion rate meets all requirements (e.g., it is in the safe range) and if so sends a command to an infusion pump (external or built-in), which administers fluids or cardiovascular drugs to the patient.

Figure 2B:
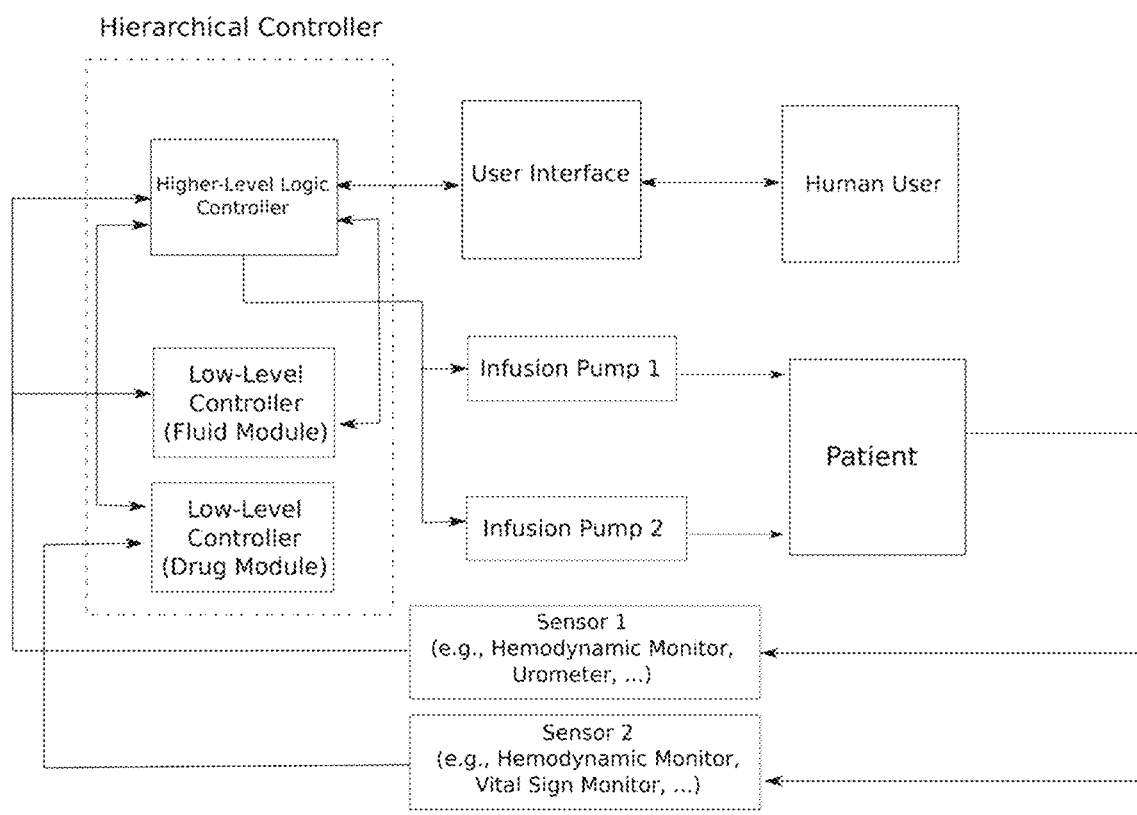
FIG. 2B is a diagram that illustrates the overall architecture of a fully automated closed-loop fluid resuscitation and cardiovascular drug administration system.

FIG. 2B illustrates the overall architecture of a fully automated closed-loop fluid resuscitation system and cardiovascular drug administration system of the disclosure. In this system, the closed-loop system provides both fluid and cardiovascular drug simultaneously. One or two sensors (e.g., hemodynamic monitor and vital sign monitor) send data to the lower-level controller fluid module and lower-level controller cardiovascular drug module and the higher-level controller. The higher-level controller monitors the performance of the lower-level controllers and the response of the patient to fluid and cardiovascular drug by monitoring measurements from the sensors, internal state of the lower-level controllers, and infusion rates computed by the lower-level controllers (which are sent to two different infusion pumps by the higher-level controller: a fluid infusion pump and a cardiovascular drug infusion pump). Lower-level controllers can send or receive data from the higher-level logic controller.

The higher-level controller can send or receive data from the lower-level controllers. The human user (clinician) can interact with the closed-loop system through a user interface to set a target value for the measurement or measurements (e.g., set target stroke volume variation of 13% and mean arterial pressure of 65 mmHg), set the range of "safe" infusion rates (e.g., between 0 and 3,000 mL/hr for fluids and 0 and 0.5 mcg/kg/min for a vasopressor), start and stop the system, or set a backup infusion rate in case of loss of sensor signal (e.g., 1,000 mL/hr for fluid and 0.2 mcg/kg/min for vasopressor). The lower-level controllers process patient's data received from one or more sensors or a hemodynamic monitoring devices (external or built-in), and sends computed infusion rates to the higher-level controller. The higher-level controller ensures that the infusion rate meets all requirements (e.g., they are in the safe range) and if so sends a commands to infusion pumps (external or built-in), which administer fluids and cardiovascular drugs to the patient. Data measured from sensors used by the lower-level fluid module and lower-level cardiovascular drug administration module may be the same (e.g., mean arterial pressure for both modules) or different (e.g., stroke volume variation for fluid module and mean arterial pressure for cardiovascular drug module).

Figure 3A:
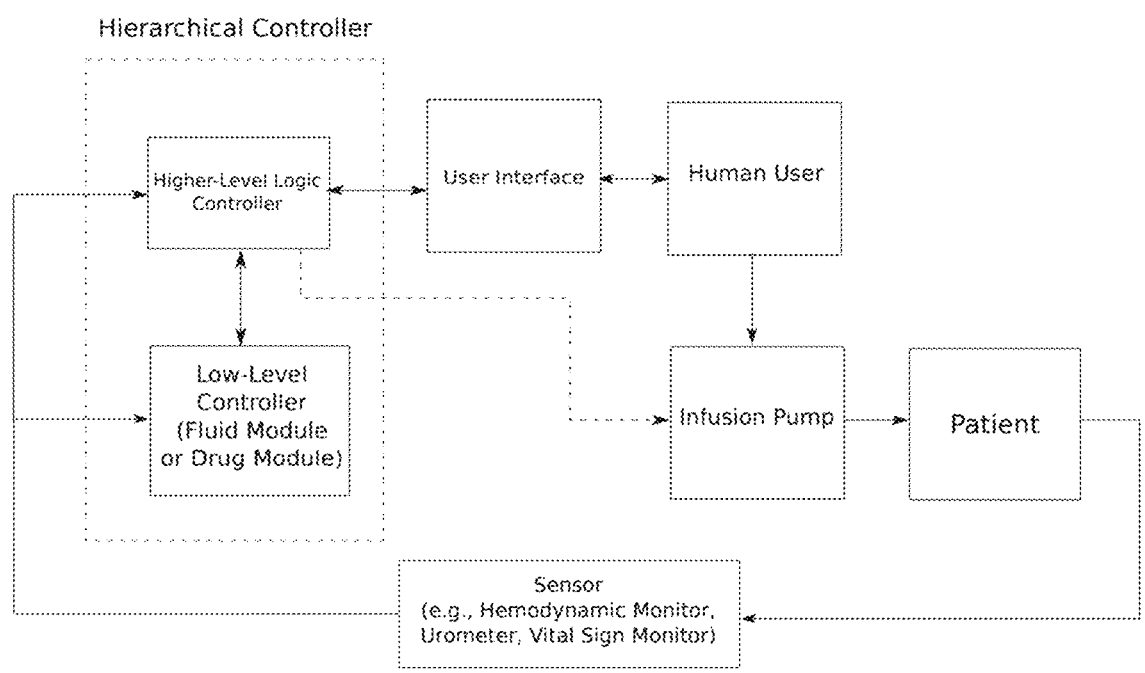
FIG. 3A is a diagram that illustrates the overall architecture of a partially automated (clinical decision support) fluid resuscitation or cardiovascular drug administration system.

FIG. 3A illustrates the overall architecture of a partially automated (clinical decision support) fluid resuscitation or cardiovascular drug administration system of the disclosure. A monitoring device or sensor (e.g., hemodynamic monitor, vital sign monitor, urometer, etc.) sends data to the lower-level controller and the higher-level controller. The higher-level controller monitors the performance of the lower-level controller and the response of the patient to fluids or cardiovascular drugs by monitoring measurements from the sensor, internal state of the lower-level controller, and infusion rate computed by the lower-level controller and the action taken by the human user (clinician). The lower-level controller can send or receive data from the higher-level logic controller. The higher-level controller can send or receive data from the lower-level controller.

The human user can interact with the partially automated (clinical decision support) system through a user interface to set a target value for the measurement (e.g., set target stroke volume variation of 13% or set target mean arterial pressure of 65 mmHg), set the range of "safe" infusion rates (e.g., between 0 and 3,000 mL/hr for fluid or 0 to 0.5 mcg/kg/min for vasopressor), and start and stop the system. The lower-level controller can process a patient's data received from a sensor or a hemodynamic monitoring device (external or built-in), and send recommended infusion rates to the user interface to be displayed. The human user can then either accept or change the recommended rate to an acceptable value. The human user can then manually change the infusion rate on the pump (if pump is not built-in or a pump that is not connected to the system by wire or wireless connection) or instruct the system to change the infusion rate (for built-in or a pump that is connected to the system by wire or wireless connection).

Figure 3B:
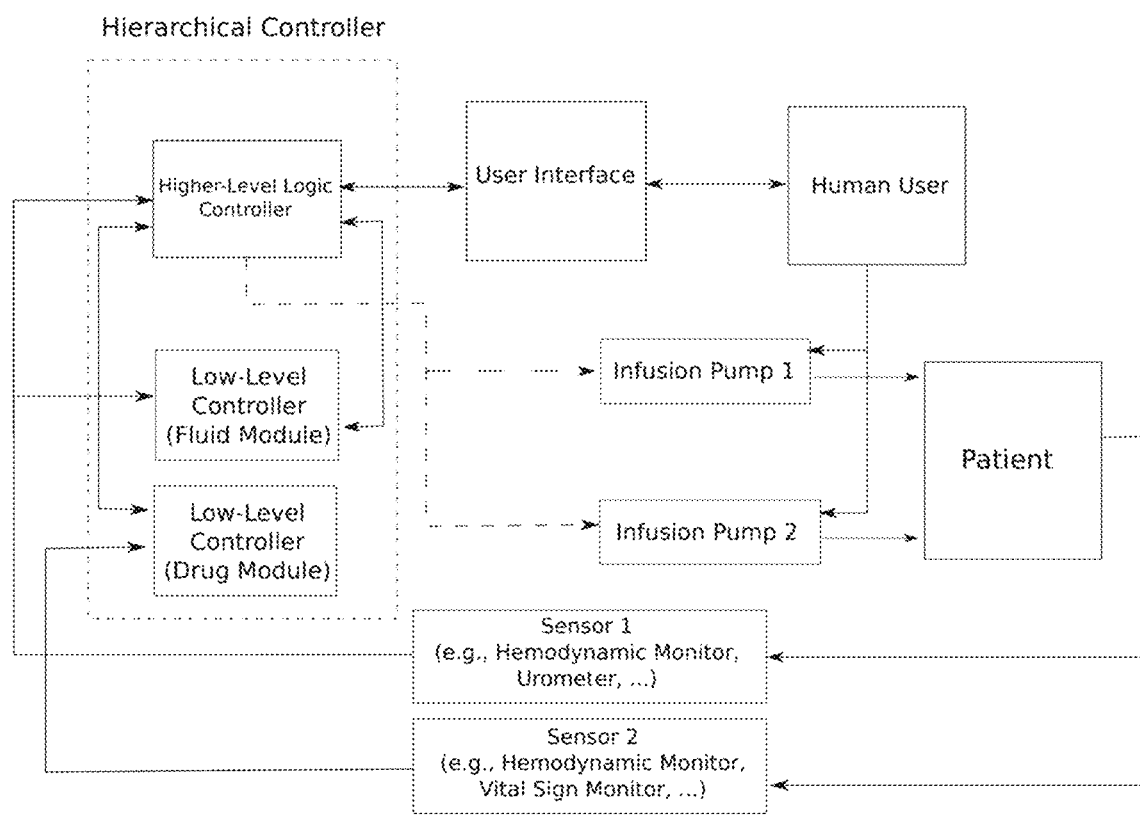
FIG. 3B is a diagram that illustrates the overall architecture of a partially automated (clinical decision support) fluid resuscitation and cardiovascular drug administration system.

FIG. 3B illustrates the overall architecture of a partially automated (clinical decision support) fluid resuscitation and cardiovascular drug administration system of the disclosure. In this architecture fluid and cardiovascular drug is administered simultaneously. A monitoring device or sensor or two monitoring devices and sensors (e.g., hemodynamic monitor, vital sign monitor, urometer) sends data to the lower-level controller fluid module and a lower-level controller cardiovascular drug module and the higher-level controller. The higher-level controller monitors the performance of the lower-level controllers and the response of the patient to fluids and cardiovascular drugs by monitoring measurements from the sensor or sensors, internal state of the lower-level controllers, and infusion rate computed by the lower-level controllers and the action taken by the human user (clinician). Lower-level controllers can send or receive data from the higher-level logic controller. The higher-level controller can send or receive data from the lower-level controllers.

The human user can interact with the partially automated (clinical decision support) system through a user interface to set a target value for the measurement or measurements (e.g., set target stroke volume variation of 13% and set target mean arterial pressure of 65 mmHg), set the range of "safe" infusion rates (e.g., between 0 and 3,000 mL/hr for fluid and 0 to 0.5 mcg/kg/min for vasopressor), and start and stop the system. Lower-level controllers can process patient's data received from one or more sensors or hemodynamic monitoring devices (external or built-in), and send recommended infusion rates to the user interface to be displayed. The human user can then either accept or change the recommended rate to an acceptable value. The human user can then manually change the infusion rate on the pump, if the pump is not built-in or a pump is not connected to the system by wire or wireless connection. The human user can also manually instruct the system to change the infusion rate for a built-in pump or a pump that is connected to the system by wire or wireless connection.

Figure 4A:
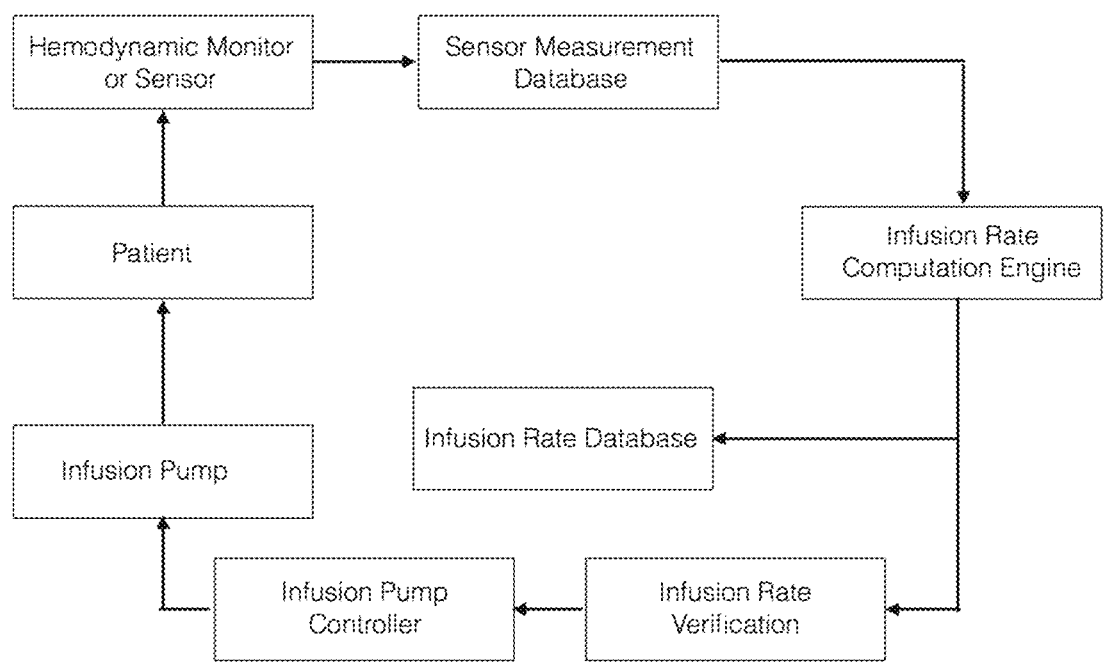
FIG. 4A is a diagram that illustrates components of a fully automated, closed-loop fluid resuscitation or cardiovascular drug administration system.

FIG. 4A illustrates components of a fully automated, closed-loop fluid resuscitation or cardiovascular drug administration system of the disclosure. A hemodynamic monitor or sensor sends a patient's data to a sensor measurement database. An infusion rate computation engine, which is embedded in the lower-level controller, retrieves sensor measurements and computes infusion rates. The infusion rates (and the corresponding sensor measurements) are communicated with an infusion rate database. The infusion rate computation engine can send data to the infusion rate database and an infusion rate verification system. The infusion rate verification system, which is embedded in the higher-level logic-based controller, ensures the computed rates meet the requirements and if acceptable sends the newly computed infusion rate to the infusion pump controller. The infusion pump controller then automatically changes the infusion rate of the infusion pump to administer an amount of fluid or cardiovascular drug based on commands received by the infusion pump controller.

Figure 4B:
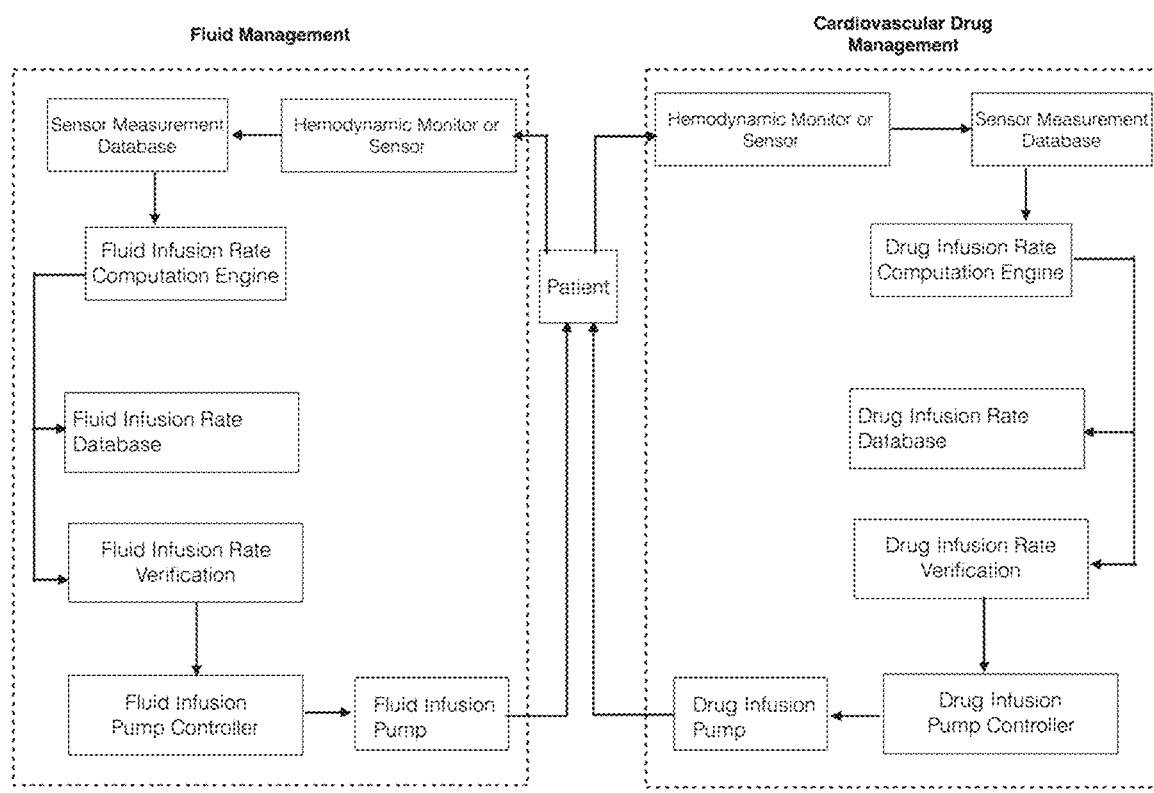
FIG. 4B is a diagram that illustrates components of a fully automated, closed-loop fluid resuscitation and cardiovascular drug administration system.

FIG. 4B illustrates components of a fully automated, closed-loop fluid resuscitation and cardiovascular drug administration system of the disclosure. The overall system is composed of two subsystems: a subsystem for fluid management and a subsystem for cardiovascular drug management. In each subsystem, a hemodynamic monitor or sensor sends a patient's data to a sensor measurement database. An infusion rate computation engine, which is embedded in the lower-level controller, retrieves sensor measurements and computes infusion rates. The infusion rates and the corresponding sensor measurements are communicated with an infusion rate database. The infusion rate computation engine can send data to the infusion rate database and an infusion rate verification system. The infusion rate verification system, which is embedded in the higher-level logic-based controller, ensures the computed rates meet the requirements and if acceptable sends the newly computed infusion rate to the infusion pump controller. The infusion pump controller then automatically changes the infusion rate of the infusion pump to administer an amount of fluid or cardiovascular drug based on commands received by the infusion pump controller.

Figure 5A:
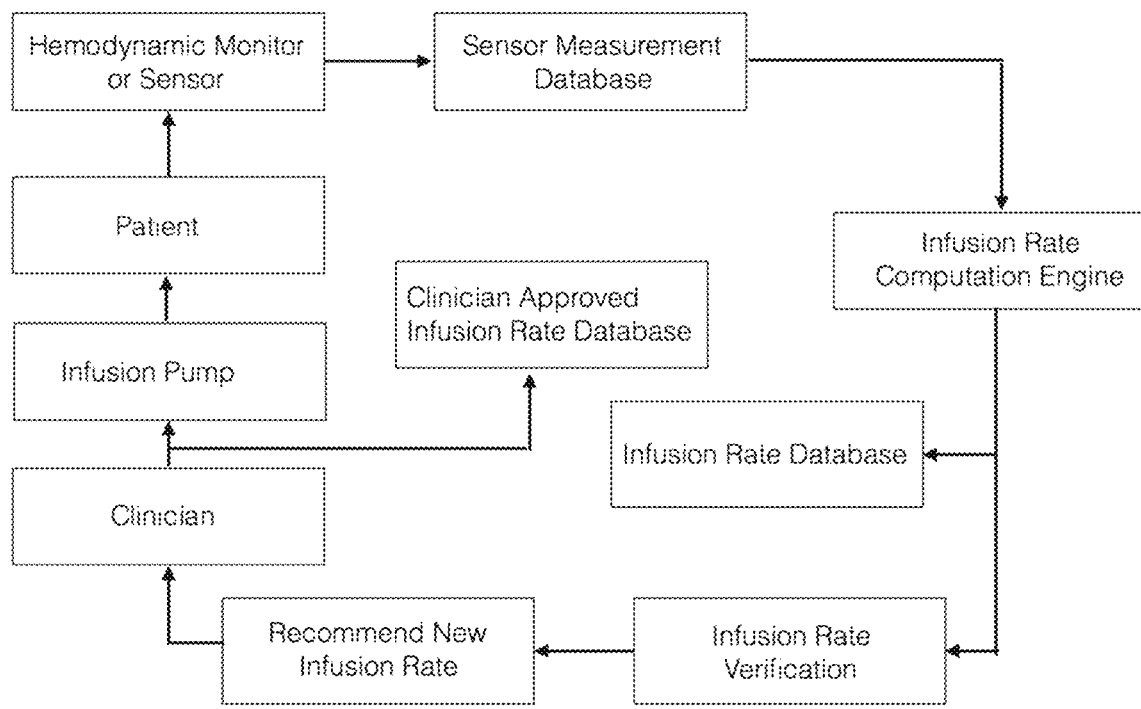
FIG. 5A is a diagram that illustrates components of a partially automated clinical decision support fluid resuscitation or cardiovascular drug administration system.

FIG. 5A illustrates components of a partially-automated clinical decision support fluid resuscitation or cardiovascular drug administration system of the disclosure. A hemodynamic monitor or sensor sends a patient's data to a sensor measurement database. An infusion rate computation engine, which is embedded in the lower-level controller, retrieves sensor measurements and computes infusion rates. The infusion rates and the corresponding sensor measurements are communicated with an infusion rate database. The infusion rate computation engine sends data to the infusion rate verification system, which is embedded in the higher-level logic-based controller. The infusion rate verification system ensures the computed rates meet the requirements including the requirement to notify the user of significant changes in infusion rate and if acceptable notifies the clinician using a user interface. The recommended new infusion rate is presented to the clinician, who either approves the recommended infusion rate or requests a modification of the rate based on the clinician's qualitative judgement. The approved or modified infusion rate is sent to a database archiving clinician approved infusion rates. The clinician administers the approved or modified fluid or cardiovascular drug by either changing the infusion rate manually, if a pump is not built-in or the pump is not connected to the system by wire or wireless connection. The clinician can also instruct the system to change the infusion rate to the approved value if a pump is built-in or a pump is connected to the system by wire or wireless connection.

Figure 5B:
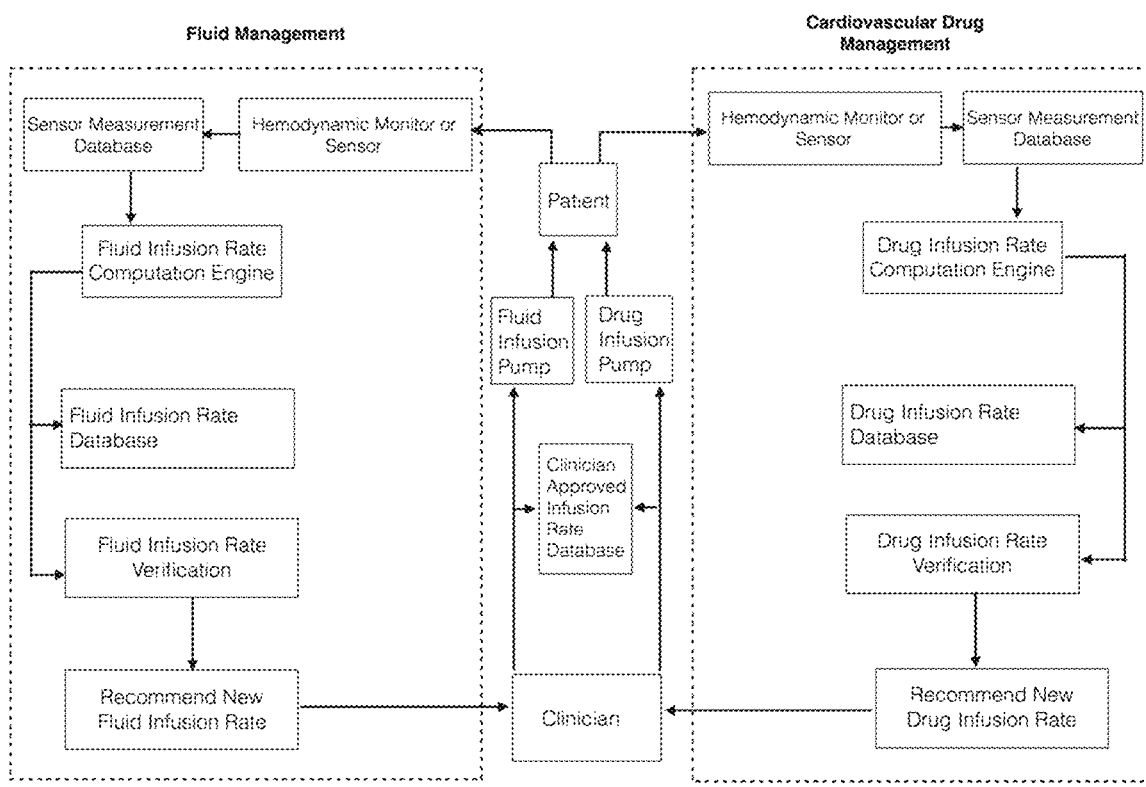
FIG. 5B is a diagram that illustrates components of a partially automated clinical decision support fluid resuscitation and cardiovascular drug administration system.

FIG. 5B illustrates components of a partially-automated clinical decision support fluid resuscitation and cardiovascular drug administration system of the disclosure. The overall system is composed of two subsystems: a subsystem for fluid management and a subsystem for cardiovascular drug management. In each subsystem, a hemodynamic monitor or sensor sends a patient's data to a sensor measurement database. An infusion rate computation engine retrieves sensor measurements and computes infusion rates. The infusion rates and the corresponding sensor measurements are communicated with an infusion rate database. The infusion rate computation engine, which is embedded in the lower-level controller, can send data to the infusion rate verification system. The infusion rate verification system, which is embedded in the higher-level logic-based controller, ensures the computed rates meet the requirements including the requirement to notify the user of significant changes in infusion rate and if acceptable notifies the clinician using a user interface. The recommended new infusion rates are presented to the clinician, who either approves the recommended infusion rates or requests a modification of the rates based on the clinician's qualitative judgement. The approved or modified infusion rates are sent to a database archiving clinician approved infusion rates. The clinician administers the approved or modified fluid and cardiovascular drug by changing the infusion rates manually if a pump is not built-in or a pump that is not connected to the system by wire or wireless connection. The clinician can also administer the approved or modified fluid and cardiovascular drug by instructing the system to change the infusion rates to the approved value if a pump is built-in or a pump is connected to the system by wire or wireless connection.

EXAMPLES

Example 1: Computing Fluid or Drug Infusion Rates Using Lower-Level Adaptive Control Architecture The present disclosure describes a process of computing the fluid or cardiovascular drug infusion rate using lower-level adaptive control architecture. The lower-level adaptive control architecture is applied to a problem involving only fluid administration, only cardiovascular administration, or fluid and cardiovascular drug administration. In the case of a combined fluid and cardiovascular drug administration, two lower-level adaptive controllers running in parallel are implemented to compute infusion rates for fluid and cardiovascular drug. The fluid or cardiovascular drug infusion rate is computed using lower-level adaptive control architecture through the following steps:

1) Select a sensor that can measure an endpoint for fluid or cardiovascular drug administration. For fluid administration, the endpoint includes variables such as stroke volume variation, pulse pressure variation, mean arterial pressure, dynamic arterial elastance, urine output rate, pleth variability index, dynamic arterial elastance, central venous pressure, systolic pressure, diastolic pressure, or systolic pressure variation. For cardiovascular drug administration, the endpoint includes variables such as mean arterial pressure, cardiac output, cardiac index, heart rate, systolic pressure, diastolic pressure, systemic vascular resistance, or central venous pressure. The values of the sensor are recorded and smoothed using window averaging or other noise reduction techniques. The measurements could be performed invasively or non-invasively.
2) The controller architecture assumes that a patient is modeled by an augmented dynamical system model consisting of a 2-, 3-, or n-compartment model (characterizing fluid or cardiovascular drug distribution), as well as a fictitious state. The fictitious state follows the same trend as of the fluid volume in circulation (in the case of fluid management) or cardiovascular drug mass in circulation (in the case of cardiovascular drug management) with some time lag.
3) A dynamic observer (estimator) is used to estimate deviation of the fictitious state and the fluid volume in circulation (in the case of fluid management) or cardiovascular drug mass in circulation (in the case of cardiovascular drug management) from steady state (equilibrium) values.
4) A function approximator (e.g., neural network or wavelets etc.) is used to approximate the unknown dynamics of the patient and the parameters of the patient, which are modeled by an augmented dynamical system.
5) The function approximator weights (or coefficients), sensor measurement values, and infusion rate computed by the adaptive controller at time $t-\Delta t$ are used to compute a new infusion rate. Alternatively, the function approximator weights (or coefficients), sensor measurement values, and infusion rate computed by the adaptive controller at times $t-\Delta t$ and $t-2\Delta t$ are used to compute a new infusion rate.
6) The new infusion rate is sent to higher level controller for further processing.
7) The function approximator weights (or coefficients) are updated using estimates provided by the dynamic observer, sensor measurement values, and the infusion rate computed by the adaptive controller at time $t-\Delta t$. Alternatively, the function approximator weights are updated using estimates provided by the dynamic observer, sensor measurement values, and the infusion rate computed by the adaptive controller at times $t-\Delta t$ and $t-2\Delta t$.
8) A delay of T seconds/minutes (e.g., 1 second, 10 seconds, 1 minute, 2 minutes, etc.) is introduced.
9) Step 3) is repeated to close the loop.

Figure 6:
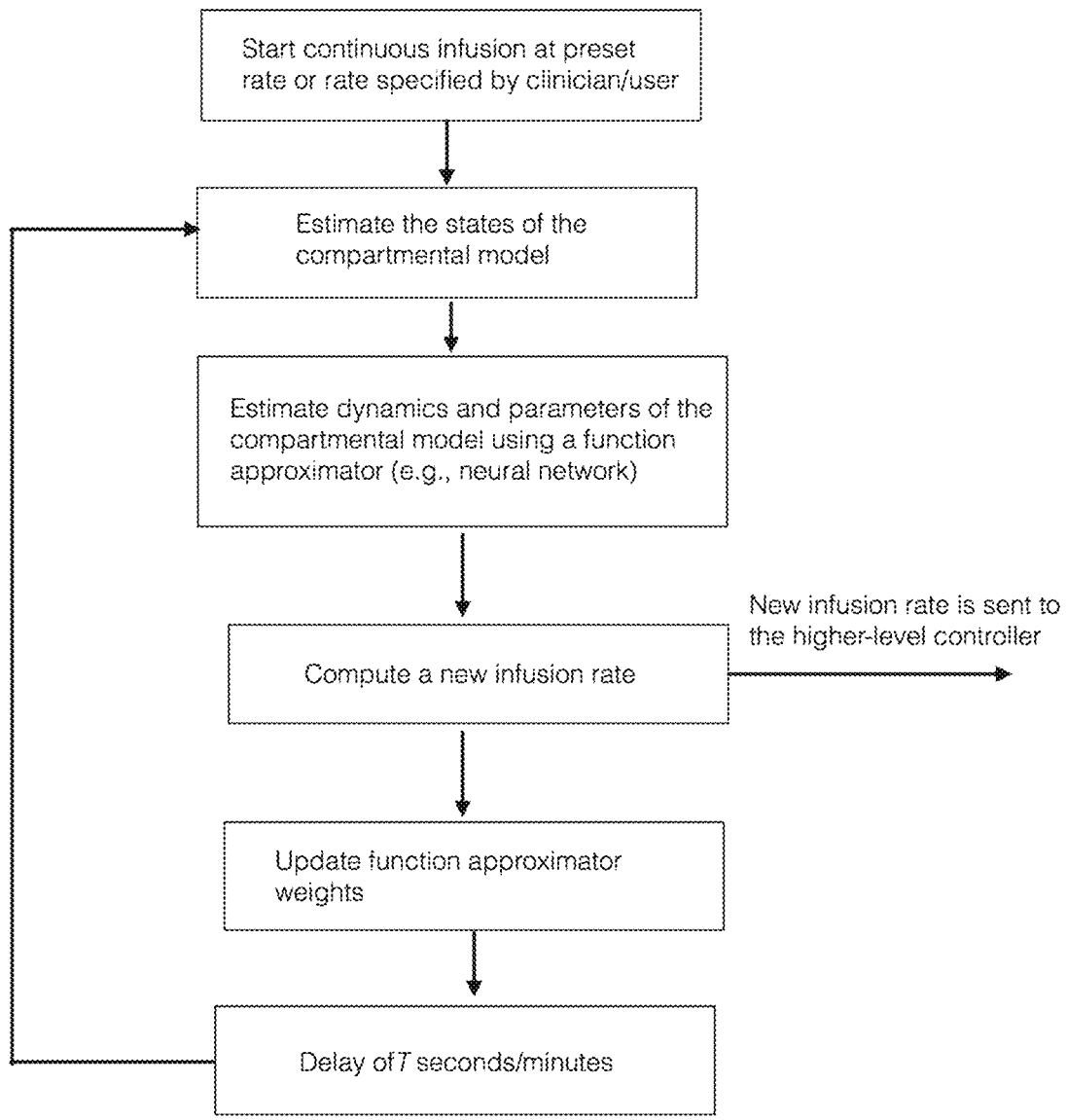
FIG. 6 is a flow chart that illustrates the lower-level adaptive control architecture according to embodiments.

FIG. 6 details a flow chart of the lower-level adaptive control architecture of the disclosure outlining steps 1)-9).

Example 2: Function Approximation for Modeling Unknown Dynamics and Patient Parameters for Fluid Distribution A two-compartment model is used to build the closed-loop fluid resuscitation architecture. The same approach is applied for compartmental models with 3 or more compartments.

A mass balance equation for a two-compartment dynamical system model is given by:

$$\dot{v}_c(t) = u(t) + J_L(t) - J_t(t) - J_{urine}(t) - J_{blood}(t), t \geq 0$$

$$\dot{a}_c(t) = Q_L - Q_t(t) - a_{blood}(t),$$

$$\dot{v}_t(t) = J_t(t) - J_L(t) - J_{evaporation}(t),$$

$$\dot{a}_t(t) = -Q_L(t) + Q_t,$$

where $u(t)$ is the rate of fluid infusion, $J_L(t)$ is the rate of volume transfer from interstitial tissue to circulation, $J_t(t)$ is the rate of volume transfer from circulation to interstitial tissue, $J_{urine}(t)$, $J_{blood}(t)$, and $J_{evaporation}(t)$ denote loss of fluid volume due to urine production, hemorrhage, or evaporation (and other types of insensible water loss), respectively. Furthermore, $a_{blood}(t)$ denotes the rate of loss of protein (albumin) mass from hemorrhage, $Q_t(t)$ is the rate of albumin mass transfer from circulation to interstitial tissue, and $Q_L(t)$ is the rate of albumin mass transfer from interstitial tissue to circulation.

The above equation can be rewritten in state space form, namely, $$\dot{v}_c(t) = f_1(v(t)) + g(v(t))u(t), v_c(0) = v_{c,0}, t \geq 0 \quad (1)$$

$$\dot{a}_c(t) = f_2(v(t)), a_c(0) = a_{c,0} \quad (2)$$

$$\dot{v}_t = f_3(v(t)), v_t(0) = v_{t,0} \quad (3)$$

$$\dot{a}_t(t) = f_4(v(t)), a_t(0) = a_{t,0} \quad (4)$$

where for $t \geq 0$, $v(t) = [v_c(t), a_c(t), v_t(t), a_t(t)]^T$, and $v_c(t)$, $a_c(t)$, $v_t(t)$, and $a_t(t)$ denote fluid volume in circulation, albumin mass in circulation, fluid volume in interstitial tissue, and albumin mass in interstitial tissue, respectively. In addition, $f_1(v)$ and $f_3(v)$ denote functions characterizing the rate of change of fluid in circulation and tissue compartments, respectively, and $f_2(v)$ and $f_4(v)$ denote functions characterizing the rate of change of albumin in circulation and tissue compartments, respectively, $g(v(t))$ characterizes the effect of fluid infusion on the compartmental model. Note that variables indicating exchange of volume or mass with the outside environment including, $J_{urine}(t)$, $J_{blood}(t)$, $J_{evaporation}(t)$, and $a_{blood}(t)$ have been incorporated into functions $f_1(v)$, $f_2(v)$, and $f_3(v)$. Note that $v_{c,0}$, $a_{c,0}$, $v_{t,0}$, and $a_{t,0}$ denote volume and albumin mass in circulation and interstitial tissue at $t=0$, respectively. Also note that the functions $f_1(v)$, $f_2(v)$, $f_3(v)$, $f_4(v)$, and $g(v)$ are generally unknown for each individual patient.

The original two-compartment model is then modified to introduce a certain structure in the dynamics. A fictitious state, $x_f(t)$, is added such that the fictitious state follows the same trend as the volume of fluid in circulation, $v_c(t)$, with some time lag. The dynamics of the fictitious state is given by the linear differential equation $$\dot{x}_f(t) = c_1 v_c(t) + c_2 x_f(t), x_f(0) = 0, t \geq 0, \quad (5)$$

where $c_1, c_2 \in \mathbb{R}$ are design parameter. Next, error variables are defined that quantify the deviation of each variable from its equilibrium state (steady state value). The error variables are defined by equations (6)-(10):

$$e_f(t) = x_f(t) - x_{f,e} \quad (6)$$

$$e_{v,c}(t) = v_c(t) - v_{c,e} \quad (7)$$

$$e_{a,c}(t) = a_c(t) - a_{c,e} \quad (8)$$

$$e_{v,t}(t) = v_t(t) - v_{t,e} \quad (9)$$

$$e_{a,t}(t) = a_t(t) - a_{t,e} \quad (10)$$

where $e_f(t)$ denotes the deviation of the fictitious state from fictitious state equilibrium value $x_{f,e}$, $e_{v,c}(t)$ denotes the deviation of fluid volume in circulation from its equilibrium value $v_{c,e}$, $e_{a,c}(t)$ denotes the deviation of albumin mass from its equilibrium value $a_{c,e}$, $e_{v,t}(t)$ denotes the deviation of fluid volume in tissue from its equilibrium value $v_{t,e}$, and $e_{a,t}(t)$ denotes the deviation of albumin mass from its equilibrium value $a_{t,e}$.

It follows from (5) that $$v_{c,e} = -\frac{c_2}{c_1} x_{f,e}.$$

Hence, (1)-(5) can be rewritten as $$\dot{e}_f(t) = c_1 e_{v,c}(t) + c_2 e_f(t) \quad (11)$$

$$\dot{e}_{v,c}(t) = \hat{f}_1(e_v(t)) + \hat{g}(e_v(t))u(t), e_{v,c}(0) = e_{v,c,0}, t \geq 0 \quad (12)$$

$$\dot{e}_{a,c}(t) = \hat{f}_2(e_v(t)), e_{a,c}(0) = e_{a,0}, \quad (13)$$

$$\dot{e}_{v,t}(t) = \hat{f}_3(e_v(t)), e_{v,t}(0) = e_{v,t,0}, \quad (14)$$

$$\dot{e}_{a,t}(t) = \hat{f}_4(e_v(t)), e_{a,t}(0) = e_{a,t,0}, \quad (15)$$

where for $t \geq 0$, $e_v(t) = [e_{v,c}(t), e_{a,c}(t), e_{v,t}(t), e_{a,t}(t)]$, and $f_1(v(t))$, $f_2(v(t))$, $f_3(v(t))$, $f_4(v(t))$, $g(v(t))$ are rewritten as $\hat{f}_1(e_v(t))$, $\hat{f}_2(e_v(t))$, $\hat{f}_3(e_v(t))$, $\hat{f}_4(e_v(t))$, $\hat{g}(e_v(t))$, respectively, after performing a change of variables using equations (6)-(10). Parameters $\alpha_1$ and $\alpha_2$ are then introduced, where $\alpha_1, \alpha_2 \in \mathbb{R}$, and equation (12) is rewritten as $$\dot{e}_{v,c}(t) = \alpha_1 e_{v,c}(t) + \alpha_2 e_f(t) + h(\xi(t)) + \hat{g}(e_v(t))u(t), e_{v,c}(0) = e_{v,c,0}, t \geq 0,$$

where $$h(\xi(t)) = \hat{f}_1(e_v(t)) - \alpha_1 e_{v,c}(t) - \alpha_2 e_f(t), \quad (16)$$

and $\xi(t) = [e_{v,c}(t), e_f(t), e_{a,c}(t), e_{v,t}(t), e_{a,t}(t)]^T$.

Next, a series of basis functions are used, such as neural networks basis functions (e.g., radial basis functions or sigmoids), wavelets, or Fourier functions, to approximate $h(\xi)$ and $\hat{g}(\xi)$. Specifically, $$h(\xi(t)) = w_p^T(t) p(\xi) + \varepsilon_p \quad (17)$$

$$\hat{g}(\xi) = w_q^T(t) q(\xi) + \varepsilon_q \quad (18)$$

where $p_1(\xi), \ldots, p_{n_p}(\xi)$ and $q_1(\xi), \ldots, q_{n_q}(\xi)$ are two sets of basis functions, $p(\xi) = [p_1(\xi), \ldots, p_{n_p}(\xi)]^T$, $q(\xi) = [q_1(\xi), \ldots, q_{n_q}(\xi)]^T$, $w_p(t) \triangleq [w_{p,1}(t), \ldots, w_{p,n_p}(t)]^T$, and $w_q(t) \triangleq [w_{q,1}(t), \ldots, w_{q,n_q}(t)]^T$ are time varying weights (or coefficients) corresponding to the basis functions, and $\varepsilon_p$ and $\varepsilon_q$ are the approximation errors.

The presented framework is general; however, for illustration purposes, sigmoidal neural network basis functions of the form $$s(\bar{\xi}) \triangleq \frac{1}{1 + e^{\sigma(\bar{\xi} - \bar{\xi}_0)}}, \sigma, t_0 \in \mathbb{R},$$

can be used. $\alpha_1$, $\alpha_2$, $c_1$, and $c_2$ can be selected such that $$A \triangleq \begin{bmatrix} c_2 & c_1 \\ \alpha_1 & \alpha_2 \end{bmatrix}, \quad (19)$$

is asymptotically stable (i.e., the real parts of all the eigenvalues of A are negative). One specific choice for these parameters are $c_1 = 100$, $c_2 = -100$, $\alpha_1 = 0$, and $\alpha_2 = -100$.

Example 3: Function Approximation for Modeling Unknown Dynamics and Patient Parameters for Cardiovascular Drug Distribution A two-compartment model is used to build the closed-loop cardiovascular administration architecture disclosed herein. The same approach is applied for compartmental models with 3 or more compartments.

A drug mass balance equation for a two-compartment dynamical system model is given by:

$$\dot{d}_c(t) = u(t) - J_M(t) - J_t(t) + J_c(t) - J_{other}(t), t \geq 0$$

$$\dot{d}_t(t) = J_t(t) - J_c(t),$$

where $u(t)$ is the rate of drug infusion, $J_M(t)$ is the rate of drug mass elimination from circulation as a result of metabolism, $J_t(t)$ is the rate of drug mass transfer from circulation to tissue, $J_c(t)$ is the rate of drug mass transfer from tissue to circulation, $J_{other}(t)$ is the rate of drug elimination from circulation other than metabolism (e.g., as a result of hemorrhage).

The above equation can be rewritten in state space form, namely, $$\dot{d}_c(t) = f_1(d(t)) + g(d(t))u(t), d_c(0) = d_{c,0}, t \geq 0 \quad (20)$$

$$\dot{d}_t(t) = f_2(d(t)), d_t(0) = d_{t,0} \quad (21)$$

where for $t \geq 0$, $d(t) = [d_c(t), d_t(t)]^T$, and $dc(t)$ and $d_t(t)$ denote cardiovascular drug mass in circulation and tissue, respectively. In addition, $f_1(d)$ and $f_2(d)$ denote functions characterizing the rate of change of drug mass in circulation and tissue compartments, respectively, $g(d(t))$ characterizes the effect of cardiovascular drug infusion on the compartmental model. Note that variables indicating exchange of mass with the outside environment, that is, $J_{other}(t)$, and $J_M(t)$, have been incorporated into function $f_1(d)$, and $f_2(v)$. Note that $d_{c,0}$, and $d_{t,0}$, denote drug mass in circulation and tissue at $t=0$, respectively. Also note that the functions $f_1(d), f_2(d)$, and $g(d)$ are generally unknown for each individual patient.

The original two-compartment model is then modified to introduce a certain structure in the dynamics. A fictitious state, $x_f(t)$, is added such that the fictitious state follows the same trend as the cardiovascular drug mass in circulation, $d_c(t)$, with some time lag. The dynamics of the fictitious state is given by the linear differential equation $$\dot{x}_f(t) = c_2 d_c(t) + c_1 x_f(t), x_f(0) = 0, t \geq 0, \quad (22)$$

where $c_1, c_2 \in \mathbb{R}$ are design parameters. Next, error variables are defined that quantify the deviation of each variable from its equilibrium state (steady state value). The error variables are defined by equations (23)-(26):

$$e_f(t) = x_f(t) - x_{f,e} \quad (23)$$

$$e_{d,c}(t) = d_c(t) - d_{c,e} \quad (24)$$

$$e_{d,t}(t) = d_t(t) - d_{t,e} \quad (25)$$

where $e_f(t)$ denotes the deviation of the fictitious state from fictitious state equilibrium value $x_{f,e}$, $e_{d,c}(t)$ denotes the deviation of cardiovascular drug mass in circulation from its equilibrium value $d_{c,e}$, and $e_{d,t}(t)$ denotes the deviation of cardiovascular drug mass in tissue from its equilibrium value $d_{t,e}$.

It follows from (22) that $$d_{c,e} = -\frac{c_1}{c_2} x_{f,e}.$$

Hence, (20)-(22) can be rewritten as $$\dot{e}_f(t) = c_2 e_{d,c}(t) + c_1 e_f(t) \quad (26)$$

$$\dot{e}_{d,c}(t) = \hat{f}_1(e_d(t)) + \hat{g}(e_d(t))u(t), e_{d,c}(0) = e_{d,c,0}, t \geq 0 \quad (27)$$

$$\dot{e}_{d,t}(t) = \hat{f}_2(e_d(t)), e_{d,t}(0) = e_{d,t,0}, \quad (28)$$

where for $t \geq 0$, $e_d(t) = [e_{d,c}(t), e_{d,t}(t)]$, and $f_1(d(t))$, $f_2(d(t))$, $g(d(t))$ are rewritten as $\hat{f}_1(e_d(t))$, $\hat{f}_2(e_d(t))$, $\hat{g}(e_d(t))$, respectively, after performing a change of variables using equations (23)-(26). Parameters $\alpha_1$ and $\alpha_2$ are then introduced, where $\alpha_1, \alpha_2 \in \mathbb{R}$, and equation (12) is rewritten as $$\dot{e}_{d,c}(t) = \alpha_1 e_{d,c}(t) + \alpha_2 e_f(t) + h(\xi(t)) + \hat{g}(e_d(t))u(t), e_{d,c}(0) = e_{d,c,0}, t \geq 0,$$

where $$h(\xi(t)) = \hat{f}_1(e_d(t)) - \alpha_1 e_{d,c}(t) - \alpha_2 e_f(t), \quad (29)$$

and $\xi(t)[e_{d,c}(t), e_f(t), e_{d,t}(t)]$.

Next, a series of basis functions are used, such as neural networks basis functions (e.g., radial basis functions or sigmoids), wavelets, or Fourier functions, to approximate $h(\xi)$ and $\hat{g}(\xi)$. Specifically, $$h(\xi) = w_p^T(t) p(\xi) + \varepsilon_p \quad (30)$$

$$\hat{g}(\xi) = w_q^T(t) q(\xi) + \varepsilon_q \quad (31)$$

where $p_1(\xi), \ldots, p_{n_p}(\xi)$ and $q_1(\xi), \ldots q_{n_q}(\xi)$ are two sets of basis functions, $p(\xi) = [p_1(\xi), \ldots, p_{n_p}(\xi)]^T$, $q(\xi) = [q_1(\xi), \ldots, q_{n_q}(\xi)]^T$, $w_p(t) \triangleq [w_{p,1}(t), \ldots, w_{p,n_p}(t)]^T$, and $w_q(t) \triangleq [w_{q,1}(t), \ldots w_{q,n_q}(t)]_T$ are time varying weights (or coefficients) corresponding to the basis functions, and $\varepsilon_p$ and $\varepsilon_q$ are the approximation errors.

The presented framework is general; however, for illustration purposes, sigmoidal neural network basis functions of the form $$s(\bar{\xi}) \triangleq \frac{1}{1 + e^{\sigma(\bar{\xi} - \bar{\xi}_0)}}, \sigma, t_0 \in \mathbb{R},$$

can be used. $\alpha_1$, $\alpha_2$, $c_1$, and $c_2$ can be selected such that $$A \triangleq \begin{bmatrix} c_1 & c_2 \\ \alpha_1 & \alpha_2 \end{bmatrix}, \quad (32)$$

is asymptotically stable (i.e., the real parts of all the eigenvalues of A are negative). One specific choice for these parameters are $c_1 = 0.2$, $c_2 = 0.013$, $\alpha_1 = 0$, and $\alpha_2 = -0.2$.

Example 3: Computing the Value of Continuous Infusion

At each time instant t, the infusion rate of the controller (for fluid or cardiovascular drug) is given by $$u(t) = \begin{cases} 0, & \hat{u}(t) \leq 0, \\ \hat{u}(t), & \hat{u}(t) > 0 \end{cases},$$

where $$\hat{u}(t) = -\frac{1}{1 + w_q^T(t) Q(z(t))} w_p^T(t) P(z(t)),$$

and $$z(t) \triangleq [m(t - \Delta t), m(t - 2\Delta t), u(t - \Delta t), u(t - 2\Delta t)]^T,$$

$$P(z(t)) = Q(z(t)) \triangleq \left[ \frac{1}{1 + e^{-\sigma_1(m(t-\Delta t) - m_{target})}}, \ldots, \frac{1}{1 + e^{-\sigma_{n_{node}}(m(t - \Delta t) - m_{target})}}, \right.$$

$$\frac{1}{1 + e^{-\sigma_1(m(t-2\Delta t) - m_{target})}}, \ldots, \frac{1}{1 + e^{-\sigma_{n_{node}}(m(t-2\Delta t) - m_{target})}}, \frac{1}{1 + e^{-\sigma_1 u(t-\Delta t)}},$$

$$\left. \ldots, \frac{1}{1 + e^{-\sigma_{n_{node}} u(t-\Delta t)}}, \frac{1}{1 + e^{-\sigma_1 u(t-2\Delta t)}}, \ldots, \frac{1}{q + e^{-\sigma_{n_{node}} u(t-2\Delta t)}} \right],$$

$\sigma_1, \ldots, \sigma_{n_{node}}$, are sigmoid parameters (e.g., ranging from $-100$ to $100$), $n_{node}$ represents the number of nodes of the neural network (e.g., node=8), and m(t) represents the smoothed (denoised) sensor measurement used as an endpoint for fluid or drug administration (e.g., stroke volume variation, urine output rate, mean arterial pressure, central venous pressure, systolic pressure variation, etc. for fluid resuscitation; and mean arterial pressure, heart rate, systolic pressure, diastolic pressure, systemic vascular resistance, central venous pressure, etc. for cardiovascular drug administration) at time t. u(t) represents computed infusion rate at time t. For example, smoothed (denoised) sensor measurement can be obtained by a moving window average where the mean value of the sensor measurement in a time window (e.g., 2 minutes) is computed and assigned to m(t). Sensor values can be preprocessed to drop measurements that appear to be noisy or invalid and only acceptable values are included in the window averaging.

Alternatively, $$z(t) \triangleq [m(t-\Delta t), u(t-\Delta t)]^T,$$

$$P(z(t)) = Q(z(t)) \triangleq \left[\frac{1}{1+e^{-\sigma_1(m(t-\Delta t)-m_{target})}}, \ldots, \right.$$

$$\left.\frac{1}{1+e^{-\sigma_{n_{node}}(m(t-\Delta t)-m_{target})}}, \frac{1}{1+e^{-\sigma_1 u(t-\Delta t)}}, \ldots, \frac{1}{1+e^{-\sigma_{n_{node}} u(t-\Delta t)}}\right].$$

The update laws for the weights are given by the set of ordinary differential equations $$\dot{w}_p(t) = \beta_1 \Gamma(w_p(t), -P(z(t))x_c^T(t)\tilde{P}B_0), w_p(0) = w_{p,0}, t \geq 0,$$

$$\dot{w}_q(t) = \beta_2 \Gamma(w_q(t), -Q(z(t))u(t)x_c^T(t)\tilde{P}B_0), w_q(0) = w_{q,0},$$

$$\dot{x}_c(t) = Ax_c(t) + L(m(t) - m_{target} - y_c(t)), x_c(0) = 0,$$

$$y_c(t) = Cx_c(t),$$

where $x_c(t) = [x_{c,1}(t), x_{c,2}(t)]^T$ represents the estimated values of $e_f(t)$ and $e_{v,c}(t)$ (in the case of fluid resuscitation) or $e_f(t)$ and $e_{d,c}(t)$ (in the case of cardiovascular drug administration), $\beta_1, \beta_2 > 0$ denote design parameters (e.g., $\beta_1 = 0.02$ and $\beta_2 = 0.04$), and representative values for other parameters are given by $L = [-1, 0]^T$, $B_0 = [0, 1]^T$, and $C = [-1, 0]^T$. In addition, $m_{target}$ is the desired value for the end point of fluid resuscitation or cardiovascular drug administration (e.g., for fluid resuscitation if the goal is to maintain a stroke volume variation of 13%, then $m_{target} = 13$; similarly, for cardiovascular drug administration if the goal is to maintain a mean arterial pressure of 65 mmHg, then $m_{target} = 65$), and $\tilde{P}$ satisfies the Lyapunov equation given by:

$$(A-LC)^T \tilde{P} + \tilde{P}(A-LC) + \tilde{R} = 0, \quad (33)$$

where $\tilde{R} > 0$.

For example, if $\tilde{R} = I_{2\times 2}$ and the parameter values above are used, then $$\tilde{P} = \begin{bmatrix} 0.4116 & 0.0039 \\ 0.0039 & 2.5 \end{bmatrix}$$

for cardiovascular drug administration, and $$\tilde{P} = \begin{bmatrix} 0.0005 & 0.003 \\ 0.003 & 0.008 \end{bmatrix}$$

for fluid resuscitation. In addition, the function $\Gamma(\theta, y)$ is used to ensure that controller parameters remain bounded. This function is defined as:

$$\Gamma(\theta, y) \triangleq \begin{cases} y, & \text{if } f(\theta) < 0, \\ y, & \text{if } f(\theta) \geq 0, \text{ and } \nabla f^T y \leq 0, \\ y - \frac{\nabla f}{\|\nabla f\|} \left\langle \frac{\nabla f}{\|\nabla f\|}, y \right\rangle f(\theta), & \text{if } f(\theta) \geq 0 \text{ and } \nabla f^T y > 0 \end{cases},$$

where $f: \mathbb{R}^n \to \mathbb{R}$ is defined as $$f(\theta) \triangleq \frac{(\varepsilon_\theta + 1)\theta^T \theta - \theta_{max}^2}{\varepsilon_\theta \theta_{max}^2}, \quad (34)$$

$\theta_{max} > 0$, $\varepsilon_\theta > 0$, $\nabla(\cdot)$ represents the gradient operator, and $\|\cdot\|$ represents the Euclidean norm. For example, $\theta_{max} = 1e6$ and $\varepsilon_\theta = 1e-5$.

Example 4: Computer Simulations for Fluid Resuscitation

Adaptive control framework is used to simulate fluid resuscitation of a 70 kg patient losing blood at a rate of 2 ml/kg/min at t=0. The goal is to maintain the stroke volume variation measurements at 15%. A $\Delta t$ of 0.001 hour (3.6 seconds) is used for the simulations and $\beta_1 = 2$, $\beta_2 = 4$, and $n_{node} = 8$. The patient model involved a compartmental model to model fluid distribution and the relationship between volume in circulation and SVV was based on a nonlinear relationship based on experimental results on dogs.

Figure 7:
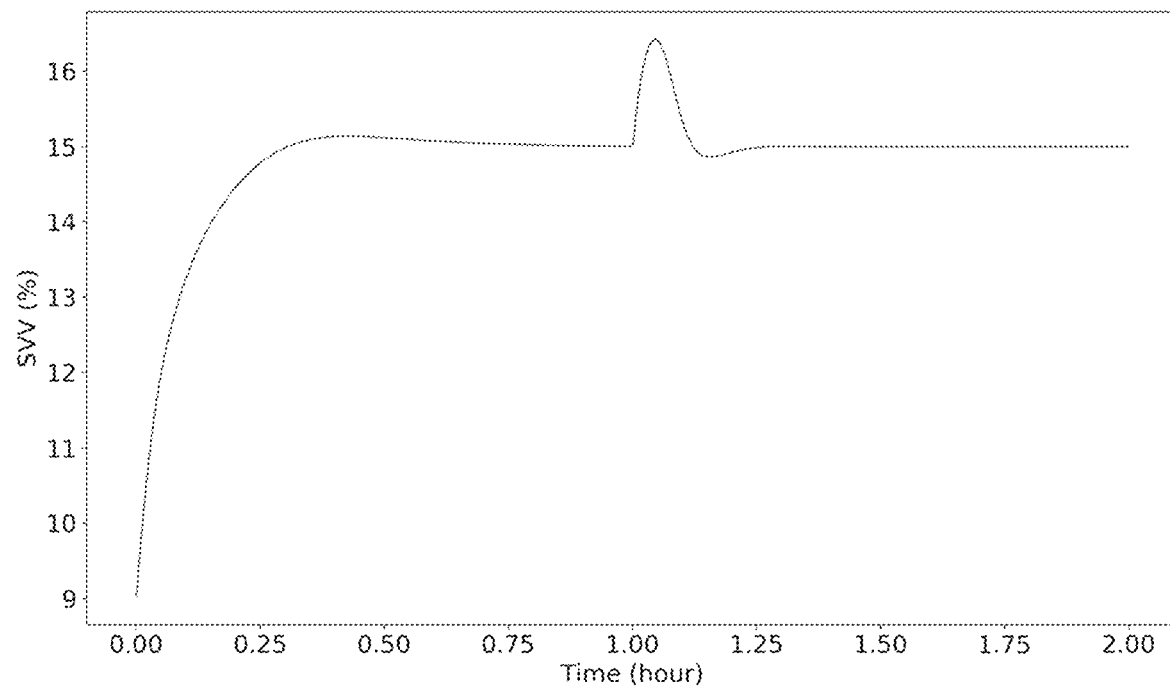
FIG. 7 is a graph that depicts exemplary stroke volume variation versus time.

FIG. 7 shows stroke volume variation (SVV (%)) versus time. The target stroke volume variation is 15%. The SVV (%) starts at about 9%, and changes with the introduction of fluid resuscitation. The SVV (%) increases to the target value of 15%. At t=1 hr, the blood loss increases to 3 mL/kg/min, and the controller increases the infusion rate to drive stroke volume variation measurements to the target value of 15%.

Figure 8:
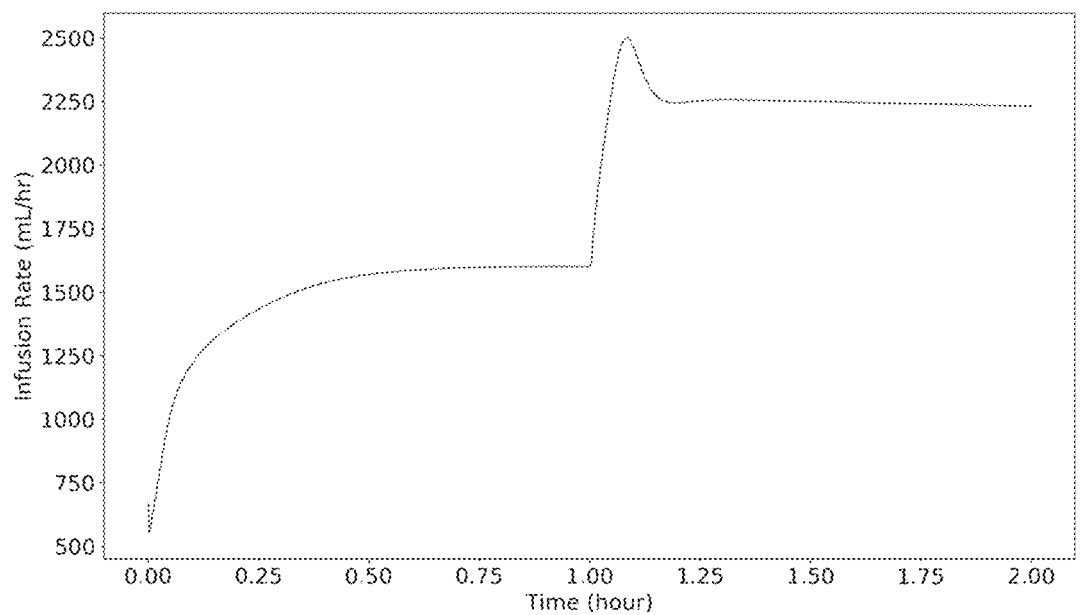
FIG. 8 is a graph that depicts exemplary fluid infusion rates computed by the adaptive control framework.

FIG. 8 shows infusion rates computed by the adaptive control framework. The infusion rate is about 700 mL/h at t=0 (start of the simulation). The infusion rate is rapidly increased to about 1500 mL/h to maintain an SVV (%) of 15%. At t=1 hr, the blood loss increases to 3 mL/kg/min, and the controller increases the infusion rate to about 2250 mL/h to maintain the target SVV (%) of 15%.

Figure 9:
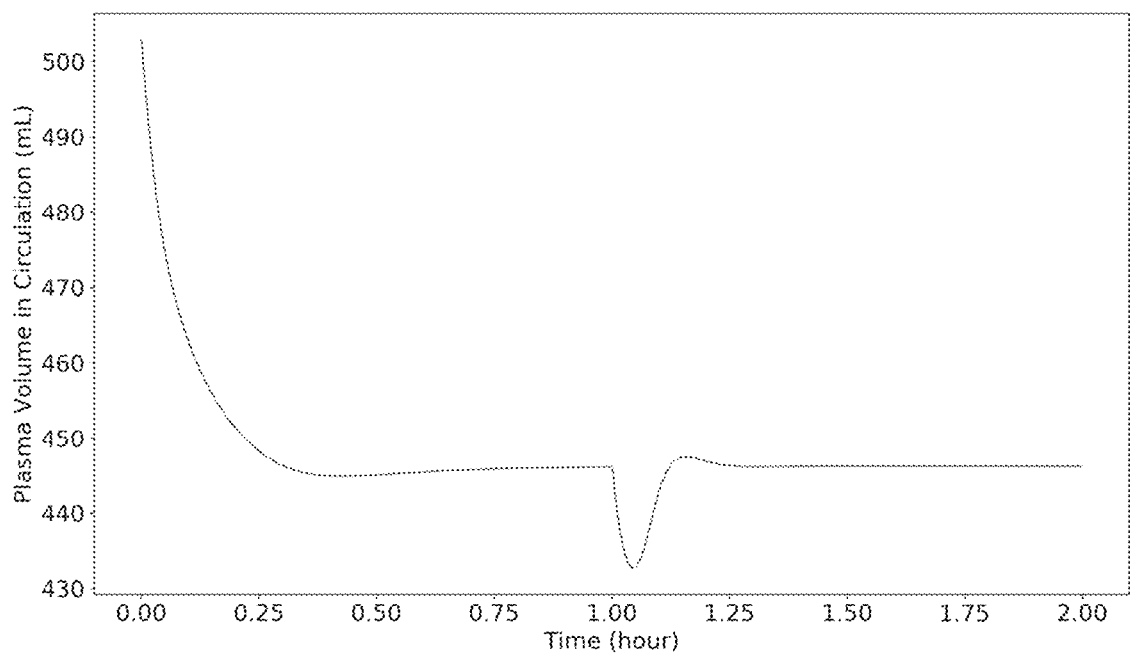
FIG. 9 is a graph that depicts exemplary plasma volume in circulation versus time.

FIG. 9 shows plasma volume in circulation versus time. The plasma volume in circulation rapidly decreases due to loss of blood in spite of fluid resuscitation until reaching an equilibrium value of about 450 mL. At t=1 hr, the blood loss increases to 3 mL/kg/min, and the controller increases the infusion rate to drive stroke volume variation measurements to the target value of 15%. The plasma volume in circulation remains about the same even after an increase in blood loss.

Example 5: Animal Study for Fluid Resuscitation

The adaptive control framework of the disclosure was used to provide automated and semi-automated (clinical decision support) fluid resuscitation to five dogs in different hemorrhaging/hypovolemic scenarios.

Five mature intact Beagle dogs, determined to be healthy based on a physical examination and hemogram, were included in the experiment. The dogs were individually housed and provided commercial dry dog food and water ad libitum. Each dog and experiment was identified (Table 1). For example, S1-2 represents the second experiment performed on Subject S1. Studies on subjects were performed on different days. Individual trials on the same subject were performed on the same day and a stabilization period was used between trials. All dogs were euthanized with sodium pentobarbital (100 mg/kg, IV) upon completion of the experiments.

TABLE 1

Study subject information and experiment summary.

| Subject | Weight (kg) | Study 1 | Study 2 |
| --- | --- | --- | --- |
| S1 | 11.6 | CH | CH |
| S2 | 7.1 | RAH | RAH |

TABLE 1-continued

Study subject information and experiment summary.

| Subject | Weight (kg) | Study 1 | Study 2 |
|---|---|---|---|
| S3 | 10.8 | UH | — |
| S4 | 12.2 | RH | UH |
| S5 | 9.3 | RH | UH |

CH = controlled hypovolemia, UH = uncontrolled hypovolemia, RH = relative hypovolemia, RAH = relative and absolute hypovolemia Animal Preparation: Food but not water was withheld for 6 hours before each experiment. An intravenous catheter was transcutaneously positioned in the cephalic vein for administration of hydromorphone, 0.15 mg/kg IV. Anesthesia was produced ten minutes later by administering 3.5 to 6 mg/kg IV propofol to facilitate orotracheal intubation, and initially maintained at a vaporizer setting of 1.5-2% isoflurane in oxygen. The dogs were positioned on their right side and mechanically ventilated at 10-12 breaths/min and 10-14 ml/kg tidal volume in order to maintain the end-tidal partial pressure of carbon dioxide ($ET_{CO2}$) between 38 and 48 mmHg. To avoid potential changes in SVV, tidal volume settings for each subject was not changed during the study. Esophageal temperature was maintained (37° C.) with temperature-controlled warm air blankets.

Vascular catheters were surgically placed in the left jugular vein and right carotid and femoral arteries after perivascular administration of 0.5-1.0 ml 2% lidocaine. The carotid or femoral artery catheter was connected to a FloTrac sensor with low-compliance fluid filled tubing. The FloTrac sensor was connected to a Vigileo monitor for determination and continuous monitoring of SVV. The FloTrac sensor was positioned and zeroed at the level of the sternum. The pressure line of the FloTrac sensor was flushed with 4 ml/hr of lactated ringer's solution (LRS). Heart rate was determined from a Lead II electrocardiogram (ECG). Criteria for obtaining accurate SVV recordings during mechanical ventilation were employed.

A 5 Fr Swan-Ganz catheter was percutaneously advanced via the right jugular vein (2 dogs) into the pulmonary artery under fluoroscopic guidance for measurement of cardiac output by thermodilution. Alternatively, cardiac output was determined by a previously implanted flow probe (3 dogs) positioned around the ascending aorta, proximal to brachiocephalic trunk for continuous recording of cardiac output.

Experimental Procedures: Five dogs were subjected to 9 experiments. Lactated Ringer's solution (LRS) was administered as fluid resuscitation. A variety of experimental hypovolemic conditions were created in order to mimic various clinical conditions (Table 1). Absolute controlled hypovolemia (2 trials) was produced during 1.5 minimum alveolar concentration (MAC: 1.27% used throughout) of isoflurane anesthesia by withdrawing 15 ml/kg/15 minutes from either the right carotid or right femoral artery (S1-1). There was a 30-minute stabilization period between the end of the closed-loop fluid resuscitation (S1-1) and the beginning of the second hemorrhage, 40 ml/kg/30 minutes (S1-2). Closed-loop fluid administration was initiated within 10 minutes of completion of each blood withdrawal and continued until SVV reached a predetermined target range equal to or less than 13±3%.

Absolute uncontrolled hypovolemia (S3-1, S4-2, S5-2; 3 trials), designed to simulate blood loss from a severed artery was produced by withdrawal of approximately 50% (40 ml/kg) of the dogs estimated blood volume (80 ml/kg) from the right carotid or right femoral artery over one hour. Five successive 8.0 ml/kg increments of blood were withdrawn continuously in increments that were completed at approximately 7-8, 18-20, 30-32, 43-45, and 60 minutes after initiating hemorrhage. Closed-loop fluid resuscitation was initiated 10 minutes after initiation of absolute uncontrolled hypovolemia (i.e., beginning of Stage 2 of blood withdrawal) and continued until SVV reached a predetermined target range equal to or less than 13±3%.

Relative hypovolemia (2 trials) was produced by either increasing the inspired concentration of isoflurane to 2.0-2.5 MAC (S5-1, 1 trial) or administering sodium nitroprusside (5-10 mcg/kg/min; S4-1, 1 trial) until mean arterial blood pressure was ≤ 50 mm Hg. The target range SVV was set at 13±3% for S4-1 and 5±3% for S5-1. Relative and controlled absolute hypovolemia were produced by increasing the concentration of isoflurane (0.25-0.5%, 1.5-2.0 MAC multiples) in order to decrease MAP by 30% (S2-1, 1 trial) or administering sodium nitroprusside (1-15 mcg/kg/min; S2-2, 1 trial) followed by withdrawal of 15 ml/kg/minutes of blood. The target range SVV was set at 13±3% for S2-1 and S2-2. The subject was resuscitated to the target SVV value in S2-1 and stabilized before initiating the second study (S2-2). Fluid resuscitation started 15 minutes after achieving relative and controlled absolute hypovolemia.

The closed-loop fluid resuscitation system was employed in a "partial automation" mode (clinical decision support) in two experimental trials, one involving absolute uncontrolled hemorrhage (S4-2) and one involving relative hypovolemia from sodium nitroprusside administration (S4-1), where the system displayed the recommended infusion rate every minute and the user manually changed the infusion rate. A Horizon NXT Modular Infusion System pump was used in the partial automated mode. While the system was able to provide infusion rate recommendations more frequently, an update interval of 1 minute was chosen to allow sufficient time for the clinical staff to adjust the pump settings manually. Measured SVV values were filtered in all studies, including automated and partially automated modes, using a 1-minute moving window averaging to remove noise. The adaptive controller was implemented using a neural network with sigmoidal basis functions to use as the function approximator.

The subject continuously received a fluid infusion and the control system changed the infusion rate every few seconds in response to changes in SVV. Vigileo transmitted the most recent value of the SVV measurement every 2 seconds using serial communication. The adaptive control framework was implemented on a laptop. The laptop was connected to the Vigileo using a Serial to USB cable. The closed-loop fluid resuscitation system used a 1-minute moving window averaging to remove noise. The control algorithm was implemented in the Python programming language running on a laptop with the Linux operating system. Measurements from Vigileo were recorded by the laptop using serial communication. The closed-loop fluid resuscitation algorithm computed an infusion rate every 11 seconds using the average SVV values in the past 1-minute. The infusion rate was sent by the laptop to an infusion pump (supporting flow rates from 0.06 to 4200 ml/hr) using a USB connection.

Performance Metrics: Performance metrics that are of clinical relevance were defined in order to assess the performance of the closed-loop fluid resuscitation system. Specifically, $T_{target}$ was defined as the duration from start of fluid administration to restoration of an acceptable SVV target range.

We defined the acceptable SVV target range to be equal to 13±3% with the exception of two experiments, namely, S5-2 (uncontrolled hypovolemia) and S5-1 (relative hypovolemia), where the acceptable SVV target range was 10±3% and 5±3%, respectively. The $R_{in\ range}$ was defined as the percentage of time that SVV stayed in the acceptable range once SVV target range was reached (i.e., duration of time SVV stayed in the acceptable range once SVV target range was reached divided by total duration of resuscitation). Other performance metrics included minimum and maximum infusion rates denoted by $u_{min}$ and $u_{max}$, respectively, total infused volume to reach the acceptable SVV target range denoted by $V_{target}$, and, in absolute hypovolemia experiments, the ratio of total fluid volume infused to total blood loss denoted by $V_{ratio}$. To ensure that the subject can be maintained at the acceptable SVV target range, the resuscitation continued after reaching the acceptable SVV target range, and hence, $V_{target}$ and total infused volume are not equal. Continued resuscitation after reaching $V_{target}$ lasted approximately 15 minutes on average. The stabilization period between different trials on the same subject started after the completion of the fluid resuscitation of the previous trial.

Controlled Hypovolemia: Absolute hypovolemia during 1.5 MAC isoflurane anesthesia decreased MAP from 100 to 86 mmHg (S-1) and from 109 to 54 mm Hg (S1-2) after withdrawal of 15 ml/kg and then 40 ml/kg of blood respectively (Table 2). Heart rate increased and cardiac output decreased after withdrawal of 15 ml/kg and 40 ml/kg of blood (Table 2). In addition, the SVV increased after withdrawal of 15 ml/kg and 40 ml/kg of blood. The SVV returned to the target range (13%±3) after the administration of 7 ml/kg and 66 ml/kg of LRS, respectively (Table 2). The total infused volumes were 189 ml (S1-1: $V_{ratio}$=1.1) and 925 ml (S1-2: $V_{ratio}$=2), respectively.

TABLE 2

Hemodynamic data and performance metrics for controlled hypovolemia study. $T_{target}$ denotes the duration from start of fluid administration to restoration of an acceptable SVV target range, $u_{min}$ and $u_{max}$ denote minimum and maximum infusion rates, respectively, and $V_{target}$ denotes total infused volume to reach the acceptable SVV target range.

| | Baseline | | Before Resuscitation | | After Resuscitation | |
|---|---|---|---|---|---|---|
| ml/kg bled | 15 | 40 | 15 | 40 | 15 | 40 |
| CO (L/min) | 1.5 | 2.1 | 1.3 | 0.8 | 2.1 | 1.6 |
| MAP (mmHg) | 100 | 109 | 86 | 54 | 109 | 63 |
| HR (bpm) | 85 | 108 | 107 | 187 | 108 | 154 |
| SVV (%) | 6 | 15 | 19 | 42 | 13 | 16 |

| Performance Metrics | | | | |
|---|---|---|---|---|
| Study | $T_{target}$ (min) | $u_{min}$ (ml/kg/hr) | $u_{max}$ (ml/kg/hr) | $V_{target}$ (ml/kg) |
| S1-1 (15 ml/kg) | 6.6 | 26 | 64 | 7 |
| S1-2 (40 ml/kg) | 50.3 | 70 | 87 | 66 |

Uncontrolled Hypovolemia: Closed-loop fluid administration was initiated during the second stage of blood withdrawal, and continued throughout hemorrhage (S3-1, S4-2, S5-2). Closed-loop fluid administration was stopped approximately 30 minutes after the end of the last (fifth) stage of hemorrhage as this exceeds the average time for fluid equilibration with the interstitial fluid compartment. Mean arterial blood pressure and cardiac output decreased and heart rate increased during the initial 3-4 stages of uncontrolled hypovolemia (Table 3). Heart rate increased throughout hemorrhage and remained elevated throughout hemorrhage and fluid administration (Table 3). The SVV increased during the first stage of uncontrolled hypovolemia and returned toward baseline values thereafter (Table 3). Total infused volumes for S3, S4, and S5 were 1,092 ml ($V_{ratio}$=2.5), 1,243 ml ($V_{ratio}$=2.8), and 548 ml ($V_{ratio}$=1.4), respectively. The fluid administration system was used in a partially-automated (human-in-the-loop) mode for S4, where the recommended infusion rate was displayed to the user every minute and the user manually changed the infusion rate to the recommended value.

TABLE 3

Hemodynamic data and performance metrics for uncontrolled hypovolemia study. $u_{min}$ and $u_{max}$ denote minimum and maximum infusion rates, respectively, and $R_{in\ range}$ the percentage of time that SVV target value stayed in the acceptable range once SVV target range was reached.

| | Baseline | Stage 1 | Stage 2 | Stage 3 | Stage 4 | Stage 5 | End |
|---|---|---|---|---|---|---|---|
| CO (L/min) | 1.5 (1.1-1.7) | 0.8 (0.5-1.5) | 0.8 (0.3-1.4) | 1.0 (0.4-1.4) | 0.9 (0.4-1.7) | 1.0 (0.7-1.7) | 1.3 (1.1-2.0) |
| MAP (mmHg) | 81 (62-85) | 59 (55-91) | 66 (35-87) | 65 (45-67) | 68 (50-72) | 68 (53-78) | 59 (44-83) |
| HR (bpm) | 118 (113-121) | 134 (120-171) | 132 (108-170) | 132 (117-174) | 135 (117-170) | 139 (116-168) | 137 (107-167) |
| SVV (%) | 8 (6-12) | 21 (17-25) | 17 (12-19) | 15 (11-16) | 14 (11-16) | 15 (10-15) | 10 (8-18) |

TABLE 3-continued

Hemodynamic data and performance metrics for uncontrolled hypovolemia study. $u_{min}$ and $u_{max}$ denote minimum and maximum infusion rates, respectively, and $R_{in\ range}$ the percentage of time that SVV target value stayed in the acceptable range once SVV target range was reached.

| | Performance Metrics | | |
|---|---|---|---|
| Dog | $u_{min}$ (ml/kg/hr) | $u_{max}$ (ml/kg/hr) | $R_{in\ range}$ (%) |
| S3-1 | 44 | 115 | 54 |
| S4-2 | 40 | 82 | 71 |
| S5-2 | 39 | 64 | 100 |

Relative Hypovolemia from Vasodilatation: Dogs were made hypotensive by increasing the inspired concentration of isoflurane (S5-1) or by administering sodium nitroprusside (S4-1) until mean arterial blood pressure was less than or equal to 50 mmHg. The target range SVV was set at 13±3% for S4-1 and 5±3% for S5-1. The administration of isoflurane or sodium nitroprusside decreased mean arterial blood pressure and increased heart rate and either did not change or increased cardiac output, respectively (Table 4). SVV increased in both dogs (Table 4). Closed-loop fluid resuscitation increased cardiac output and decreased SVV in both dogs. Arterial blood pressure increased during fluid administration in the dog administered sodium nitroprusside (S4-1) but not in the dog administered isoflurane (S5-1) (Table 4). Total infused volumes were 187 ml (nitroprusside: 15 ml/kg) and 265 ml (isoflurane: 28 ml/kg).

TABLE 4

Hemodynamic data and performance metrics for the relative hypovolemia study.

| | Baseline | Before Resuscitation | After Resuscitation |
|---|---|---|---|
| CO (L/min) | 0.8 I; 1.4 SN | 0.8 I; 1.6 SN | 1.4 I; 2.0 SN |
| MAP (mmHg) | 62 I; 69 SN | 45 I; 47 SN | 35 I; 94 SN |
| HR (bpm) | 84 I; 89 SN | 87 I; 115 SN | 89 I; 126 SN |
| SVV (%) | 7 I; 9 SN | 10 I; 17 SN) | 6 I; 8 SN |

| | Performance Metrics | | | | |
|---|---|---|---|---|---|
| Study | $T_{target}$ (min) | $u_{min}$ (ml/kg/hr) | $u_{max}$ (ml/kg/hr) | $V_{target}$ (ml/kg) | $R_{in\ range}$ (%) |
| S4-1 | 3 | 11 | 67 | 3 | 100 |
| S5-1 | 4 | 63 | 73 | 5 | 90 |

$T_{target}$ denotes the duration from start of fluid administration to restoration of an acceptable SVV target range, $u_{min}$ and $u_{max}$ denote minimum and maximum infusion rates, respectively, $V_{target}$ denotes total infused volume to reach the acceptable SVV target range, and $R_{in\ range}$ the percentage of time that SVV stayed in the acceptable range once SVV target range was reached.
I = isoflurane; SN = sodium nitroprusside Relative Hypovolemia and Controlled Hypovolemia: Increasing the isoflurane concentration from 1.5 to 2.5 MAC (S2-1) or administration of sodium nitroprusside (S2-2) was followed by blood withdrawal (15 ml/kg/15 minutes). The sodium nitroprusside infusion rate started at 1 mcg/kg/min and was increased to 15 mcg/kg/min. The target range SVV was set at 13±3%. Absolute hypovolemia (15 ml/kg/15 min) during 2.5 MAC isoflurane anesthesia decreased MAP from 60 mmHg before blood withdrawal to 39 mm Hg after blood withdrawal (S2-1). In addition, MAP increased from 39 mmHg to 46 mmHg after a 15-minute stabilization period. Heart rate changed minimally (110 vs. 112 bpm) and cardiac output decreased 20% (1.0 vs. 0.8 L/min) after the production of relative hypovolemia combined with controlled hypovolemia (15 ml/kg/15 min). The SVV increased from 13% at 1.5 MAC to 21% at 2.5 MAC and then to 41% after withdrawal of 15 ml/kg of blood. The SVV decreased to 26% after a 15-minute stabilization period. The SVV returned to the target range (13%±3) at 43 minutes ($T_{target}$) after the administration of 78 ml/kg of LRS. Total infused volume was 573 ml ($V_{ratio}$=5.4). The maximum fluid administration rate ($u_{max}$) was 113 ml/kg/hr. Heart rate decreased (112 to 99) and cardiac output increased to above the baseline value (1.0 vs. 1.2) after LRS administration but MAP remained relatively unchanged (43 mm Hg) until the isoflurane concentration was decreased.

Absolute hypovolemia (15 ml/kg/15 min) during 1.5 MAC and sodium nitroprusside administration decreased MAP from 113 to 92 mmHg prior to blood withdrawal (S2-2). MAP was 101 mmHg after blood withdrawal. Heart rate changed minimally and cardiac output decreased 25% (1.3 vs. 1.0 L/min) after the production of relative hypovolemia combined with controlled hypovolemia (15 ml/kg/15 min). The SVV increased from 10% to 15% after sodium nitroprusside administration and then to 22% after withdrawal of 15 ml/kg of blood. The SVV returned to the target range (13%±3) at 26 minutes ($T_{target}$) after the administration of 46 ml/kg of LRS. The maximum fluid administration rate ($u_{max}$) was 108 ml/kg/hr. Cardiac output increased to above the baseline value (1.3 vs. 2.1) after LRS administration and MAP increased to near the baseline value (Table 5). Total infused volume was 400 ml ($V_{ratio}$=3.7).

TABLE 5

Hemodynamic data and performance metrics for the relative hypovolemia and controlled hypovolemia study.

| | Baseline | Before Resuscitation | After Resuscitation |
|---|---|---|---|
| CO (L/min) | 1.0 I; 1.3 SN | 0.8 I; 1.0 SN | 1.2 I; 2.1 SN |
| MAP (mmHg) | 93 I; 113 SN | 46 I; 101 SN | 40 I; 115 SN |
| HR (bpm) | 110 I; 134 SN | 112 I; 114 SN | 99 I; 108 SN |
| SVV (%) | 13 I; 10 SN | 26 I; 22 SN | 15 I; 21 SN |

| | Performance Metrics | | | | |
|---|---|---|---|---|---|
| Study | $T_{target}$ (min) | $u_{min}$ (ml/kg/hr) | $u_{max}$ (ml/kg/hr) | $V_{target}$ (ml/kg) | $R_{in\ range}$ (%) |
| S2-1 | 43 | 88 | 113 | 78 | 100 |
| S2-2 | 26 | 66 | 108 | 46 | 53 |

$T_{target}$ denotes the duration from start of fluid administration to restoration of an acceptable SVV target range, $u_{min}$ and $u_{max}$ denote minimum and maximum infusion rates, respectively, $V_{target}$ denotes total infused volume to reach the acceptable SVV target range, and $R_{in\ range}$ the percentage of time that SVV stayed in the acceptable range once SVV target range was reached.
I = isoflurane; SN = sodium nitroprusside The closed-loop fluid resuscitation system used the compartmental modeling framework to compute fluid infusion rates. The two-compartment model of the microvascular exchange system involved parameters that are generally unknown and different from patient to patient. In addition, the two-compartment model was only an approximation of the fluid distribution in the body, resulting in modeling error.

The adaptive control fluid resuscitation algorithm uses the compartmental characteristics of the fluid distribution in the body. To address modeling error and unknown parameters of the compartmental model governing fluid distribution, the adaptive algorithm used a "function approximator." The function approximator was characterized by a set of parameters, which were continuously estimated by the closed-loop system in real-time. The closed-loop fluid resuscitation system re-computes the fluid infusion rate periodically. The function approximator used the values of infusion rates and SVV measurements to estimate the dynamics of fluid distribution. The controller performance was evaluated with computer simulations on a two-compartment model prior to conducting the animal study. The results presented are the first attempt to use the disclosure in live subjects.

Data from this study confirmed that an adaptive closed-loop fluid administration system based on a compartmental model of fluid distribution provided targeted goal-directed fluid therapy in dogs subjected to experimental conditions that mimicked clinical scenarios of absolute (controlled, uncontrolled), relative hypovolemia or a combination of relative hypovolemia and absolute controlled hypovolemia. Stroke volume variation was restored and maintained to within a preselected normal target range in less than one hour after initiating fluid administration. Larger volumes of blood loss (40 vs.15 ml/kg) increased the $V_{ratio}$ required to restore SVV to the target range but remained below amounts based upon lactated ringer's solution (LRS) distribution.

The adaptive control algorithm was based on physiology, and the parameters of the model were estimated in real-time. The framework provided a mechanism to account for inter-patient and intra-patient variability in the fluid resuscitation process.

Figure 10:
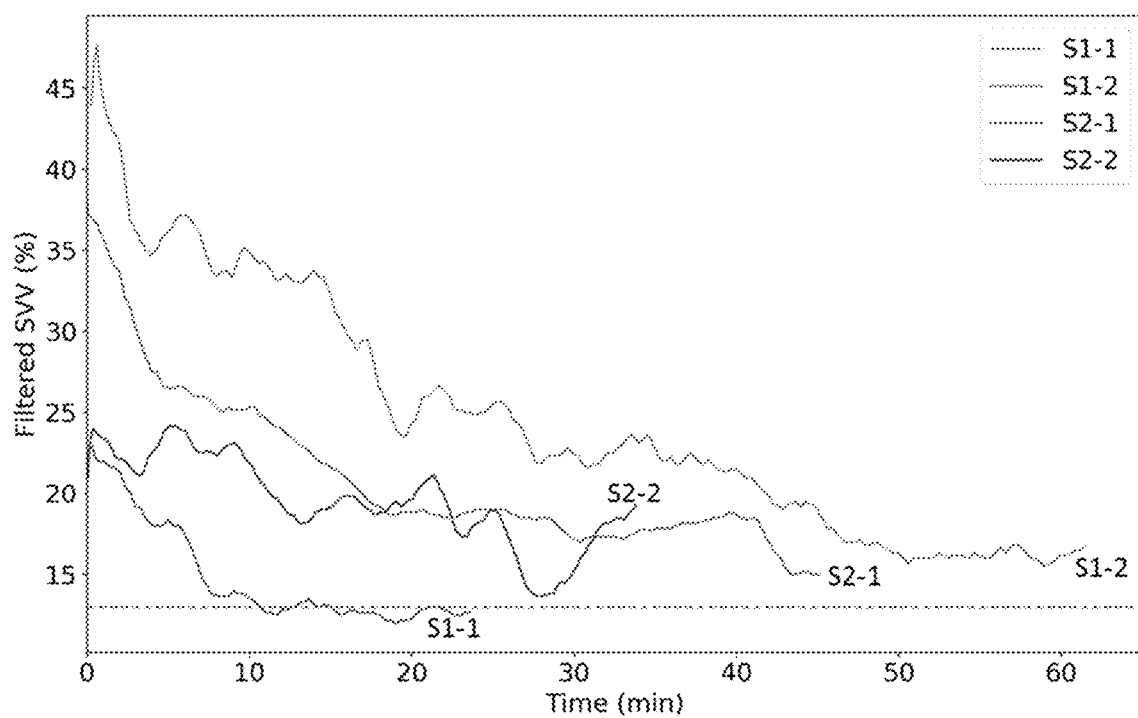
FIG. 10 is a graph that depicts exemplary changes in filtered SVV (%) in 2 canine subjects experiencing controlled hemorrhage.
Figure 11:
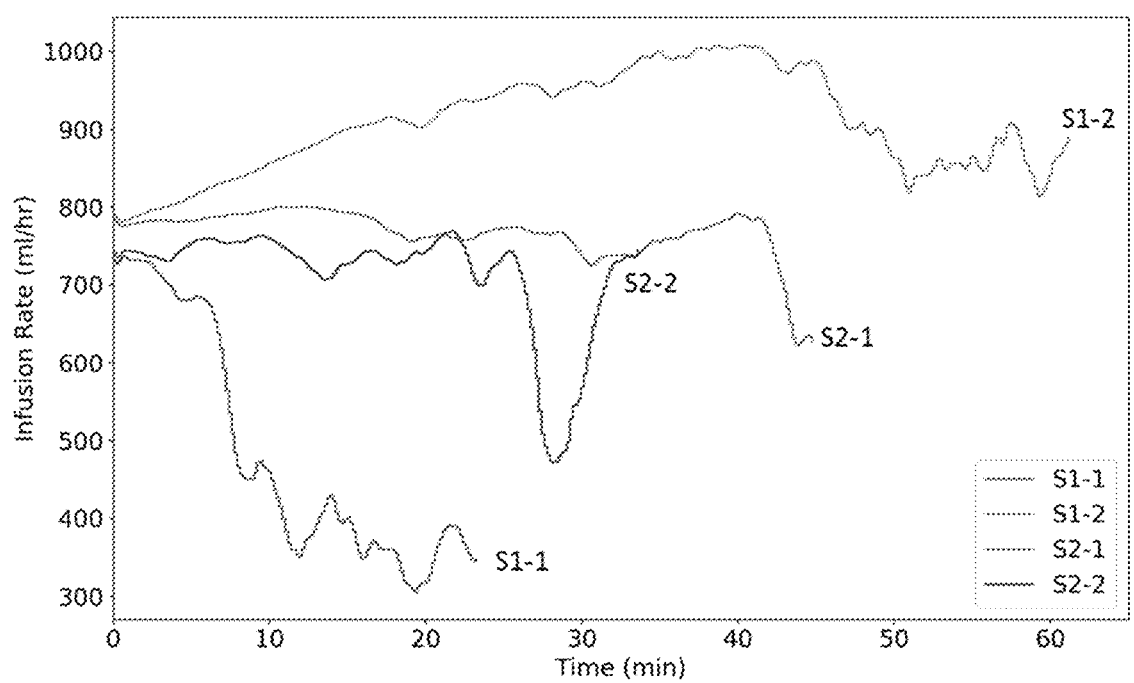
FIG. 11 is a graph that depicts exemplary changes in infusion rates in 2 canine subjects experiencing controlled hemorrhage.

FIGS. 10 and 11 show the results for 2 canine subjects S1 and S2 (total of 4 studies) experiencing controlled hemorrhage. FIG. 10 shows changes in filtered SVV (%) versus time, and FIG. 11 shows changes in infusion rate (mL/hr) versus time. The target SVV was 13%. In study S1-1, the infusion rate dropped from 750 mL/hr to about 400 mL/hr to maintain an SVV of 13%. Once reaching the target SVV (%), the infusion rate fluctuated between 300-400 mL/hr to maintain an SVV of 13% In study S1-2, the infusion rate started from about 800 mL/hr increased to about 1000 ml/hr and decreased to about 850 ml/hr. In study S2-1, the infusion rate started from about 800 mL/hr and in the end reached about 650 ml/hr. In study S2-2, the infusion rate started from about 750 mL/hr and in about 30 minutes reached about 500 ml/hr but increased to 750 ml/hr.

Figure 12:
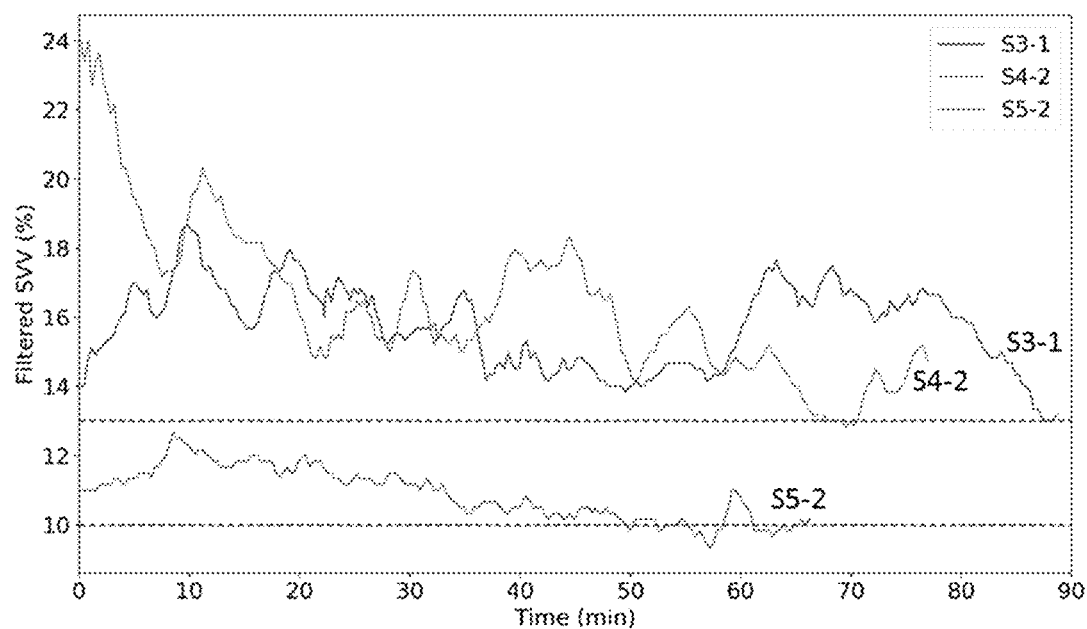
FIG. 12 is a graph that depicts exemplary changes in filtered SVV (%) in 3 canine subjects experiencing uncontrolled hemorrhage.
Figure 13:
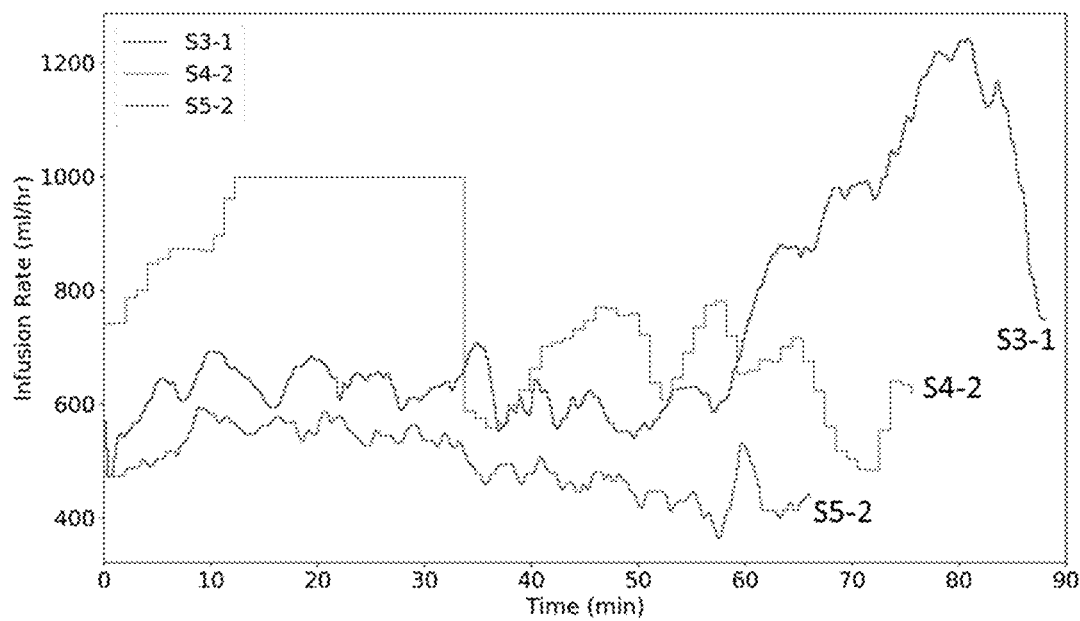
FIG. 13 is a graph that depicts exemplary changes in infusion rates in 3 canine subjects experiencing uncontrolled hemorrhage.

FIGS. 12 and 13 shows the results for 3 canine subjects S3, S4, and S5 experiencing uncontrolled hemorrhage. FIG. 12 shows changes in filtered SVV (%) versus time, and FIG. 13 shows changes in infusion rate versus time. The target SVV was 13% in studies S3-1 and S4-2 and was 10% in study S5-2. In study S4-2, the partial automation (clinical decision support) was used where every 1 minute the clinician used fluid rates recommended by the system to manually change the infusion rate on the pump. In the other two studies S3-1 and S5-2 the fully automated closed-loop system was used. In study S3-1, the infusion rate started from about 600 mL/hr and increased to about 1200 mL/hr to drive SVV to 13% and then dropped to 750 mL/hr. In study S4-2, the infusion rate started from about 750 mL/hr increased to 999 mL/hr and then decreased to about 600 mL/hr to drive SVV to 13%. In study S5-2, the infusion rate started from about 500 mL/hr and fluctuated between 400-600 mL/hr to drive SVV to the target value of 10%.

Figure 14:
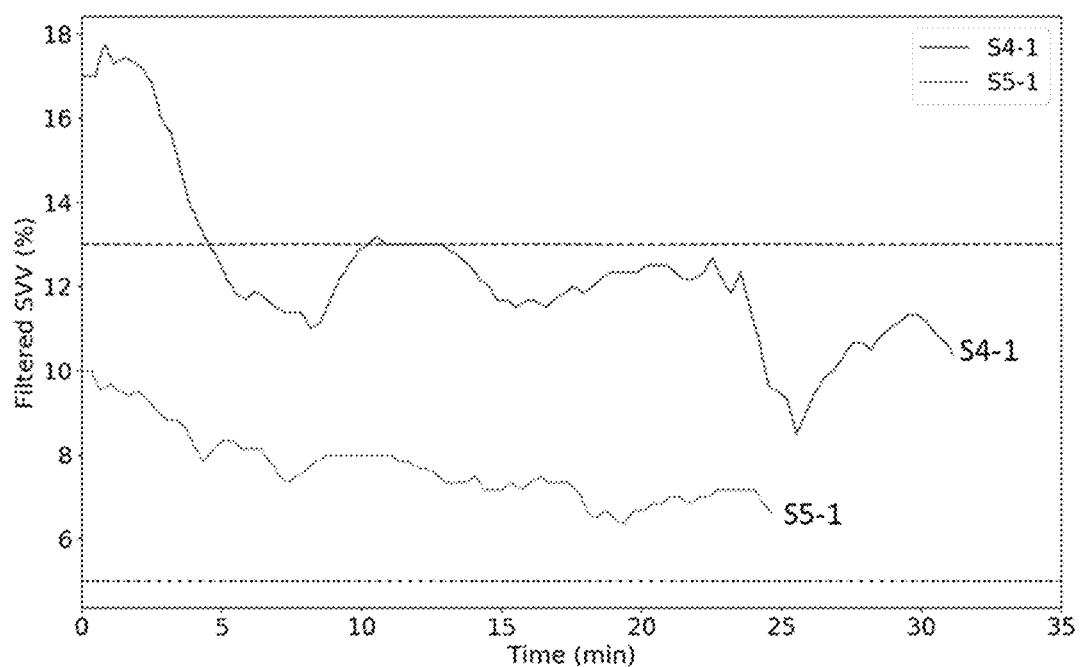
FIG. 14 is a graph that depicts exemplary changes in filtered SVV (%) in 2 canine subjects that were hypotensive as a result of administration of sodium nitroprusside (S4-1) and increase in isoflurane (S5-1).
Figure 15:
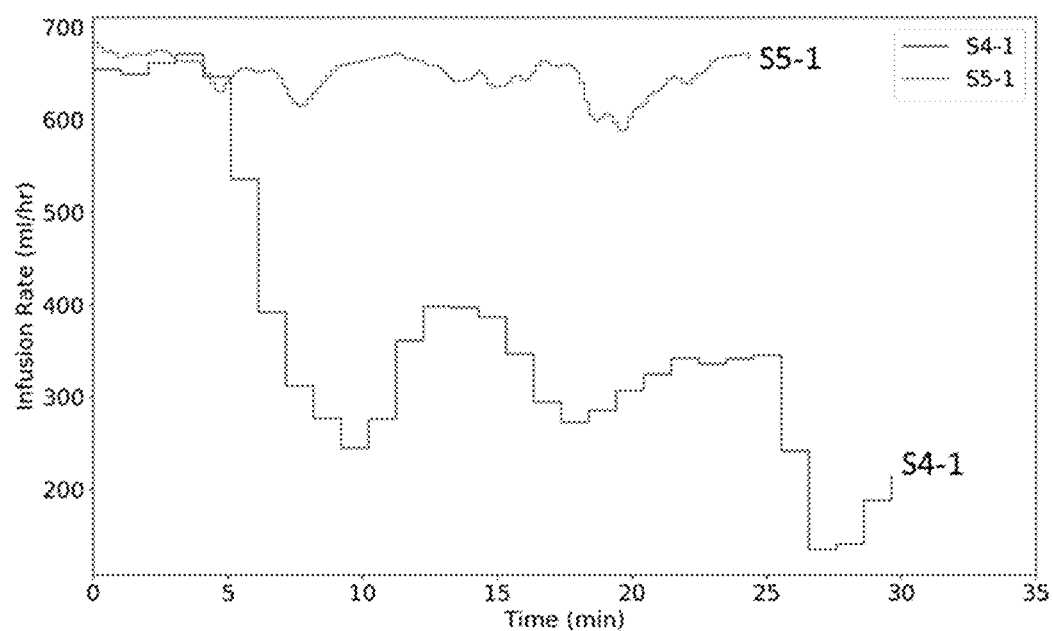
FIG. 15 is a graph that depicts exemplary changes in infusion rates in 2 canine subjects that were hypotensive as a result of administration of sodium nitroprusside (S4-1) and increase in isoflurane (S5-1).

FIGS. 14 and 15 shows the fluid resuscitation of 2 canine subjects S4 and S5 that were hypotensive as a result of administration of sodium nitroprusside (in S4-1) and increase in the inhalant anesthetic isoflurane (in S5-1). In study S5-1, the fully automated closed-loop system was used while in study S4-1 the partially automated (clinical decision support) system was used where the recommended infusion rate was displayed every 1 minute to the user and the user changed the infusion rate on the pump manually. FIG. 14 shows changes in filtered SVV (%) versus time, and FIG. 15 shows changes in infusion rate versus time. The target SVV was 13% in S4-1 and 5% in S5-1. In S4-1, the infusion rate was started at about 650 mL/hr and decreased to between 150-350 mL/hr once the target 13% was reached. In S5-1, the infusion rate started at about 700 mL/hr and was kept close to this value until 25 minutes into the study, when the study was terminated as SVV approached the desired SVV of 5%.

Example 6: Higher-Level Controller

The higher-level controller was designed as a rule-based expert system and served to:

i) monitor the lower-level controller (fluid resuscitation module and/or cardiovascular drug administration module) function for possible anomalies;

ii) monitor the patient's general status and response to fluid therapy and/or cardiovascular drug administration;

iii) in the case of closed-loop mode decide to engage fluid resuscitation module, cardiovascular drug administration module, or both, and the timing of engagement of the modules;

iv) handle scenarios related to sensor failure or infusion rate exceeding maximum safe limit;

v) modify the lower-level controller (fluid resuscitation module or cardiovascular drug administration module) states in the case of clinical decision support if the user disagrees with the computed infusion rate;

vi) provide clinical decision support to address potential problems; and vii) in clinical decision support mode, notifying the user with the new infusion rate when the infusion rate needs to be updated.

Maintaining Infusion Rate in Safe Range. If the computed infusion rate by the lower-level controller (fluid resuscitation module and/or cardiovascular drug administration module) was larger than the maximum safe rate specified by the user, the higher-level controller reset the lower-level controller associated with unallowable infusion rate, that is, it reinitialized the internal states of the lower-level controller including function approximator weights (or coefficients) to the default values (i.e., changed $w_p$, $w_q$, and $x_c$ to their values at t=0).

Warning the User. If the total volume delivered to the patient exceeded a set threshold (e.g., 2000 mL or 10,000 mcg), the higher-level controller warned the user of the risk of complications.

Monitoring the Lower-Level Controller. If performance degradation in the closed-loop system was detected, the higher-level controller notified the user through an audio-visual alarm, and the higher-level controller stopped the lower-level controller. Performance degradation was defined as: i) a rapid change in weights (or coefficients) of the function approximator, that is, $$\frac{d|W|}{dt} > \text{threshold}$$

(e.g., 0.1, or 1, 10 etc.); or ii) the number of resets of the lower-level controller by the higher-level controller exceeding a threshold value (e.g., 1, 2, 3, 4, etc.), or iii) the absolute difference between the measured value (e.g., SVV or mean arterial pressure) and the target value did not decrease in a period of time set by user while the infusion was continuously increased. In case of sensor failure or unavailability of measurements, the higher-level controller disabled the lower-level controller and set the infusion rate to a backup the infusion rate set by the user.

Deciding When to Engage Fluid Resuscitation and Cardiovascular Drug Administration Modules. In certain scenarios such as sepsis, it is preferable to provide fluid resuscitation first, and if unsuccessful in achieving an acceptable condition, administer a cardiovascular drug such as a vasopressor. The higher-level controller first engaged the fluid resuscitation module and monitored the patient. After a period of time when a clinically relevant hemodynamic variable (e.g., mean arterial pressure) was not improved in spite of fluid resuscitation (e.g., the mean arterial pressure was not in the acceptable range of 65-80 mmHg after 30 minutes), the higher-level controller engaged the cardiovascular drug administration module to administer a vasopressor. In some embodiments, the clinician instructed the higher-level controller to engage the cardiovascular drug administration module while the fluid resuscitation module was already running. In some embodiments, the clinician instructed the higher-level controller to engage the fluid resuscitation module while the cardiovascular drug administration module was already running. In this scenario, stroke volume variation was not improved by only administering a cardiovascular drug (e.g., a vasopressor) and the higher-level controller engaged the fluid resuscitation module.

Figure 16:
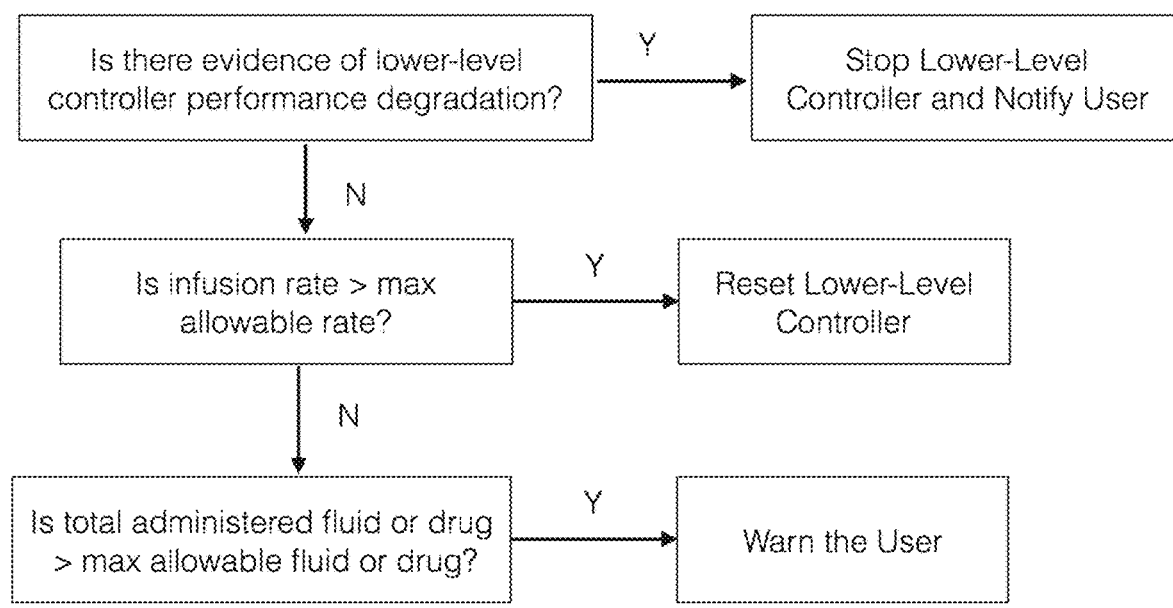
FIG. 16 is a flow chart that illustrates components of the higher-level controller for the closed-loop fluid resuscitation system in embodiments.

FIG. 16 illustrates the components of the higher-level controller for the closed-loop fluid resuscitation and/or cardiovascular drug administration system. The higher-level controller can monitor the fluid resuscitation module and/or the cardiovascular drug administration depending on whether the system is used for fluid resuscitation only, for cardiovascular drug administration only, or combined fluid resuscitation and cardiovascular drug administration.

In the clinical decision support system case, the lower-level controller (fluid resuscitation module or cardiovascular drug administration module or both) sent newly computed infusion rate to the higher-level controller. Specifically, we considered 3 scenarios: i) fluid resuscitation module only; ii) cardiovascular drug administration module only; and iii) fluid resuscitation module and cardiovascular drug administration module working concurrently. In each scenario, the lower-level controller sent newly computed infusion rate to the higher-level controller. The higher-level controller compared the new rate with the last user approved rate (i.e., for a fluid resuscitation, the newly computed fluid infusion rate was compared with the last user-approved fluid infusion rate, and for cardiovascular drug administration, drug infusion rate was compared with the last user-approved drug infusion rate).

If the difference between the new infusion rate and the last user-approved rate was less than the threshold value (e.g., 25% of the last approved rate), then the infusion rate was not changed, the user was not notified, and the lower-level controller continued its operation. If the difference between the new infusion rate and the last user-approved rate was higher than some threshold (e.g., 25% of the last approved rate), then the recommended infusion rate was displayed to the user through the graphical user interface. If the user accepted the infusion rate, the higher-level controller allowed the lower-level controller to continue its operation and the infusion rate was updated to the new rate. However, if the user changed the recommended infusion rate to a different value, the higher-level controller reset the controller and set the weights of the function approximator such that the infusion rate computed by the lower-level controller matched the infusion rate entered by the user. The infusion rate was also updated to the rate provided by the user. Given the user specified infusion rate, the weights of the function approximator was chosen such that $$w_{q,new}(0) = w_q(0)$$

$$w_{p,new}^T(0)P(z(0)) = (\text{new infusion})(1 + w_q^T(0)Q(z(0)))$$

Figure 17:
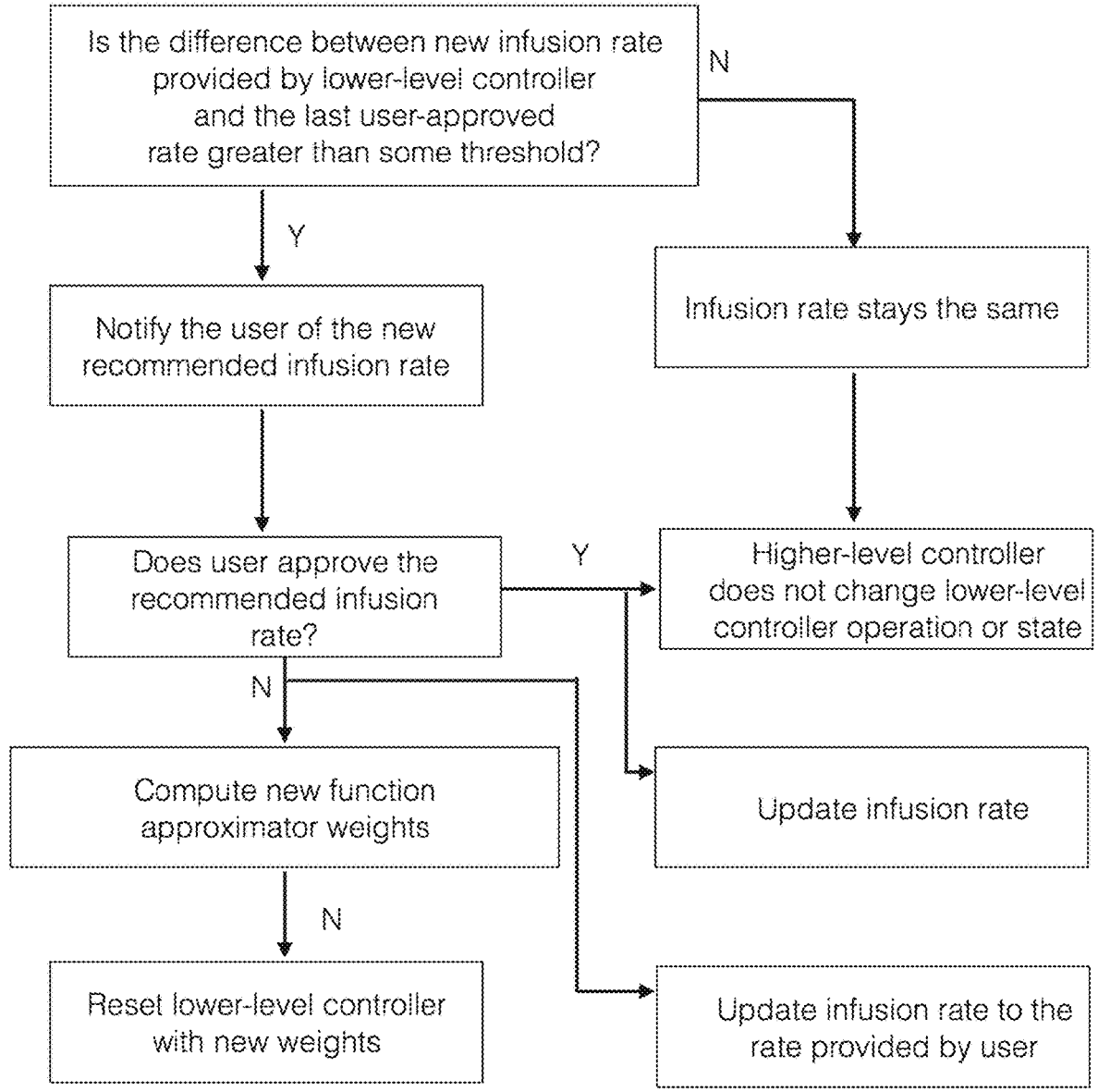
FIG. 17 is a flow chart that illustrates components of the higher-level controller for the clinical decision support case in embodiments.

FIG. 17 illustrates the components of the higher-level controller for the clinical decision support case.

Example 7: Computer Simulations for Vasopressor Administration

Adaptive control frameworks were used to simulate cardiovascular drug (vasopressor) administration of a 70 kg patient experiencing sepsis and the associated hypotension. The goal was to maintain the mean arterial pressure at 65. A $\Delta t$ of 0.1 minute (6 seconds) was used for the simulations and $\beta_1 = 6\text{e-}5$, $\beta_2 = 13\text{e-}6$, and $n_{node}$ 8. Only the vasopressor was administered to maintain a mean arterial pressure of 75 mmHg. The patient model involved a cardiovascular model to model hemodynamics and a compartmental model to model fluid distribution.

Figure 18:
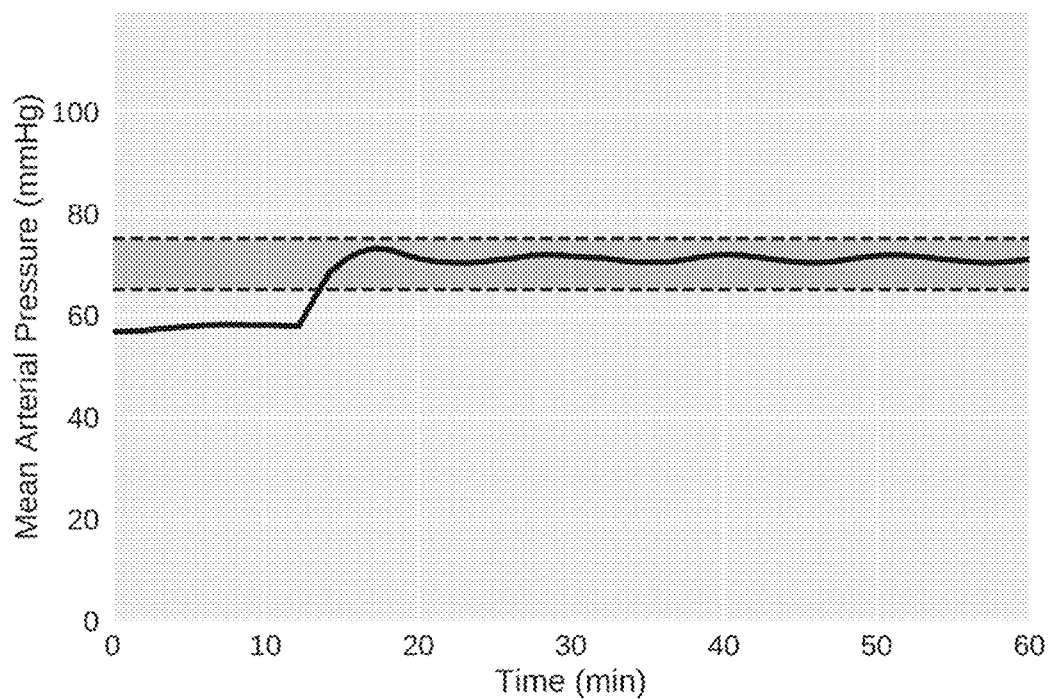
FIG. 18 is a graph that depicts exemplary mean arterial pressure versus time.

FIG. 18 shows mean arterial pressure (MAP) versus time. The target MAP was 75 mmHg, and the 65-75 mmHg region is highlighted on the graph. MAP started at below 60 mmHg, and changes with the introduction of vasopressor epinephrine. The MAP increased to the target value of 75 mmHg.

Figure 19:
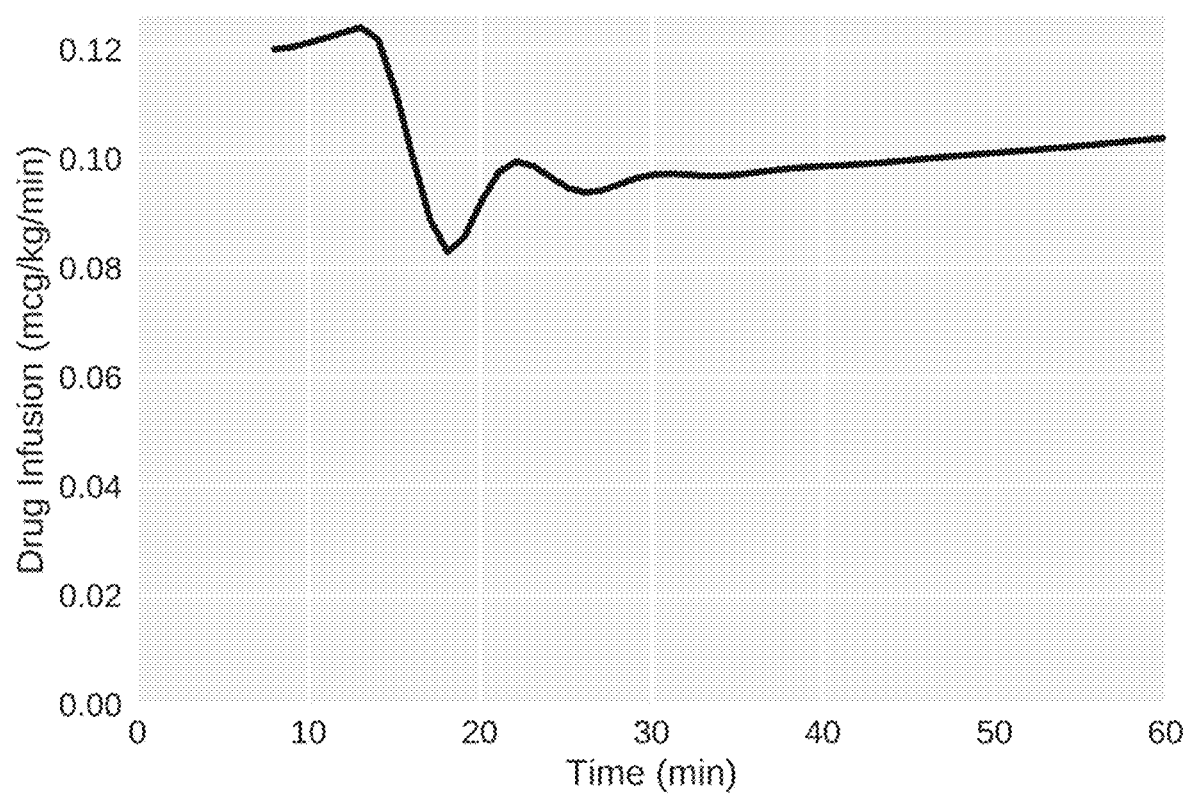
FIG. 19 is a graph that depicts exemplary cardiovascular drug infusion rates computed by the adaptive control framework.

FIG. 19 shows infusion rates computed by the adaptive control framework. The initial infusion rate was chosen by the user to be 0.12 mcg/kg/min at t=8 (start of the vasopressor administration). The infusion rate gradually increased and then started to decrease as MAP started to approach the target MAP of 75 mmHg reaching a low infusion rate of 0.85 mcg/kg/min. The infusion rate then started to gradually increase to maintain MAP of 75 mmHg.

Example 8: Computer Simulations for Fluid Administration Using Mean Arterial Pressure Adaptive control frameworks were used to simulate fluid resuscitation of a 70 kg patient with hypotension as a result of sepsis. The goal was to maintain the mean arterial pressure at 75 mmHg. A $\Delta t$ of 0.1 minute (6 seconds) was used for the simulations and $\beta_1 = 0.02$, $\beta_2 = 0.04$, and $n_{node} = 8$. The patient model involved cardiovascular modeling to model hemodynamics and a compartmental model to model fluid distribution.

Figure 20:
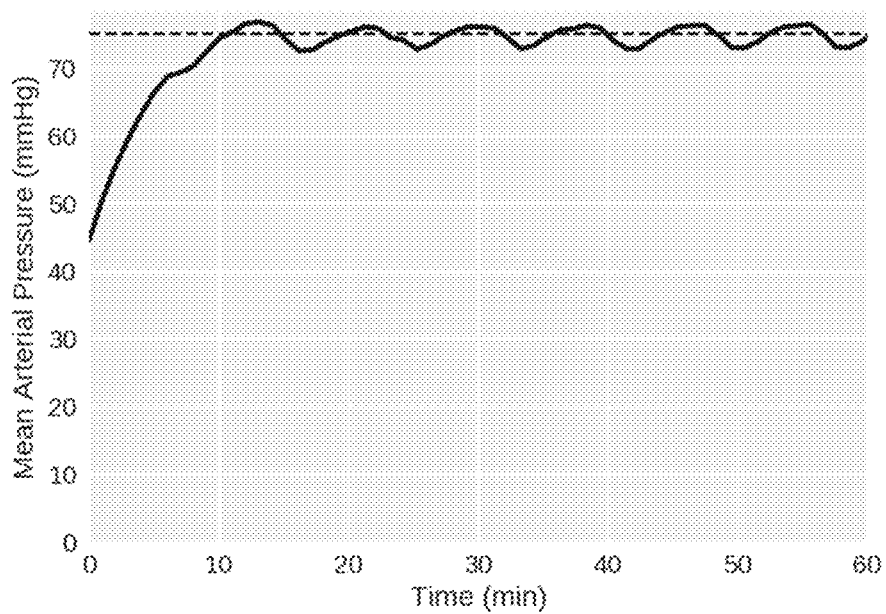
FIG. 20 is a graph that depicts exemplary mean arterial pressure versus time.

FIG. 20 shows mean arterial pressure (MAP) versus time. The target MAP is 75 mmHg and the 65-75 mmHg region is highlighted on the graph. MAP starts at approximately 45 mmHg, and changes with the introduction of crystalloid fluid. The MAP increases to the target value of 75 mmHg.

Figure 21:
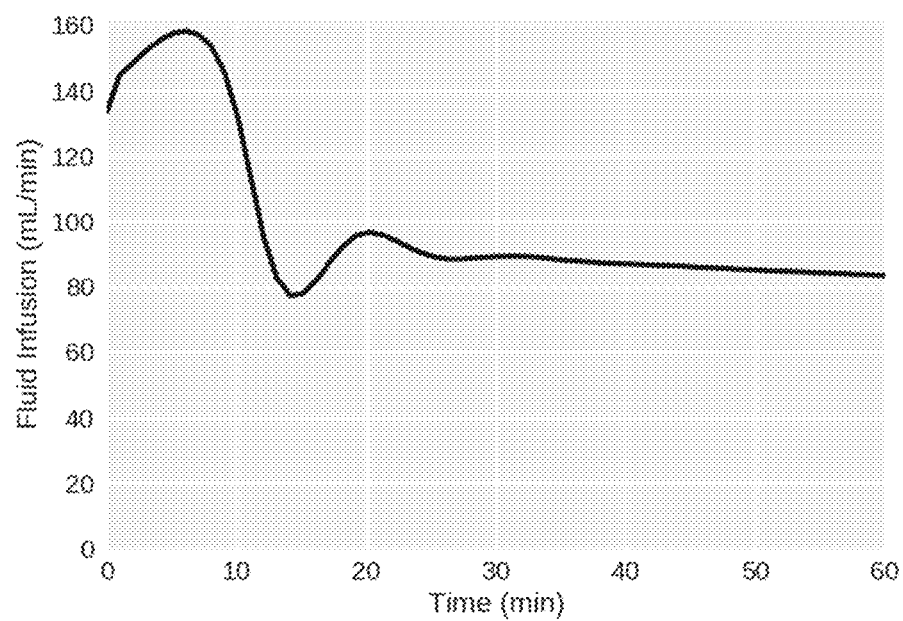
FIG. 21 is a graph that depicts exemplary fluid infusion rates computed by the adaptive control framework.

FIG. 21 shows infusion rates computed by the adaptive control framework. The initial infusion rate was chosen was approximately 140 mL/min. The infusion rate gradually increased to 160 mL/min and then decreased to around 80 ml/min.

Example 9: Computer Simulations for Fluid Administration and Cardiovascular Drug Administration Adaptive control frameworks were used to simulate fluid resuscitation and cardiovascular drug (vasopressor epinephrine) administration for a 70 kg patient with hypotension as a result of sepsis. The goal was to maintain the mean arterial pressure at 75 mmHg and stroke volume variation (SVV) of 12%. A $\Delta t$ of 0.1 min (6 seconds) was used for the simulations and $\beta_1=0.02$, $\beta_2=0.04$, and $n_{node}=8$ for the fluid resuscitation module and $\beta_1=6e-5$, $\beta_2=13e-6$, and $n_{node}=8$ for the cardiovascular drug administration module. The simulation involved crystalloid fluid and epinephrine (vasopressor). The fluid resuscitation module used SVV data to compute fluid infusion rates, and the cardiovascular drug administration module used mean arterial pressure (MAP) to compute the vasopressor infusion rates. The higher-level controller first engaged the fluid resuscitation module to provide fluid infusion. After 30 minutes, the higher-level controller engaged the cardiovascular drug administration module as mean arterial pressure was not improved after fluid infusion. The patient model involved cardiovascular modeling to model hemodynamics and compartmental model to model fluid distribution. The start of simulation is when the patient condition rapidly deteriorates.

Figure 22:
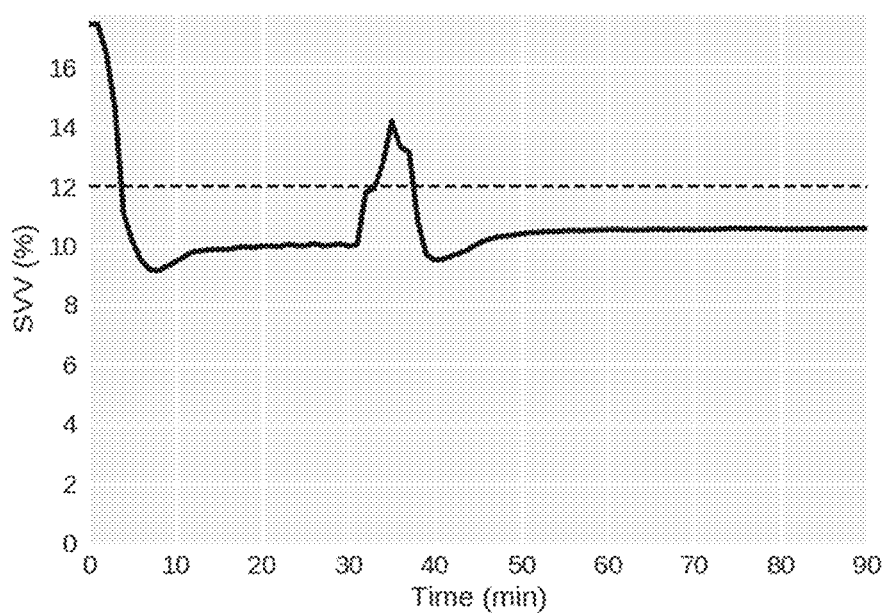
FIG. 22 is a graph that depicts exemplary stroke volume variation versus time.

FIG. 22 shows stroke volume variation (SVV (%)) versus time. The target stroke volume variation was 12%. The SVV (%) started at about 18%, and was reduced to 10% after fluid resuscitation. SVV momentarily increased due to the administration of epinephrine (a transient vasodilatory effect). In the end of the simulation, SVV was approximately 11% and remained close to the target SVV value of 12%.

Figure 23:
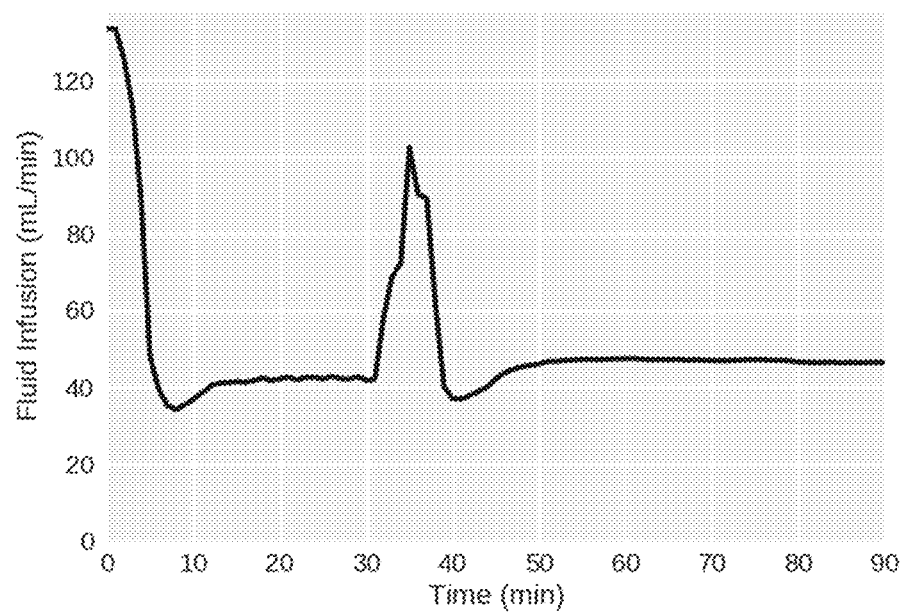
FIG. 23 is a graph that depicts exemplary fluid infusion rates computed by the fluid resuscitation adaptive control framework.

FIG. 23 shows fluid infusion rates computed by the fluid resuscitation adaptive control framework. The infusion rate started at approximately 130 mL/min and was reduced to 40 mL/min after SVV was at an acceptable range. The sudden increase in SVV at t=30 min resulted in an increase in infusion rate which then reduced back to 40 mL/min after SVV was reduced.

Figure 24:
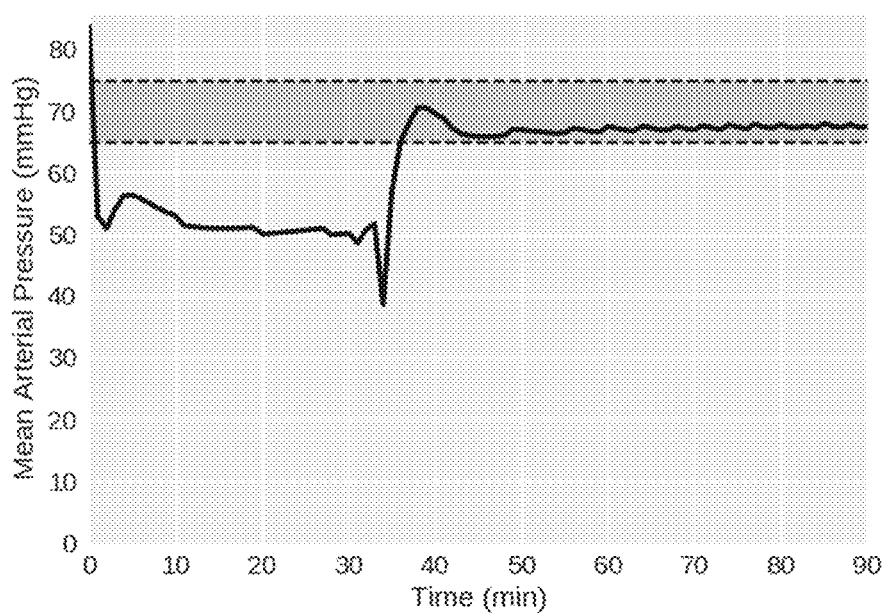
FIG. 24 is a graph that depicts exemplary mean arterial pressure versus time.

FIG. 24 shows mean arterial pressure (MAP) versus time. The target MAP was 75 mmHg and the 65-75 mmHg region is highlighted on the graph. MAP dropped to 50 mmHg as the patient condition deteriorated. After 30 minutes, when the cardiovascular drug administration module was engaged by the higher-level controller, MAP started to increase and approached the set value of 75 mmHg. At the end of the simulation, MAP was approximately 70 mmHg and remained close to the target MAP value of 75 mmHg.

Figure 25:
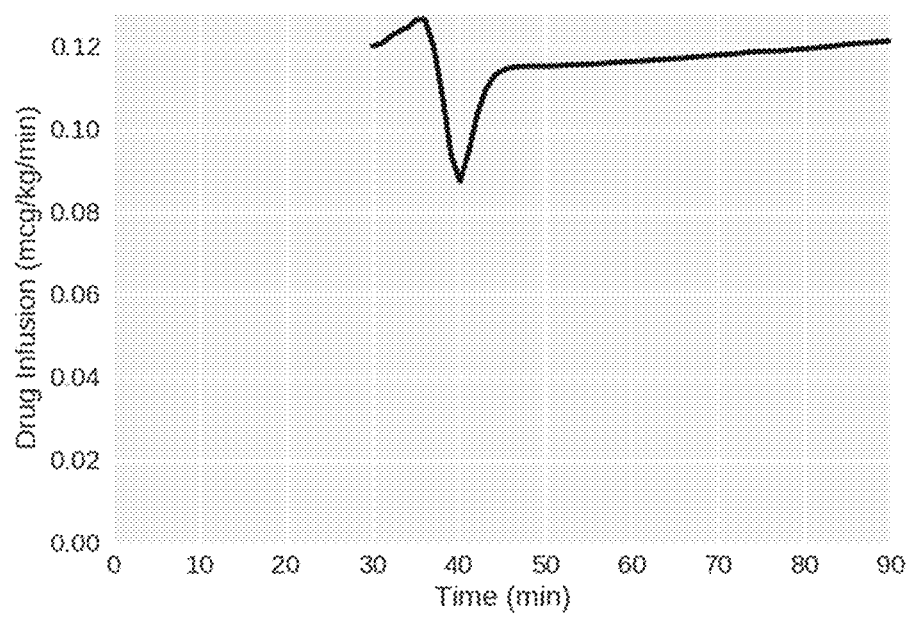
FIG. 25 is a graph that depicts exemplary vasopressor infusion rates computed by the cardiovascular drug administration adaptive control framework.

FIG. 25 shows vasopressor infusion rates computed by the cardiovascular administration adaptive control framework. The initial infusion rate was chosen to be approximately 0.12 mcg/kg/min. After a slight increase, the rate decreased to approximately 0.9 mcg/kg/min and then stabilized around 0.12 mcg/kg/min as MAP is maintained close to 70 mmHg.

Example 10: Fluid Resuscitation and Cardiovascular Drug Administration System Implemented on Hardware A hardware platform was developed to implement the fluid resuscitation system and the cardiovascular drug administration system. The system is composed of a processing module and an associated touchscreen. The processing module is able to receive data from a hemodynamic monitor (invasive or non-invasive measurement) or a blood pressure module (either invasive measurement through a pressure transducer connected to an arterial line or non-invasive measurement) through a wired connection. In addition, the processing module is able to send real-time infusion rate data through a wired connection to an infusion pump. The touchscreen is used for displaying graphs such as received measurements over time and infusion rate over time. The main dashboard also displays current measurement, current infusion rate, and total volume of fluid/drug infused. The touchscreen allows the user to specify different parameters required by the system. For example, the user sets the target measurement value, initial infusion rate, backup infusion rate (in case of missing sensor data, the closed-loop system is disengaged and transitions to backup infusion rate until the user takes over) maximum infusion rate and other variables. In the case of clinical decision support, the touchscreen is used to communicate the new infusion rate value to request user's approval or give the user the ability to modify the rate. Once the user approves the infusion rate, the processing module updates the infusion rate of the infusion pump to the infusion rate approved by the user.

Figure 26:
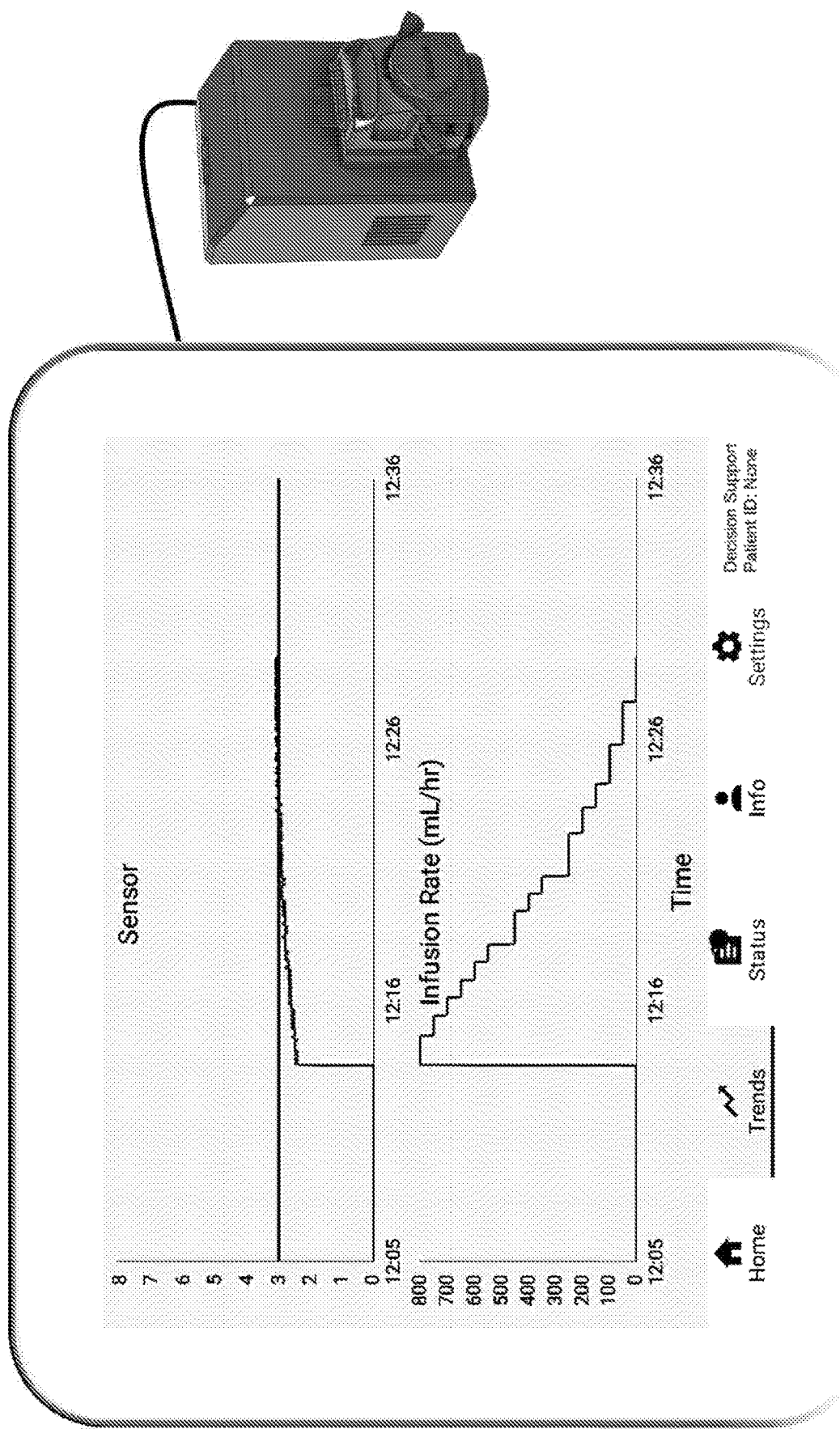
FIG. 26 is a diagram that depicts an embodiment of a fluid resuscitation and cardiovascular drug administration system implemented on hardware.

FIG. 26 is a system diagram of an embodiment of the hardware platform.

Figure 27:
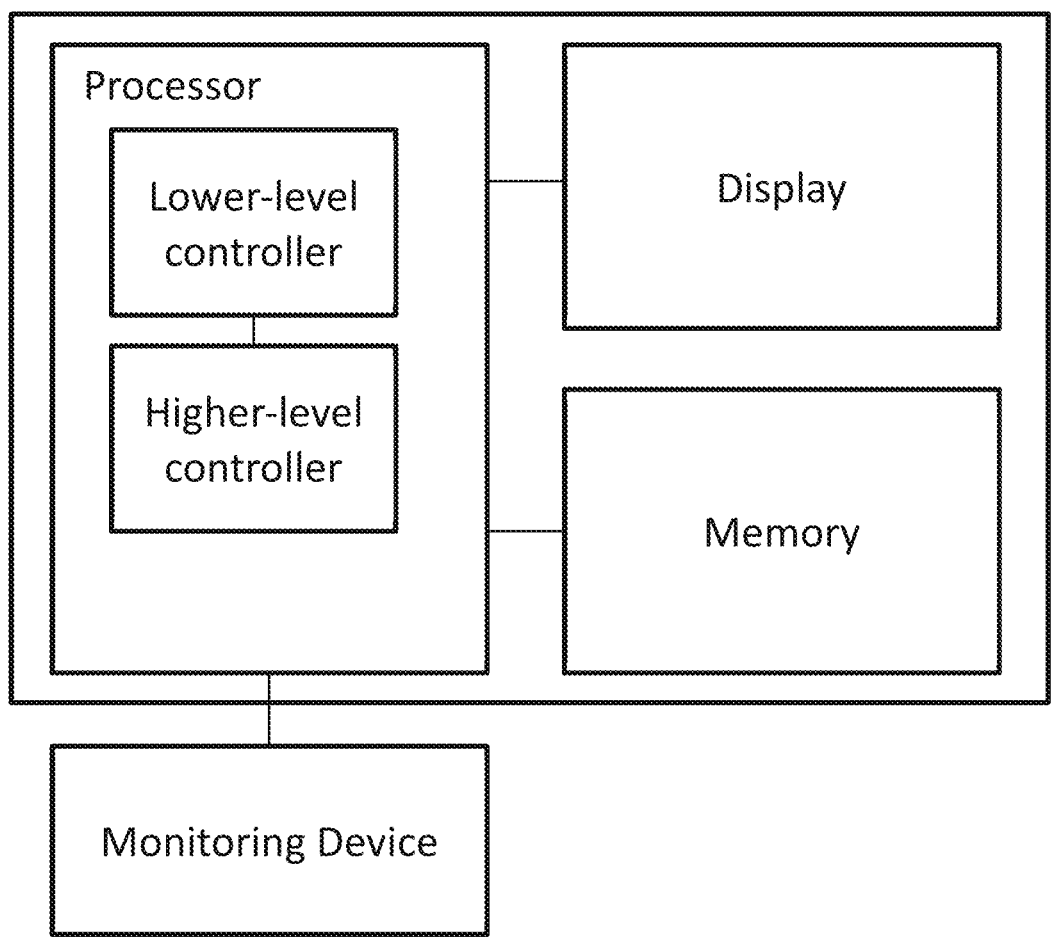
FIG. 27 is a block diagram illustrating an embodiment of the apparatus for displaying infusion therapy information for optimizing infusion therapy.
Figure 28:
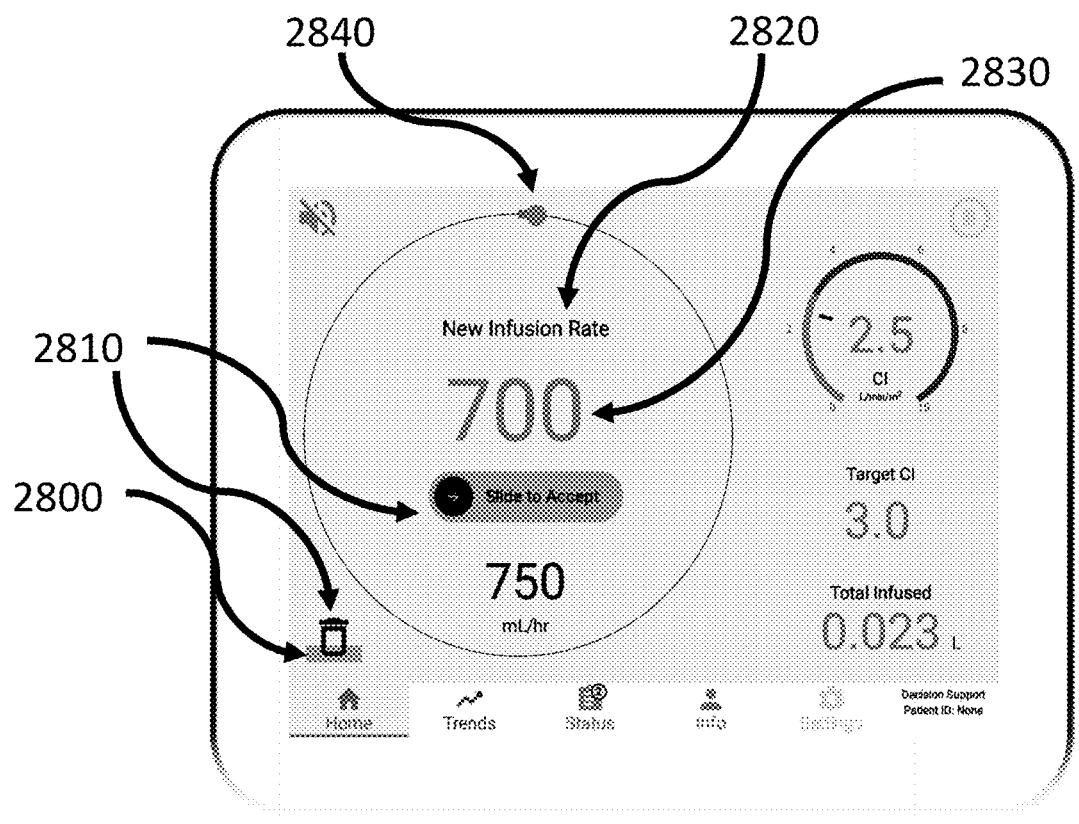
FIG. 28 is a diagram that depicts an embodiment of the apparatus for displaying infusion therapy information for optimizing infusion therapy.

FIG. 27 is a block diagram illustrating an embodiment of the apparatus for displaying infusion therapy information for optimizing infusion therapy. FIG. 28 depicts an embodiment of the apparatus for displaying infusion therapy information for optimizing infusion therapy. The apparatus comprises a memory, a display, and one or more processor in operable communication with the memory and the display. The processor is capable of receiving sensor-obtained hemodynamic measurements of a subject from a hemodynamic monitoring device. The processor is further capable of issuing a prompt to the display upon determining an appropriate notification message and an appropriate change in infusion rate recommendation message, which are implicated upon detection of a change in infusion therapy. The detection of a change in infusion therapy is based at least on hemodynamic measurements of a subject, an active infusion rate stored in the memory, and a background infusion rate computed by a lower-level controller.

In some embodiments, an active infusion rate is a last user-approved infusion rate. The last-approved infusion rate can be a last infusion rate that was recommended through a prompt and accepted by a user. In other embodiments, an active infusion rate can be an infusion rate obtained from an infusion pump that is actively administering fluid into a subject. A background infusion rate is an infusion rate that upon updates to its value does not actively change the infusion rate of fluid or drug administered to a subject, but rather it updates in the background. In some embodiments, a background infusion rate is computed by a lower-level controller. In other embodiments, the background infusion rate can take on the value of an active infusion rate. This may be through mechanisms such as a rejection of a recommended infusion rate prompted to a user which permits the user to manually override the recommendation with a desired infusion rate. In this example, the desired infusion rate would become an active infusion rate and the background infusion rate, at least momentarily, would take on the value of this set desired infusion rate.

An appropriate notification message can alert a user that a new recommended infusion rate is available. In other embodiments, the notification message can alert a user that subject being treated with the infusion therapy is not improving based upon hemodynamic measurements. In yet another embodiment, the notification message can alert a user of a failure in receiving hemodynamic measurements from a monitoring device. In other embodiments, this notification message can alert a user of a failure in administering fluid, for instance, due to a status message received from an infusion pump. In other embodiments, the notification message can alert the user that received hemodynamic measurements exceed, equal, or drop below some threshold.

An appropriate change in infusion rate recommendation message can be a recommendation to increase or decrease the current active infusion rate. In other embodiments, an appropriate change in infusion rate recommendation message can be a specific value for infusion rate (e.g. 700 mL/hr, 300 mL/hr, 0 mL/hr). In one embodiment, this specific value can be 0 mL/hr, that is, to stop infusion of fluids or drugs to a patient, if an associated notification message alerts the user that the hemodynamic condition of a subject is not improving; in another embodiment, the recommendation to stop infusion of fluids or drugs may be due to an associated notification message that alerts the user that some hemodynamic measurement exceeds or drops below some threshold.

In some embodiments, the notification message is generated only if the absolute difference between the active infusion rate and the background infusion rate is larger than a pre-determined threshold. In case the absolute difference between the active infusion rate and the background infusion rate is less than the pre-determined threshold then the value of the background infusion rate is ignored and the lower-level controller continues with computing new background infusion rates until the criterion for notifying the user is met. In some embodiments, the pre-determined threshold is a percentage of the active infusion rate (e.g, 1%, 2%, 5%, 10%). In other embodiments, the pre-determined threshold is an absolute value (e.g., 0.001 ml/hr, 0.1 ml/hr, 1 ml/hr, 10 ml/hr, 100 ml/hr, 1000 ml/hr).

Referring again to FIG. 27, the display can be a touchscreen-based display in which a user can interact with any prompt through touch gestures. In other embodiments, the display can be a non-touchscreen display and the user can interact with any prompt with suitable input devices, such as physical buttons, a mouse/trackpad, a keypad/keyboard, etc.

A detection of a change in infusion therapy can be performed by the higher-level logic-based controller based upon the performance criteria discussed earlier. In some embodiments, the detection of a change in infusion therapy occurs when an active infusion rate and a background infusion rate differ in value by some percentage (e.g. 5%, 10%, 12%, etc.) of the active infusion rate, some percentage of the background infusion rate, or some percentage of the average of the active and background infusion rate; in other embodiments, the difference can be some absolute value (e.g. −50 mL/hr, 50 mL/hr, 100 mL/hr, etc.) which would trigger the detection.

Referring to FIG. 28, in some embodiments of the apparatus, upon issuance of a prompt 2810 that contains a slide to accept element or tap to reject element to the display containing a notification message 2820 and a change in infusion rate recommendation message 2830, there is a limited time for the user to respond with an acceptance or a rejection. If the user wishes to manually override the recommended infusion rate with a desired infusion rate, an infusion rate can be set with infusion meter slider 2840. However, if the user rejects using the reject/discard/trash button of 2810 or if the timer 2800 expires, the active infusion rate remains unchanged and the background infusion rate is set to the same value as the unchanged active infusion rate. If the recommended infusion rate is not accepted (e.g. due to manual override, rejection, or timer expiration), the higher-level logic controller resets at least one element of the set of weights of the lower-level controller to a new value based at least in part on the background infusion rate.

Fluid and/or Cardiovascular Drug Administration with Pre-Approved Ranges of Infusion Rates by the User The presented disclosure can be implemented in a way to minimize unnecessary interactions with the user regarding changes in infusion rates, which the user may deem acceptable or negligible. The advantage of this implementation is that the clinical decision support system has a specific level of autonomy to automatically change infusion rates as long as the infusion rates are within the pre-approved range specified by the user. In some embodiments, the clinical decision support system can be coupled to an internal or external infusion pump.

In some embodiments, the user can enter pre-approved ranges of infusion rates into the system with the intent that the system is authorized to change infusion rates automatically without requesting the user to approve the changes as long as the infusion rates fall within the pre-approved ranges. In some embodiments, the system automatically changes the infusion rate by instructing the pump and updating infusion rate on the graphical user interface as long as the new infusion rates are within the pre-approved infusion rates. In some embodiments, a pre-approved range can be entered using a lower limit and an upper limit (e.g., 50-100, 100-500, 500-1000 ml/hr).

In some embodiments, the approved range can be entered based on the last user-approved infusion rate. In this case, the user authorizes the clinical decision support system to internally approve infusion rates that are within a set distance (specified by the user) from the last user-approved infusion rate. For example, the user may authorize a pre-approved range of 500 ml/hr, in which case if the last user-approved infusion rate is 750 ml/hr the system is authorized to change the infusion rate as long as the new infusion rates are within 250 ml/hr to 1,250 ml/hr. In some embodiments, the user can specify a percentage change as a pre-approved range. For example, the user can approve a 10% change as a pre-approved range. In this case, if, for example, the last-approved infusion rate is 1,000 ml/hr, then the clinical decision support system can internally approve new infusion rates in the range 900 ml/hr to 1,100 ml/hr without requesting user's approval.

In some embodiments, the higher-level logic-based controller will compare the new infusion rate received from the lower-level controller with the pre-approved ranges. If the new infusion rate is within the pre-approved range (that is the new infusion rate is greater than or equal to the lower limit and less than or equal to the upper limit), then the higher-level logic can instruct the infusion pump to update the infusion rate to the new infusion rate value. However, if the new infusion rate falls outside the pre-approved range, the user is notified using the graphical user interface, where the user would approve, reject, or modify the new infusion rate.

Figure 29:
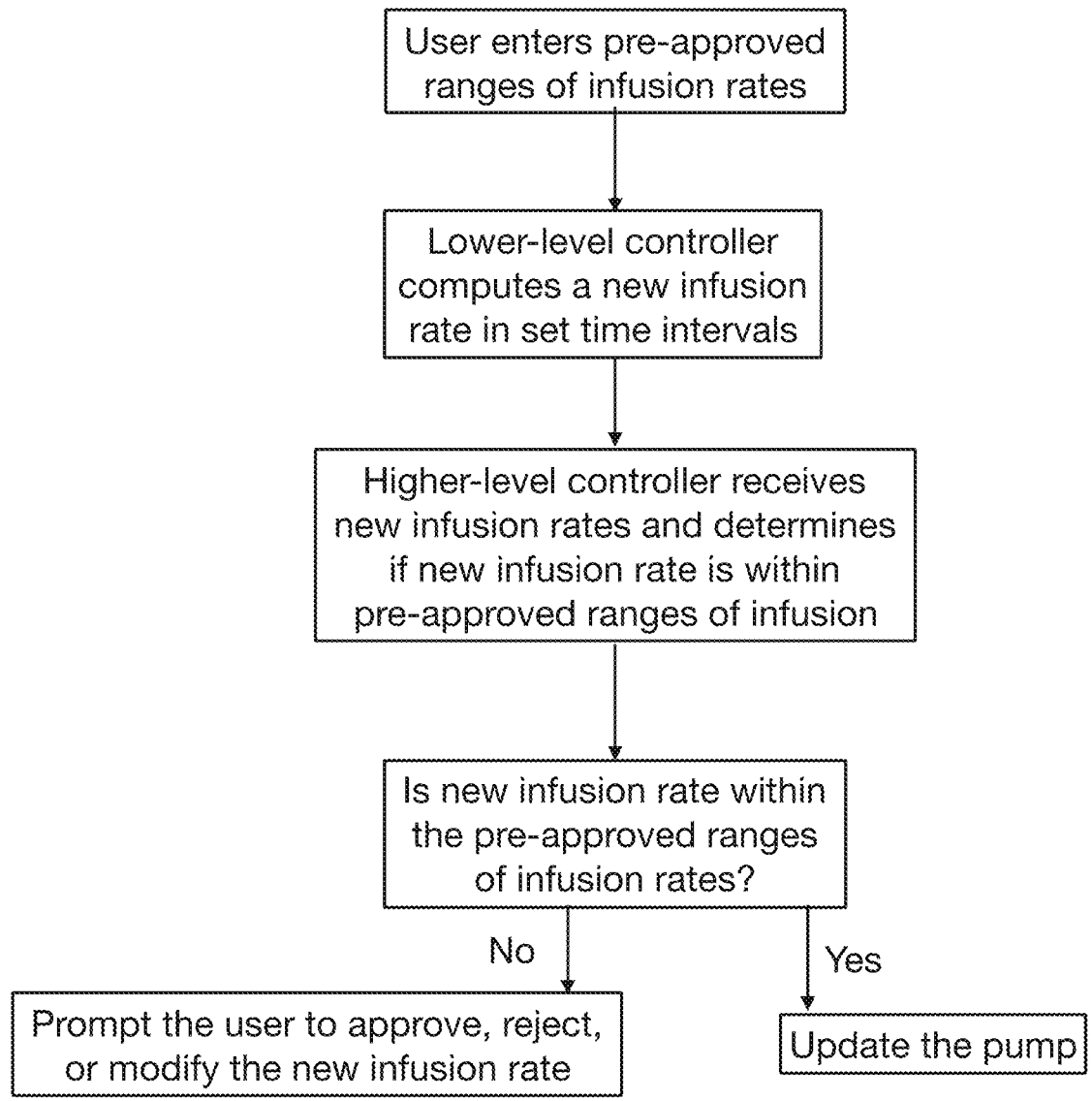
FIG. 29 is a flow chart that illustrates the administration of pre-approved ranges of infusion rates according to embodiments.

Referring to FIG. 29, a flow chart of the process is presented. The process starts by the user entering the pre-approved infusion rates into the system using the user interface. The lower-level controller computes new infusion rates based at least in part on hemodynamic measurements. The higher-level logic-based controller receives the newly computed infusion rates from the lower-level controller and determines whether the new infusion rate is within the pre-approved range. If so, it instructs the pump to update the infusion rate. Otherwise, it asks the user to approve, reject, or modify the new infusion rate.

Alarm Function to Prevent Under- or Over-Administration of Fluid and/or Drug

The hierarchical control system described in this disclosure can be used for monitoring therapy to a subject in order to flag cases where the subject would receive lower or higher than expected infusion of a fluid or cardiovascular drug. Both fluid and cardiovascular drug over-administration or under-administration is detrimental to the patient, and hence, a system that continuously monitors therapy including the infusion rate and patient's hemodynamic measurements and alerts the user if the patient is receiving more than expected or less than expected fluid and/or cardiovascular drug is desirable. In some embodiments, the system continuously monitors the patient's hemodynamic measurements, the type of therapy or therapies, and the infusion rate or infusion rates of the therapy or therapies, and notifies the user through a user interface if the patient is getting more than expected or less than expected fluid and/or cardiovascular drug. In some embodiment, this is implemented in a hemodynamic patient monitor at the bedside receiving information from the pump. In some embodiments, this is implemented as a software application as part of a remote patient monitoring platform, where information from hemodynamic monitors and infusion pumps are continuously analyzed and cases of over-administration or under-administration of fluid and/or cardiovascular drug is detected. In some embodiments, data from multiple hemodynamic monitors and infusion pump for different patients are all sent to the same remote location for analysis. In some embodiments, the system is implemented inside an infusion pump. In this case, the infusion pump receives hemodynamic measurement data from a hemodynamic monitor or other source.

Figure 30:
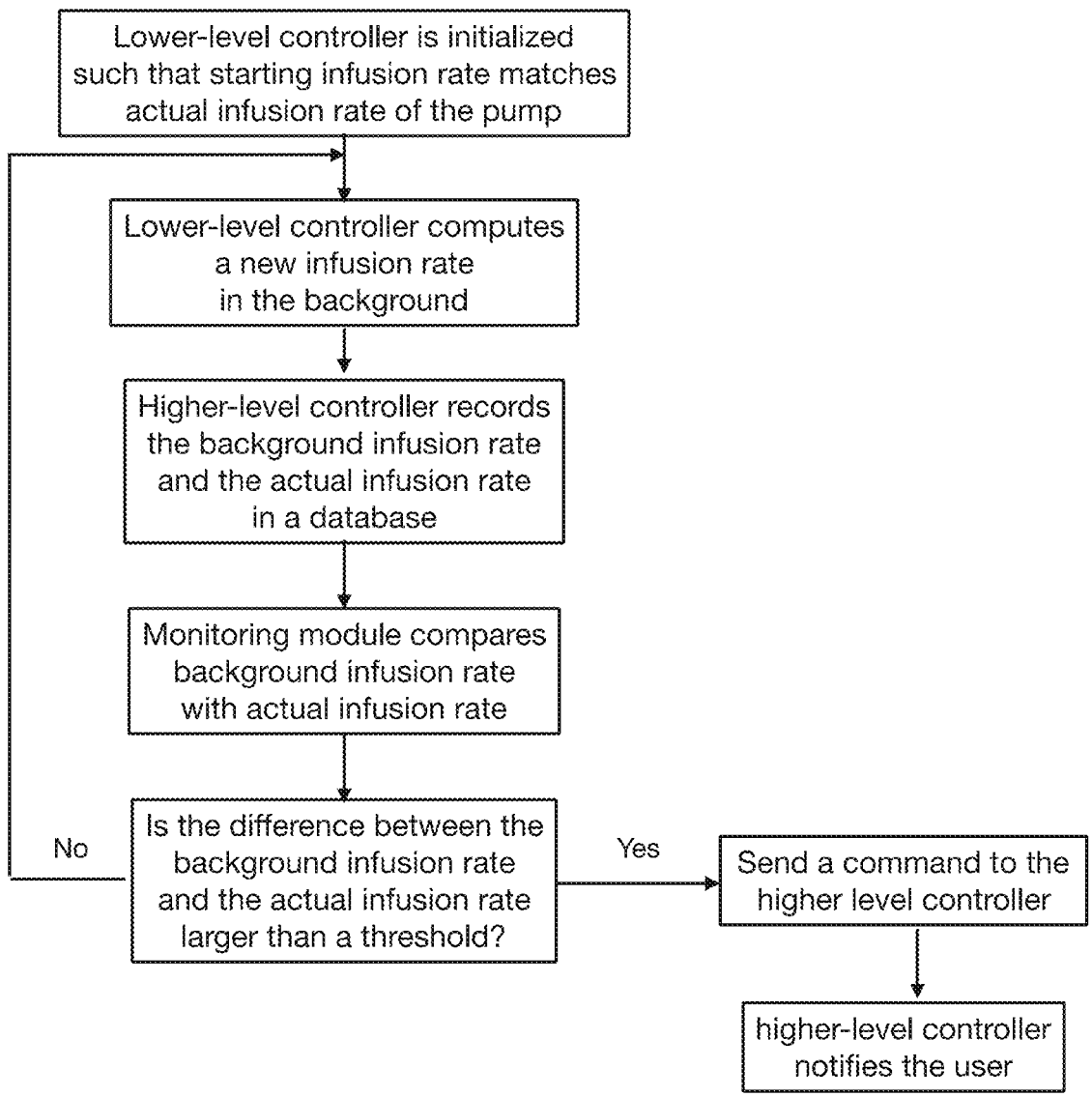
FIG. 30 is a flow chart that illustrates the alarm function to prevent under- or over-administration of fluid and/or drug according to embodiments.

Referring to FIG. 30, in some embodiments, the lower-level controller runs in the background and computes new infusion rates periodically. The newly computed infusion rates are kept in the background, and analyzed by the higher-level logic-based controller. The internal states of the lower-level controller are initialized such that the starting infusion rate generated by the lower-level controller matches the actual infusion rate specified by the user. In some embodiments, the lower-level controller uses a function approximator with a set of weights, where the weights are determined in a way such that the initial infusion rate generated by the lower-level controller matches the actual infusion rate specified by the user. In some embodiments, the function approximator is a neural network. As an example, given the user specified infusion rate, the weights of the function approximator was chosen such that $$w_{q,new}(0) = w_q(0)$$

$$w_{p,new}^T(0) P(z(0)) = (\text{pump infusion rate})(1 + w_q^T(0) Q(z(0)))$$

As discussed above, after initialization, the lower-level controller periodically computes a new infusion rate in the background and sends the background infusion rate to the higher-level logic-based controller. The higher-level controller records the current value of the background infusion rate and the current value of the actual infusion rate in a monitoring data base. A monitoring module periodically analyzes the background infusion rate and the actual infusion rate. If the difference between the background infusion rate and the actual infusion rate is more than a set threshold (e.g., the difference between the rates are 1%, 5%, 10% etc. more or less than the actual infusion rate), then the monitoring module sends a command to the higher-level logic controller to notify the user of over-administration or under-administration. The notification could be in the form of an audio/visual alarm or by generating a number or index indicating the difference between the actual infusion rate and the background infusion rate.

In some embodiments, the monitoring module sends a command to the higher-level logic-based controller to notify the user when it identifies at least one entry in the monitoring database with an absolute value of difference between actual infusion rate and background infusion rate greater than a set threshold. In some embodiments, the monitoring module sends a command to the higher-level logic-based controller to notify the user when it identifies in the monitoring database at least two consecutive entries or two non-consecutive entries in a set time interval with an absolute value of difference between actual infusion rate and background infusion rate greater than a set threshold.

In some embodiments, alarm system is implemented on an infusion pump, where the infusion pump periodically receives data from a hemodynamic monitor. In some embodiments, the audio and/or visual alarm can be generated on the infusion pump using a graphical user interface. In some embodiments, a dedicated light of a specific color (e.g., red, or yellow, or blinking red, blinking yellow) could turn on accompanied by an audio alarm to indicate under-administration or over-administration of fluid and/or cardiovascular drug.

The invention claimed is:

1. A method for fluid and/or cardiovascular drug administration, the method comprising:
   receiving by way of a user interface at least one initial infusion rate;
   receiving from a sensor hemodynamic measurements of a subject by a hierarchical control architecture system;
   wherein the hierarchical control architecture system comprises:
   at least one lower-level controller; and
   a higher-level logic controller;
   wherein the subject's hemodynamic measurements are received by the higher-level logic controller and the at least one lower-level controller;
   wherein the at least one lower-level controller and the higher-level logic controller are in communication with one another; and
   wherein the at least one lower-level controller has an internal dynamical system model that adapts to a dynamical system model of the subject;
   initializing parameters of the internal dynamical system model of the at least one lower-level controller based at least in part on the at least one initial infusion rate such that the lower-level controller generates an infusion rate equal to the at least one initial infusion rate;
   generating a new infusion rate by the lower-level controller at set time intervals based at least in part on the hemodynamic measurements and the parameters of the internal dynamical system model of the at least one lower-level controller;

notifying the user and disengaging the at least one lower-level controller if at least one infusion therapy performance criterion is violated by dropping below or exceeding a set threshold; and administering the fluid and/or cardiovascular drug at the new infusion rate to the subject.

2. The method of claim 1, wherein violation of the at least one infusion therapy performance criterion is determined by comparing the set threshold with the difference between the hemodynamic measurements of the subject and target hemodynamic data in a set time interval.

3. The method of claim 1, wherein the internal dynamical system model of the at least one lower-level controller uses a function approximator comprising a set of basis functions and a set of weights to approximate an unknown function describing distribution of the fluid and/or drug in the body of the subject.

4. The method of claim 3, wherein the function approximator is a neural network with sigmoidal basis functions.

5. The method of claim 3, wherein at least one element of the set of weights is reset to a new value if the new infusion rate falls outside the safe range.

6. The method of claim 1:
wherein the at least one lower-level controller comprises a first lower-level controller initially engaged by the higher-level controller; and
wherein the higher-level controller automatically engages a second lower-level controller when at least one infusion therapy performance criterion, which is a patient-related infusion therapy performance criterion, is violated.

7. The method of claim 6, wherein the patient-related infusion therapy performance criterion comprises improvement in hemodynamic measurements of the subject while administering one or more fluid or cardiovascular drug.

8. The method of claim 1, wherein the internal dynamical system model adapts to the dynamical system model of the subject by updating the parameters of the internal dynamical system of the at least one lower-level controller based at least in part on current values of the parameters of the internal dynamical system of the at least one lower-level controller and the hemodynamic measurements of the subject.

9. The method of claim 1, wherein the higher-level logic controller verifies that the new infusion rate is in a safe range specified by the user and if not the higher-level logic controller changes at least one parameter of the internal dynamical system model of the at least one lower-level controller.

10. The method of claim 1, wherein the hierarchical control architecture system further comprises a second lower-level controller, wherein the first lower-level controller is initially engaged through the higher-level controller, wherein the higher-level controller recommends additional engagement of the second lower-level controller when at least one of the infusion therapy performance criterion is violated.

11. The method of claim 1, wherein the hemodynamic measurement of the subject comprises the subject's blood pressure, heart rate, stroke volume variation, urine output rate, urine output, central venous pressure, pulse pressure variation, dynamic arterial elastance, systolic pressure variation, mean arterial pressure, systolic pressure, diastolic pressure, cardiac output, cardiac index, systemic vascular resistance, or stroke volume.

12. The method of claim 1, wherein the violation of the at least one infusion therapy performance criterion is determined by:

a) comparing the rate of change of the parameters of the internal dynamical system model of the at the last one lower-level controller with the set threshold; and/or b) observing a sustained increase in infusion rate without improvements in the subject's fluid resuscitation, hemodynamic, or cardiovascular status as measured by hemodynamic measurements.

* * * * *